(12) United States Patent
Young

(10) Patent No.: US 10,500,139 B2
(45) Date of Patent: Dec. 10, 2019

(54) FORMULATIONS AND MATERIALS WITH CATIONIC POLYMERS

(71) Applicant: UCL BUSINESS LTD, London (GB)

(72) Inventor: Anne Margaret Young, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 14/908,911

(22) PCT Filed: Jul. 31, 2014

(86) PCT No.: PCT/GB2014/052349
§ 371 (c)(1),
(2) Date: Jan. 29, 2016

(87) PCT Pub. No.: WO2015/015212
PCT Pub. Date: Feb. 5, 2015

(65) Prior Publication Data
US 2016/0184190 A1 Jun. 30, 2016

(30) Foreign Application Priority Data

Aug. 2, 2013 (GB) .................................. 1313898.7

(51) Int. Cl.
*A61K 6/087* (2006.01)
*A61K 6/083* (2006.01)
(Continued)

(52) U.S. Cl.
CPC ............ *A61K 6/087* (2013.01); *A61K 6/0067* (2013.01); *A61K 6/0276* (2013.01); *A61K 6/033* (2013.01);
(Continued)

(58) Field of Classification Search
None
See application file for complete search history.

(56) References Cited

U.S. PATENT DOCUMENTS

| 5,180,426 A | 1/1993 | Sumita | |
|---|---|---|---|
| 5,382,284 A * | 1/1995 | Arnold | A61C 5/007 106/35 |

(Continued)

FOREIGN PATENT DOCUMENTS

| WO | 2007007065 A2 | 1/2007 |
|---|---|---|
| WO | 2008037991 A1 | 4/2008 |

(Continued)

OTHER PUBLICATIONS

Abou Neel et al., "Chemical, modulus and cell attachment studies of reactive calcium phosphate filler-containing fast phoot-curing, surface-degrading, polymeric bone adhesives", Acta Biomater, 6(7): 2695-2703 (2010).

(Continued)

*Primary Examiner* — Bethany P Barham
*Assistant Examiner* — Dominic Lazaro
(74) *Attorney, Agent, or Firm* — Nixon Peabody LLP; Mark J. FitzGerald; Ravinderjit Braich

(57) ABSTRACT

This invention provides fluid formulations and materials produced therefrom for repairing dental and bone defects, processes for the production of the fluid formulations and materials, and to uses of these formulations and materials. In particular, the invention provides the use cationic polymers such as polylysine in these formulations and materials, and the advantageous properties derived therefrom which include mechanical and antibacterial properties.

20 Claims, 39 Drawing Sheets

(51) Int. Cl.
| | |
|---|---|
| A61K 6/033 | (2006.01) |
| A61K 6/027 | (2006.01) |
| A61L 27/26 | (2006.01) |
| A61L 27/16 | (2006.01) |
| A61L 27/18 | (2006.01) |
| A61L 27/12 | (2006.01) |
| A61L 27/10 | (2006.01) |
| A61L 27/46 | (2006.01) |
| A61K 6/00 | (2006.01) |
| A61L 27/54 | (2006.01) |
| A61L 24/00 | (2006.01) |
| A61L 27/48 | (2006.01) |

(52) U.S. Cl.
CPC .......... *A61K 6/083* (2013.01); *A61L 24/0084* (2013.01); *A61L 27/10* (2013.01); *A61L 27/12* (2013.01); *A61L 27/16* (2013.01); *A61L 27/18* (2013.01); *A61L 27/26* (2013.01); *A61L 27/46* (2013.01); *A61L 27/48* (2013.01); *A61L 27/54* (2013.01); *A61L 2300/404* (2013.01); *A61L 2430/02* (2013.01); *A61L 2430/12* (2013.01)

(56) References Cited

U.S. PATENT DOCUMENTS

| | | | | |
|---|---|---|---|---|
| 5,861,445 | A * | 1/1999 | Xu | A61K 6/0008 106/35 |
| 9,238,715 | B2 | 1/2016 | Chan et al. | |
| 2010/0029549 | A1 * | 2/2010 | Chaput | A61K 9/0024 514/1.1 |

FOREIGN PATENT DOCUMENTS

| | | | |
|---|---|---|---|
| WO | 2009105614 | A2 | 8/2009 |
| WO | WO2011081976 | * | 7/2011 |

OTHER PUBLICATIONS

Abou Neel et al., "Viscoelastic and biological performance of low-modulus, reactive calcium phosphate-filled, degradable polymeric bone adhesives", Acta Biomater, 8(1): 313-320 (2012).
Advincula et al., "Polypeptide-Catalyzed Silica for Dental Applications", J Biomed Mater Res B Appl Biomater., 88 (2):321-31 (2009).
Arshad, Thesis: "Modified Dental Composites for Bone Repair", Institute of Biomedical Engineering, Eastman Dental Institute, Royal National Orthopaedic Hospital NHS Trust, University College London (2015). (94 pp.).
Chiu et al., "Controlled release of thymosin β4 using collagen—chitosan composite hydrogels promotes epicardial cell migration and angiogenesis", J Control Release, 155(3):376-85 (2011).
Ciucurel et al., "A Poloxamine-Polylysine Acrylate Scaffold for Modular Tissue Engineering", Journal of Biomaterials Science Polymer Ed, 22(18): 2515-2528 (2011).
Dakkouri et al., Thesis: "Development of Novel Remineralising Antimicrobial Dental Composites", Eastman Dental Institute, University College London (2015). (204 pp.).
Delihas et al., "High sensitivity of Mycobacterium species to the bactericidal activity by polylysine", FEMS Microbiol Lett, 132(3):233-7 (1995).
Epolyly Fact Sheet.
Galli et al., "In vitro osteoblastic differentiation of human mesenchymal stem cells and human dental pulp stems cells on poly-L-lysine-treated titanium-6-aluminium-4-vanadium", J Biomed Mater Res, 97A: 118-126 (2011).
Gellynck et al., "Cell attachment and response to photocured, degradable bone adhesives containing tricalcium phosphate and purmorphamine", Acta Biomater, 7(6): 2672-2677 (2011).
Gheduzzi et al., "Mechanical characterisation of three percutaneous vertebroplasty biomaterials", J Mater Sci Mater Med., 17:421-426 (2006).
Ismail, Thesis: "Development of Novel Remineralising Antimicrobial Brushite Cements", Eastman Dental Institute, University College London (2014). (353 pp.).
Kadlecova et al., "DNA delivery with hyperbranched polylysine: A comparative study with linear and dendritic polylysine", J Control Release, 169(3): 276-288 (2013).
Kangwankai, Thesis: "Volume, Mass and Surface Roughness Changes of Antibacterial and Calcium Phosphate-Containing Dental Composites after Simulated Wear", Eastman Dental Institute, University College London (2014). (124 pp.).
Kar et al., "Synthesis and Characterization of Poly-l-lysine-Grafted Silica Nanoparticles Synthesized via NCA Polymerization and Click Chemistry", Langmuir, 26(8): 5772-81 (2010).
Khan, Thesis: "Development of Antibacterial and Remineralising Composite Bone Cements", Eastman Dental Institute, University College London (2015). (353 pp.).
Kim et al., "Biodegradable photo-crosslinked poly(ether-ester) networks for lubricious coatings", Biomaterials, 21(3): 259-65 (2000).
Korzhikov et al. "Polymers in Orthopedic Surgery and Tissue Engineering: From Engineering Materials to Smart Biofunctionalization of a Surface", Polymer Science Ser. A, 54(8):585-601 (2012).
Kumar et al., "Polyanhydrides: an overview", Adv Drug Deliv Rev., 54(7):889-910 (2002).
Li et al., "Vascular Endothelial Growth Factor Release from Alginate Microspheres Under Simulated Physiological Compressive Loading and the Effect on Human Vascular Endothelial Cells", Tissue Eng Part A, 17(13-14):1777-85 (2011).
Liaquat, Thesis: "Development of Antibacterial-releasing Dental Composites with High Strength and Dentine Bonding", Eastman Dental Institute, Division of Biomaterials and Tissue Engineering, University College London (2015). (387 pp.).
Lohmann et al., "Ceramic and PMMA particles differentially affect osteoblast phenotype", Biomaterials 23(8):1855-63 (2002).
Martin-Lopez et al., "Differential Adhesiveness and Neurite-promoting Activity for Neural Cells of Chitosan, Gelatin, and Poly-l-Lysine Films" J Biomater Appl, 26(7):791-809 (2012).
Mehdawi et al., "Development of remineralizing, antibacterial dental materials", Acta Biomaterialia, 5(7): 2525-39 (2009).
Mehdawi et al., "High strength re-mineralizing, antibacterial dental composites with reactive calcium phosphates", Dent Mater., 29(4):473-84 (2013).
Niinomi, "Low Modulus Titanium Alloys for Inhibiting Bone Atrophy", Biomaterials Science and Engineering, Prof. Rosario Pignatello (Ed.), pp. 249-268 (2011).
Nor et al., "Development of novel remineralising antimicrobial brushite cements", an oral presentation made at the IADR General Session and Exhibition, Cape Town, South Africa, Jun. 25-28, 2014.
Oh et al., "Temperature rise and setting of beta-TCP-MCPM bone cement containing dense beta-TCP granules", Current Applied Physics, 5:489-492 (2005).
Panpisut, Dissertation: "Development of a Remineralising, Antibacterial Dental Composite", Eastman Dental Institute, University College London (2013). (121 pp.).
Schmitz et al., "Reconstruction of Bone Using Calcium Phosphate Bone Cements: A Critical Review", J Oral Maxillofac Surg., 57(9):1122-6 (1999).
Shi et al., "The Improved Biological Performance of a Novel Low Elastic Modulus Implant", PLoS ONE, 8(2): e55015 (2013).
Shih et al., "Microbial synthesis of poly(epsilon-lysine) and its various applications", Bioresource Technology, 97 (9):1148-59 (2006).
Sideridou et al., "Reactivity of Benzoyl Peroxide/Amine System as an Initiator for the Free Radical Polymerization of Dental and Orthopaedic Dimethacrylate Monomers: Effect of the Amine and Monomer Chemical Structure", Macromolecules, 39(6):2072-80 (2006).
Stanczyk et al., "Thermal analysis of bone cement polymerisation at the cement-bone interface", J. Biomech. 37 (12):1803-10 (2004).
Stanczyk, "Study on modelling of PMMA bone cement polymerisation", J. Biomech., 38(7):1397-403 (2005).

(56) References Cited

OTHER PUBLICATIONS

Takada et al., "Preparation and Properties of Bio-Based Epoxy Montomorillonite Nanocomposites Derived from Polyglycerol Polyglycidyl Ether and ε-Polylysine", Journal of Applied Polymer Science, 113(1):479-84 (2009).
Temenoff et al., "Injectable biodegradable materials for orthopedic tissue engineering", Biomaterials, 21 (23):2405-12 (2000).
Timmer et al., "In vitro degradation of polymeric networks of poly(propylene fumarate) and the crosslinking macromer poly(propylene fumarate)-diacrylate", Biomaterials, 24(4):571-7 (2003).
Van Landuyt et al, "Systematic review of the chemical composition of contemporary dental adhesives", Biomaterials, 28(26):3757-85 (2007).
Walters et al., "Calcium phosphate-precipitating, antimicrobial composite biomaterials", in Journal of Tissue Engineering and Regenerative Medicine, 8:263-4 (2014).
Walter et al., "Novel remineralising, antimicrobial dental & orthopaedic resin-based composites", TERMIS-EU 2013 (Tissue Engineering & Regenerative Medicine International Society European Chapter Meeting), at Istanbul,Turkey (Jun. 2013).
Walters, Thesis: "Remineralising composites with improved cytocompatibility and containing antimicrobial agents for conservative treatment of caries" (2016). (142 pp.).
Walters et al., "Remineralising antimicrobal dental and orthopaedic composits", Biomaterials & Tissue Engineering & Paediatric Dentisry, UCL Eastman Dental Institute poster (2014).
Wang et al., "Dynamic mechanical properties of cortical bone: The effect of mineral content", Materials Letters, 59:2277-80 (2005).
Wolff et al., "Degradable injectable bone cement in maxillofacial surgery: indications and clinical experience in 27 patients", Journal of Cranio-Maxillofacial Surgery, 32(2):71-79 (2004).
Young et al., "Chemical characterization of a degradable polymeric bone adhesive containing hydrolysable fillers and interpretation of anomalous mechanical properties", Acta Biomaterialia, 5(6):2072-83 (2009).
Young, "Antibacterial releasing dental restorative materials"; Drug-device combination products: Delivery technologies and applications Edited by A Lewis, Biocompatibles UK Ltd, UK Woodhead Publishing Series in Biomaterials No. 22, Chapter 11, pp. 246-279 2009.
Zacharaki, Dissertation: "Development of Novel Antibacterial and Remineralising Dental Composites—An in vitro study", Eastman Dental Institute, University College London (2015).(146 pp.).
Zhao et al., "Reactive calcium-phosphate-containing poly(ester-co-ether) metacrylate bone adhesives: Setting, degradation and drug release considerations", J Mater Sci: Mater Med, 22(9):1993-2004 (2011).
Zhu et al., "Characterization of Bacteriostatic Sausage Casing: A Composite of Bacterial Cellulose Embedded with εPolylysine", Food Sci. Biotechnol., 19(6):1479-84 (2010).
Zhou et al., "Multi-walled carbon nanotubes/epilson-polylysine nanocomposite with enhanced antibacterial activity", Letters Applied Microbiology, 52(1):76-83 (2010).
Lin et al., "One-pot fabrication and antimicrobal properties of novel PET nonwoven fabrics", Biomed. Mater., 6 (4):045009 (2011). (7 pp).
Panpisut et al., "Dental Composites with Calcium/Strontium Phosphates and Polylysine", PLoS One 11(10): e0164653 (2016). (19 pages).
Beyth et al., "Antibacterial activity of dental composites containing quaternary ammonium polyethylenimine nanoparticles against *Streptococcus mutans*", Biomaterials 27(21):3995-4002 (2006).
Beyth et al., "Polyethyleneimine nanoparticles incorporated into resin composite cause cell death and trigger biofilm stress in vivo", Proc. Natl. Acad. Sci. U.S.A. 107(51):22038-22043 (2010).
Imazato et al., "Antibacterial activity of MDPB polymer incorporated in dental resin", J. Dent. 23(3):177-181 (1995).
Samal et al., "Cationic polymers and their therapeutic potential", Chem. Soc. Rev. 41(21):7147-7194 (2012).
Kangwankai et al., "Monomer conversion, dimensional stability, strength, modulus, surface apatite precipitation and wear of novel, reactive calcium phosphate and polylysine-containing dental composites", PloS One 12(11):e0187757 (2017). (19 pages).

* cited by examiner

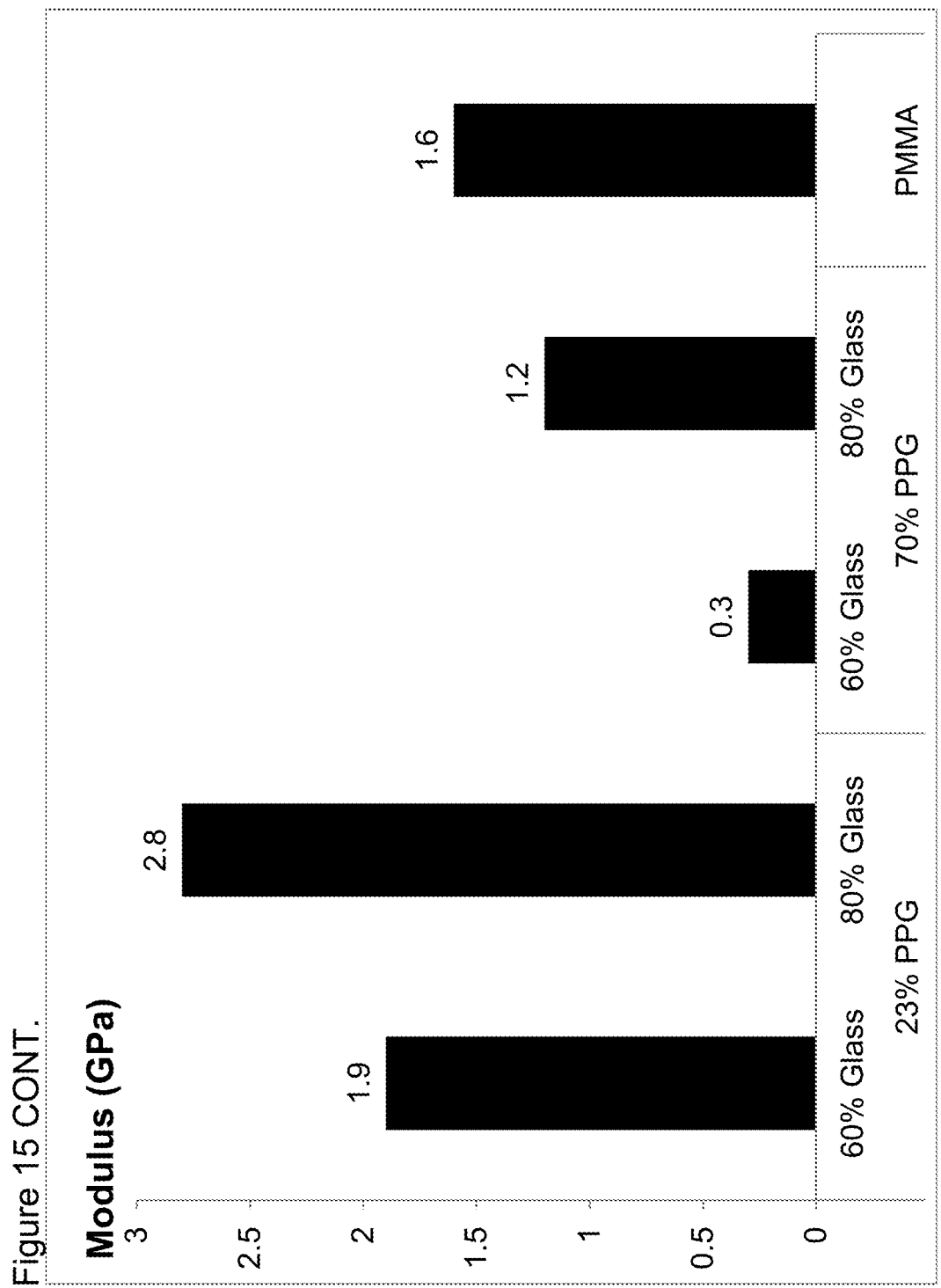

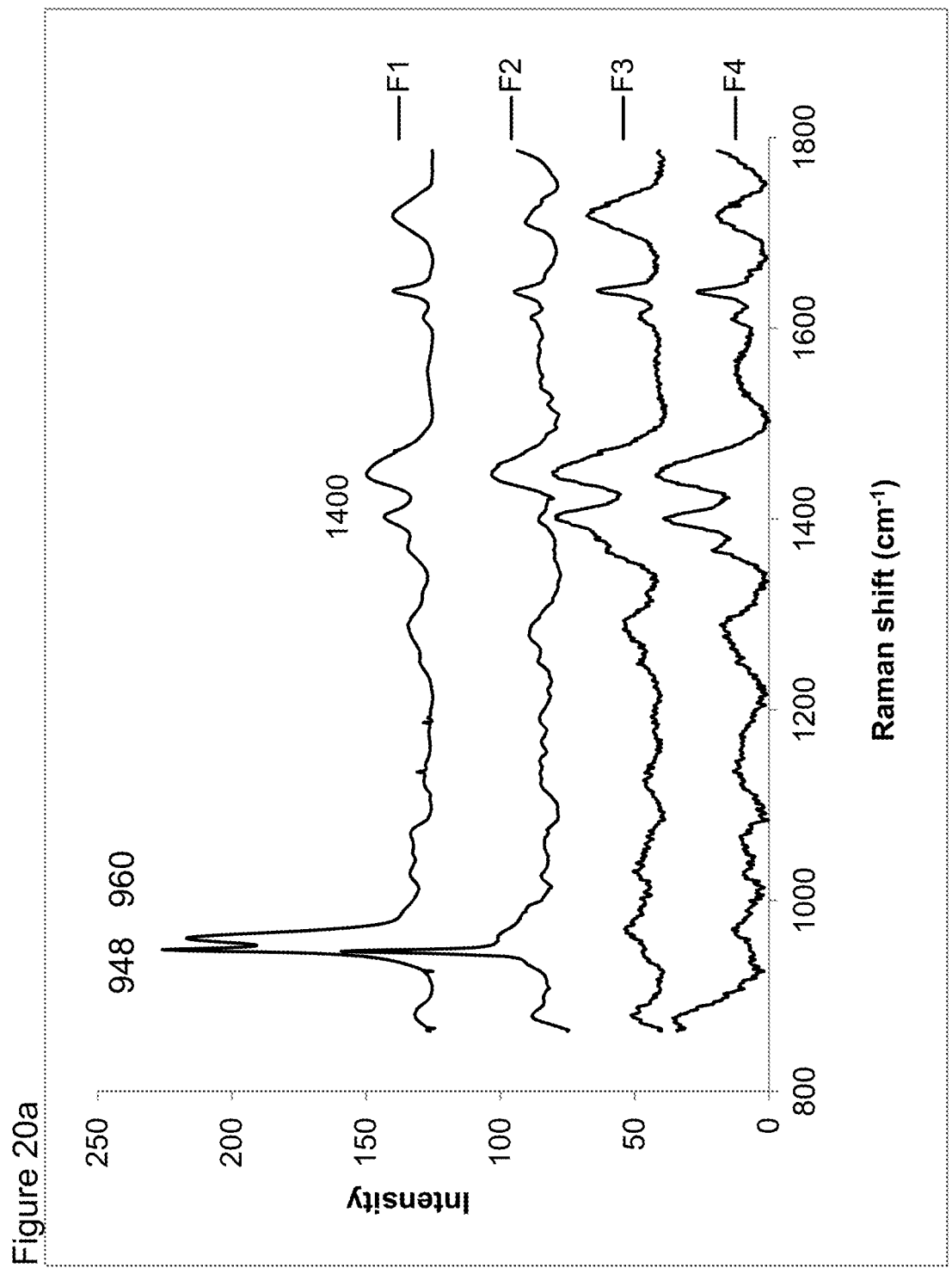

Figure 23

Mass loss due to component release minus mass gain due to water binding (mg/cc)

- Formula A 10% CaP
- Formula C 20% CaP

Categories: 7 days in water, 7 days in SBF

FORMULATIONS AND MATERIALS WITH CATIONIC POLYMERS

CROSS REFERENCE TO RELATED APPLICATIONS

This Application is a 35 U.S.C. § 371 National Phase Entry Application of International Application No. PCT/GB2014/052349 filed Jul. 31, 2014, which designates the U.S., and which claims benefit under 35 U.S.C. § 119(b) and 37 CFR 1.55(a) of Great Britain Application No. 1313898.7 GB, filed Aug. 2, 2013, the contents of each of which are incorporated herein by reference in their entireties.

TECHNICAL FIELD

This invention provides fluid formulations and materials produced therefrom for repairing dental and bone defects, processes for the production of the fluid formulations and materials, and to uses of these formulations and materials. In particular, the invention provides the use cationic polymers in these formulations and materials, and the advantageous properties derived therefrom.

BACKGROUND TO THE INVENTION

Dental caries, bone diseases and bone fractures are some of the most common ailments in all societies. For example, almost 40% of UK adults have at least one untreated carious tooth, and this rises to 60-90% for children or across the whole population in deprived nations. Further, currently 50-60% of postmenopausal women will suffer an osteoporotic fracture, commonly of the hip, vertebra or wrist. Conventional composites and cements that are currently used to treat these diseases have a number of disadvantageous properties, which are discussed below. A great need therefore exists for improved materials to treat those in need of treatment.

Materials which are initially liquid and mouldable but that can set rapidly in situ giving immediate structural support and adhesion to surrounding tissues are of great value in bone tissue-engineering applications as well as dental, maxillofacial and orthopaedic surgeries. As they set from liquid to solid, micromechanical bonds are formed with the surrounding surfaces. The adhesive effect is especially strong with rough surrounding surfaces.

Setting of such materials may, for example, be initiated by chemical initiators or by exposure to visible or UV light (especially in cases of chemical polymerisation and cross-linking, such as in double bond containing (eg. methacrylate) polymeric formulations), or may be a result of other chemical reactions upon mixing of two components (eg acid/base in glass ionomer dental and brushite-forming bone cements) or solvent removal or evaporation from the initial liquid formulation.

For example, injectable methacrylate based dental restorative composites, adhesives and poly(methyl methacrylate) (PMMA) bone cements have been widely used for applications such as tooth restoration and for fixing of orthopaedic implants. After injection of the initially fluid formulation (containing various methacrylate monomers and inorganic particles or PMMA powder in combination with liquid methyl methacrylate monomer), curing occurs, due to the presence of chemical initiators, and results in a solid material.

As mentioned above, conventional (e.g. methacrylate-based) composites and cements have a number of disadvantageous properties. The PMMA cements and dental restorative composites discussed above are strong, but curing of large volumes generates excessive heat and material shrinkage which may cause necrosis of surrounding tissue or debonding. Additionally, if setting is slow, release of potentially toxic un-polymerised compound is a problem[1,2]. PMMA also causes potential long-term biocompatibility problems due to production of wear particles [3].

Dental caries is associated with bacteria such as *Streptococcus mutans* and *S. sorbrinus* that, through acid production, cause hydroxyapatite dissolution and enamel/dentine demineralisation. Subsequent proteinase action degrades remaining dentinal collagen. Damaged or infected tooth structure must be partially or totally replaced in order to halt disease progression, preserve function and improve aesthetics. Due to mercury concerns and patient demand, amalgam restorations are increasingly being replaced by more aesthetic materials such as composites. Composites have high strength, but their main reason for replacement is bond damage and recurrent caries Antibacterial agents may be incorporated into dental composites or antibiotics into PMMA bone cements to decrease the risk of infection [13, 14, 16]. However, the release from conventional composites and cements is restricted, and requires high drug content which usually decreases material strength.

Metal screws, pins and plates are increasingly used in arthritic joint replacement or osteoporotic fracture repair due to rising population age and disease incidence. Titanium alloys are often employed due to their biocompatibility. High strength is required to enable use of thin plates and finer screws/pins. For a given material type, maximum strength is usually proportional to modulus but high modulus causes bone atrophy. Titanium screw strength is typically only 1-2% of the modulus [15]. Other problems can include infection (osteomyelitis) and screw loosening particularly from bone weakened by osteoporosis. Titanium screws and pins can be designed to encourage hydroxyapatite (HA) deposition which encourages osseointegration. Alternatively, early metal fixation may be improved by combining screws/pins with bone cements (screw augmentation/bone filling).

DESCRIPTION OF THE INVENTION

The present invention provides cationic polymers for use in formulations for tooth or bone repair, which provides a number of surprising advantages. Through extensive experimentation, it is shown herein that the use of cationic polymers, preferably ε-polylysine, may impart many advantages to the material, i.e. to the composite, compomer, RMGIC, GIC, adhesive, surface coating and cement materials produced from the formulations of the invention. Such advantages include increased toughness, reduced modulus whilst maintaining high strength (i.e. more flexible, less brittle), increased water sorption, induced swelling to counteract polymerisation shrinkage, increased adhesion, increased antibacterial activity; increased release of active agents, or increased rates of cross-linking/polymerisation.

Being able to counteract composite shrinkage and subsequent bacterial penetration/tooth demineralisation is a particular advantage, since this is the main cause of dental composite failure. Conversely, composite fracture as a result of low toughness is now rare as a result of high strength.

A further advantage of ε-polylysine is its low human cell toxicity in comparison with other antibacterial agents or activators for methacrylate polymerisation. In preferred embodiments of the invention, one or more of these properties are achieved.

In addition, the use of cationic polymers with materials described herein can lead to more rapid formation of a bone or dentine-like layer on the materials. This is demonstrated herein in simulated body fluids, and in vivo this may inhibit bacterial microleakage, and provide a mechanism for the material to self-heal after stress. The cationic polymer may then re-adsorb on this layer to provide an antibacterial-containing surface with both flexible polymers and rigid calcium phosphate particles, thereby mimicking dentine and bone.

ε-Polylysine (PLS) has FDA approval as a food preservative. It is highly water soluble and stable at high temperature in both acidic and alkaline solution. The epsilon form produced by bacteria has the amide linkage between the ε-amino and α-carboxyl groups and is considered more biocompatible than the alpha form. It is antibacterial, biodegradable and highly water soluble. It has been used as an emulsifying agent, preservative, dietary agent, drug carrier, antibacterial and anticancer agent enhancer. As with many other NH containing molecules the $NH_2$ groups on PLS make it effective against gram positive and negative bacteria in addition to spores. The large number of positive electrostatic charges on the PLS enable bacterial cell attachment followed by outer bacterial membrane stripping [33]. The NH groups on polylysine also enable it to form polyplexes with DNA in a similar manner to polymers such as polyethylenimine (PEI) used for non viral gene delivery. The positively charged PLS groups in the polyplexes aid cell attachment, cell membrane transfer and provide buffering that together enhance gene transfection [34]. Polylysine modification of titanium for bone and dental implants has been shown to enhance mysenchymal and dental pulp stem cell attachment. The polylysine also beneficially increased expression of osteoblastic differentiation marker genes [20]. Furthermore, polylysine chemically attached to poly(ethylene co propylene) oxide or silica particles has been shown to increase endothelial cell attachment [21], or kill bacteria [22] respectively. The use of polylysine with biomaterials has also been described in [23]. Other cationic and polyamide polymers with therapeutic benefits have recently been reviewed [35], but there is no mention of their use in cements for tooth or bone repair.

Without being bound by theory, it is believed that having only positive charges on the cationic polymer would enable the chains to extend when water is absorbed and diffuse via reptation through the material described herein. Reptation generally occurs through polymer melts. It may, however, also occur through the solid material if water sorption causes localized plasticization to allow the polymer chains to move more freely. In preferred embodiments, the cationic polymer is released from the material and re-adsorbs onto a layer on the material.

A further aspect of the invention provides novel formulations for tooth or bone repair that have enhanced properties over those in the prior art, as described herein.

Additional formulations of materials that can be used in the present invention together with cationic polymers are described in WO 2008/037991, incorporated herein by reference.

One aspect of the invention provides a process for the production of a material comprising the steps of:
i) providing a fluid formulation of the invention as described herein comprising a cationic polymer; and
ii) optionally introducing said fluid formulation into a site of use.

Preferably, the material is for repair of tooth or bone defects. Preferably, the material is a composite, compomer, RMGIC, GIC, adhesive or surface coating for repair of tooth or bone defects.

In some embodiments, the fluid formulation is introduced into a site of use by e.g. injecting, applying or packing the fluid formulation into the site of use.

In preferred embodiments, the invention provides a process for production of a material comprising:
i) providing a fluid formulation comprising (1) at least one compound capable of polymerisation and/or cross-linking, and (2) optionally a filler, and (3) a cationic polymer;
ii) optionally introducing said fluid formulation into a site of use;
iii) polymerising and/or cross-linking said compound, to form a solid polymer matrix comprising the cationic polymer.

In some preferred embodiments, the filler comprises the cationic polymer.

In some embodiments, the cationic polymer is in a fluid phase of the fluid formulation as described herein. These embodiments are particularly preferred when the at least one compound capable of polymerisation and/or cross-linking is water soluble, for example in GICs and RMGICs. Preferably, the fluid formulation comprises an aqueous cationic polymer solution.

In some embodiments, the filler comprises a reactive component, and the method further comprises:
iv) causing or allowing said filler to react with water to produce a solid filler material comprising the cationic polymer which is dispersed throughout the material Particular fluid formulations are described in more detail in the following description.

In preferred embodiments of the invention, the material has enhanced properties selected from any one of:
(i) Reduced modulus/increased flexibility, e.g. while maintaining strength;
(ii) Increased toughness;
(iii) Increased resilience;
(iv) Increased adhesion;
(v) Increased release of active agents incorporated into the material;
(vi) Increased anti-bacterial activity, e.g. while maintaining human cell compatibility;
(vii) Increased water sorption, which may e.g. combat polymerisation shrinkage and increase release of an active agent;
(viii) Increased formation of a self-healing layer on the material; and/or
(ix) Increased cross-linking/polymerisation without higher levels of more conventional toxic activators Preferably, the enhanced properties are compared to a reference material not having a cationic polymer of the invention.

Accordingly, an aspect of the present invention provides a fluid formulation comprising (1) at least one compound capable of polymerisation and/or cross-linking, (2) optionally a filler, and (3) a cationic polymer. In some embodiments, the filler comprises the cationic polymer. In some embodiments, the filler comprises a reactive component which is capable of reacting with water to produce a solid filler, i.e. reacting with water within the solid polymer matrix formed by the at least one compound capable of polymerisation and/or cross-linking.

The compound capable of polymerising and/or cross-linking, filler, reactive component and cationic polymer are preferably as described herein.

By 'fluid formulation' is meant a fluid composition having a viscosity that enables it to be introduced into a site of use, e.g. by injection or packing. As will be readily appreciated by one skilled in the art, in light of the following description, the viscosity required may depend upon the exact site and mode of application. For example with larger cavities with easy access, putty-like consistencies may be suitable. More liquid formulations (~1 to 100 mPas) may spread better over the tissue, however, providing better adhesion. If the material is to be injected through a fine needle then the viscosity must be reduced. This viscosity may be reduced by lowering the level of filler.

'Cross-linking', 'polymerisation', 'curing' or 'setting' as used herein refers to the solidification process, by which the initially fluid formulation forms a solid 3-dimensional polymeric network or 'matrix'. This may be achieved by chemical reaction, i.e. the formation of covalent or ionic bonds between monomers ('polymerisation'; oligomerisation) or between polymeric chains (chemical 'cross-linking'), or may be by physical interactions between polymeric chains (such as occurs in the formation of crystalline regions) in a three dimensional network structure. The term 'cross-linking', as used herein, may refer to chemical cross-linking or physical cross-linking. Chemical cross-linking and/or polymerisation may be achieved by means including heat ('thermal curing'), UV or visible light ('photo curing') or mixing with a chemical initiator ('chemical curing'). Solidification may also occur by physical cross-linking, which may, for example, be due to removal or evaporation of solvent from a fluid composition or fluid polymer-containing liquid, or due to a change of temperature.

Preferably, the fluid formulation comprises a filler having a water-consuming reactive component, e.g. as described herein or in WO 2008/037991, is an inorganic compound, or a mixture of inorganic compounds, which is incorporated into the fluid formulation. Usually the reactive component will be of a solid particulate nature and between 0.5 and 200 micron in diameter. The fillers used in the present invention are capable of undergoing a chemical reaction within the solid polymer matrix, which reaction may alter the chemical and physical properties of the particles, and which may preferably result in the formation of new chemical species. The solid material formed from this precipitation may have a lower density than that of the starting compound(s), due to the extra water content, and hence may occupy a larger volume.

The fluid formulations according to the invention may be prepared by mixing solid particles comprising the filler, e.g. a cationic polymer and optionally other components, with a fluid phase. In some embodiments, the fluid phase comprises a polymerisable/cross-linkable compound. The fluid phase may further include diluents such as HEMA, TEGDMA PPGDMA and the like and/or solvents, such as ethyl acetate, acetone, alcohol, water and the like. In some embodiments, the cationic polymer is mixed into the filler as solid particles. In alternative embodiments, the cationic polymer may be in a fluid phase when mixed into the fluid formulation.

It is understood that the components of the fluid formulation—i.e the filler and polymerisable/cross-linkable compound—may be supplied or prepared separately, and combined when or shortly before the material is produced. As used herein, the term "filler" relates to components that are dispersed as solid particles in the fluid formulations described herein.

The fluid formulations of the invention may comprise initiators and/or inhibitors of polymerisation/cross-linking.

The filler comprises a cationic polymer, and optionally one or more components, preferably selected from a reactive component, an inert glass powder, an active agent, and fibres, preferably glass fibres and the like. As described herein, the selection of filler constituents, and the relative amounts of each constituent, can lead to the advantageous properties described herein.

The amount of filler depends upon the application.

In some embodiments, e.g. where high strength is less important, preferably the fluid formulation comprises between about 10% and 60% by weight filler, e.g. about 10%, 20%, 30%, 40%, 50 or 60%, by weight filler, more preferably about 20, 21, 22, 23, 24, 25, 26, 27, 28, 29 or 30 wt % filler. Applications for such embodiments include lower viscosity dental adhesives, antibacterial formulations for periodontal treatment and porous brushite cements acting as scaffolds for bone repair. In some embodiments, e.g. wherein the formulation is for dental adhesives, no inert filler (i.e. no inert glass powder or fibres) is present in the filler. Preferably the formulation comprises about 24 wt % filler, the formulation comprising about 20 wt % of reactive component e.g. reactive calcium phosphate, about 2 wt % cationic polymer e.g. polylysine, and about 2 wt % active agent, e.g. chlorhexidine.

In further embodiments, e.g. for stronger, more dense brushite cements, non degradable materials for tooth or bone repair and degradable material for bone repair, preferably the fluid formulation comprises between at least about 50 wt % and 90 wt % filler, e.g. about 50%, 60%, 70%, 80%, 90% by weight filler, more preferably about 80 wt %.

The fluid formulations of the invention comprise a cationic polymer as described herein. In some embodiments, the cationic polymer is a solid (e.g. in powder form) when mixed into the fluid formulation as part of the filler. In alternative embodiments, the cationic polymer may be dissolved in the fluid phase.

In one aspect of the invention, the cationic polymer comprises a monomeric subunit having a nitrogen-containing group (e.g. an amino group). Preferably, the nitrogen-containing group is capable of developing a positive charge in aqueous solutions, e.g. at physiological pH or a pH at or below about pH 7, 8 or 9. Preferably the nitrogen-containing group has a pKa of greater than about 8, 8.5, 9, 9.5 or 10.

In some preferred embodiments, the cationic polymer comprises amino acid monomers having a sidegroup, e.g. a nitrogen-containing sidegroup, capable of developing a positive charge in aqueous solutions. Preferably, the cationic polymer is a polypeptide. Preferably the sidegroup has a pKa of greater than about 8, 8.5, 9, 9.5 or 10. In some embodiments, the sidegroup is capable of developing a positive charge in aqueous solution at physiological pH or a pH at or below about pH 7, 8 or 9.

Preferably, the cationic polymer is a homopolymer. In some embodiments, the cationic polymer may be a co-polymer.

In some embodiments, the cationic polymer has a degree of polymerization (n) between about 5 and 100 monomers, preferably between about 10 and 80 monomers, between about 15 and 50 monomers, or between about 20 and 40 monomers, most preferably between about 25 and 35 monomers, e.g. about 30 monomers.

Preferably, the cationic polymer has a molecular weight of between about 100 and 1,000,000 g/mol, e.g. between about 500 and 100,000 g/mol, preferably between about 500 and 50,000 g/mol, between about 1,000 and 25,000 g/mol, or between about 1,000 and 10,000 g/mol. In some embodiments, the cationic polymer has a molecular weight of about 1,000, 2,000, 3,000, 4000, 4,500, 4,600, 4,700, 4,800, 4,900, 5000, 6000, 7,000, 8,000, 9,000, 10,000, 15,000, 20,000, 25,000 or 30,000 g/mol, or any range between these values. Preferably, the cationic polymer has a molecular weight of about 4,700 g/mol.

In a preferred embodiment, the cationic polymer is selected from polylysine, polyarginine, polyhistamine, chitosan and the like. Most preferably, the cationic polymer is polylysine, i.e. ε-poly-L-lysine (PLS) or poly[imino[(2S)-2-amino-1-oxo-1,6-hexanediyl.

Incorporating a cationic polymer of the invention into the fluid formulation can surprisingly enhance the rheological, adhesive, and/or biological properties of both the fluid formulation and the material formed from the fluid formulation, in addition to the structural and/or mechanical properties of the material.

Polylysine and other cationic polymers have antibacterial properties themselves. Without being bound by theory, it is believed that the positive electrostatic charge on the cationic polymer (e.g. polylysine) provide an antibacterial effect by enabling bacterial cell attachment followed by outer bacterial membrane stripping. As described herein, it has been surprisingly found that, unlike other smaller antibacterial agents such as chlorhexidine, high percentages of polylysine can be released. Sufficient antibacterial release can therefore be achieved to protect against subsequent infection with low antibacterial incorporation in the fluid formulations of the invention. This is beneficial as high antibacterial levels tend to reduce material strengths. Preferably, the cationic polymer is capable of adsorbing electrostatically to a bacterial cell surface.

In addition, as demonstrated herein the cationic polymer may increase the release rate of other active agents in the fluid formulation, e.g. other antibacterial, antibiotic or other therapeutic agents, or DNA. This increased release rate both increases the effectiveness of these active agents, and also means that they can be incorporated into the fluid formulations of the invention at lower concentrations. In some embodiments wherein the formulation comprises DNA, co-release of the DNA with the cationic polymer generates polyplexes with enhanced transfection ability.

The materials or fluid formulations of the invention can therefore potentially be used simultaneously as small or large (eg DNA or protein) drug molecule controlled delivery reservoirs.

In some embodiments, the cationic polymer is released from the material after setting, and readsorbs onto the surface of the material. This enhances production of surface hydroxyapatite layers on the material, and leads to surface layers having antibacterial properties.

Further, the cationic polymer can enhance water sorption into the material, which promotes reaction of a reactive component within the material. This water sorption may reverse shrinkage of the fluid formulations of the invention during polymerisation/crosslinking of the fluid formulation or compound capable of polymerisation/crosslinking. The cationic polymer may also advantageously decrease the modulus of the material, decreasing brittleness and increasing toughness and resilience.

Further advantageous properties and uses of cationic polymers are described herein.

In some embodiments, the cationic polymer is a polyamide, and may be selected from polyacrylamide, polyisopropylacrylamide, polyethylenimine. In further embodiments, the cationic polymers may be produced from molecules such as spermidine and spermine and dental methacrylates, preferably pre-polymerised dental methacrylates including NTGGMA, DMAEMA and MDPB (12-methacryloyloxydodecylpyridinium bromide). In all these molecules the positive charge that can develop on nitrogen containing groups in acidic solutions will encourage greater attachment to bacteria than less negatively charged eukaryotic cells.

NTGGMA, DMAEMA and MDPB have been incorporated in many dental materials as monomers, however, their release is prevented as they are crosslinked with other hydrophobic monomers. To enable release of these components and their concentration on the surfaces, copolymerisation with other components would need to be prevented. In some embodiments of the invention described herein, NTGGMA, DMAEMA and MDPB are pre-polymerised before addition to the fluid formulation. Alternatively, in some embodiments these monomers are phase separated from the other hydrophobic crosslinking monomers within the fluid formulation, e.g. through the production of water in oil emulsions.

It is known that small amine containing monomers such as NTGGMA and DMAEMA can act as polymerization activators within dental composites and adhesives. As demonstrated herein, despite its large size and insolubility in the polymerising monomers, PLS can surprisingly also act as a methacrylate polymerization activator. Larger polymers such as PLS are additionally, however, much less toxic than NTGGMA or DMAEMA monomers. It is known that polymerisation of NTGGMA or DMAEMA within a composite may reduce longer term toxicity. At high levels, however phase separation from the monomer phase and then non polymerisation could occur. Prepolymerisation of NTGGMA or DMAEMA and including them at higher levels in the filler phase might therefore also provide an alternative mechanism to reduce fluid formulation toxicity whilst maintaining polymerisation activating capability.

In some embodiments, the cationic polymer is selected from polylysine, polyarginine, polyhistamine, chitosan, a polyamide such as polyacrylamide, polyisopropylacrylamide, polyethylenimine, pre-polymerised methacryates and the like as described herein.

Polymers with both positive and negative charges such as collagen, fibronectin, RGD (arginine-glycine-aspartic acid sequences) and other peptides have both N—H and COOH groups which in water may produce positive and negative charge groups on the polymer respectively. The much lower aqueous solubility of such polymers compared with PLS, however, is likely to slow their release from a methacrylate based composite. Strong ionic interactions between positive and negative groups on the polymer chains could also cause aggregation which would hamper release.

Preferably, the cationic polymer of the invention comprises substantially only positive electrostatic charges. In some embodiments, the ratio of positive to negative electrostatic charges is greater than about 1:1, 2:1, 3:1, 4:1 or 5:1. Preferably, the cationic polymer has a pKa greater than about 7, 8, 9, 10, 11 or 12.

Without being bound by theory, it is possible that having only positive charges on the cationic polymer, e.g. PLS, would enable the chains to extend when water is absorbed and diffuse via reptation through the material. Reptation generally occurs through polymer melts. It may, however, also occur through the solid material if water sorption causes localized plasticization to allow the polymer chains to move more freely.

In some embodiments, the cationic polymer is highly water soluble, with sufficient positive charge to promote adsorption on precipitated hydroxyapatite and antibacterial action.

In one aspect of the invention, the filler comprises about 0.1-50 wt % cationic polymer, preferably about 0.2-50, 0.5-25, 0.5-20, 1-20, 1-10, 1-5, 0.5-10, 0.1-10 or 0.2-10 wt % cationic polymer. In some embodiments, the filler comprises about 0.1, 0.2, 0.3, 0.4, 0.5, 1, 2, 3, 4, 5, 6, 7, 8, 9, 10, 11, 12, 13, 14, 15, 16, 17, 18, 19, 20, 25, 30, 35, 40, 45 or 50 wt % cationic polymer (e.g. PLS), or any range therein.

In one aspect of the invention, the fluid formulation comprises about 0.1-50 wt % cationic polymer, preferably about 0.2-50, 0.5-25, 0.5-20, 1-20, 1-10, 1-5, 0.5-10, 0.1-10 or 0.2-10 wt % cationic polymer. In some embodiments, the fluid formulation comprises about 0.1, 0.2, 0.3, 0.4, 0.5, 1, 2, 3, 4, 5, 6, 7, 8, 9, 10, 11, 12, 13, 14, 15, 16, 17, 18, 19, 20, 25, 30, 35, 40, 45 or 50 wt % cationic polymer (e.g. PLS), or any range therein. The cationic polymer may be provided as an aqueous solution, e.g. a 50 wt % aqueous solution.

In some embodiments, the filler comprises a reactive component, and forms a solid insoluble compound, due to the reaction of more soluble reactive components, e.g. reactive calcium or strontium phosphates mixtures (CaP or SrP) within the polymer matrix. The reaction may proceed by an acid-base type reaction where there is transfer of small hydrogen ions which may diffuse readily through the polymer structure.

Preferably the reactive component comprises at least one calcium- or strontium-containing compound, most preferably a calcium phosphate or strontium phosphate compound. Preferably there are two different such compounds.

Replacement of calcium by strontium may reduce phosphate solubility and enhance repair, and in some embodiments is particularly preferred.

Preferably at least one of the reactive components should be able to dissolve in water absorbed by the polymer formed by the polymerised/cross-linked compound, and react and precipitate as a less soluble calcium or strontium phosphate species directly within the polymer before it can be fully extracted into any surrounding aqueous environment. Preferably, low level release of calcium promotes surface calcium phosphate precipitation. In some embodiments, the final product is brushite or hydroxyapatite.

The term 'calcium phosphate' or 'calcium phosphate compound' refers to any inorganic compound containing calcium ions ($Ca^{2+}$) and phosphate ions, wherein the phosphate ions may be in the form of, for example, orthophosphates ($PO_4^{3-}$), metaphosphates ($PO_3^{-}$) or pyrophosphates ($P_2O_7^{4-}$) and which may also contain hydrogen or hydroxide ions. The term 'strontium phosphate' or 'strontium phosphate compound' refers to any inorganic compound containing strontium ions ($Sr^{2+}$) and phosphate ions, wherein the phosphate ions may be in the form of, for example, orthophosphates ($PO_4^{3-}$), metaphosphates ($PO_3^{-}$) or pyrophosphates ($P_2O_7^{4-}$) and which may also contain hydrogen or hydroxide ions In addition, other counterions may also be present. For example, calcium or strontium can be partially replaced by sodium or iron to increase or decrease its aqueous solubility respectively. Fluoride ions can also be included to reduce the solubility of the final calcium or strontium phosphates. The calcium or strontium phosphate compounds may also be hydrates or solvates, i.e. may contain solvent molecules within their crystal structure.

Examples of calcium phosphates include, but are not limited to: tricalcium phosphate $Ca_3(PO_4)_2$ (TCP, also called tribasic calcium phosphate—occurs in α and β phases, β-TCP also known as Whitlockite); dicalcium phosphate $CaHPO_4$ (also called calcium monohydrogen phosphate, dicalcium phosphate anhydrous (DCPA) and monetite); dicalcium phosphate dihydrate (DCPD, brushite); calcium dihydrogen phosphate $Ca(H_2PO_4)_2$ (also called monocalcium phosphate); monocalcium phosphate monohydrate (MCPM); calcium pyrophosphate $Ca_2P_2O_7$ (occurs as α, β and γ phases); hydroxyapatite $Ca_{10}(PO_4)_6(OH)_2$; octocalcium phosphate $Ca_8H_2(PO_4)_6.5H_2O$; amorphous calcium phosphate $Ca_3(PO_4)_2.nH_2O$ (ACP); precipitated hydroxyapatite $Ca_{10-x}(HPO_4)_x(PO_4)_{6-x}(OH)_{2-x}$ (PHA) and the like.

In some embodiments, the calcium-containing compound is selected from the list consisting of: α or β tricalcium phosphate (TCP); dicalcium phosphate; dicalcium phosphate dihydrate (brushite); calcium dihydrogen phosphate; monocalcium phosphate monohydrate (MCPM); tetracalcium phosphate; α, β or γ calcium pyrophosphate.

In some embodiments, strontium may partially or fully replace calcium in any one of these phosphates. Strontium is used in various forms as both a drug and in devices for repair of osteoporotic bone, and after bone tumor removal, due to its beneficial effects on bone cells and hydroxyapatite solubility. We propose that its release from the new materials could aid osteoporotic bone repair.

In some preferred embodiments, the reactive components comprise tricalcium phosphate (TCP) and monocalcium phosphate monohydrate (MCPM). In other preferred embodiments the reactive components comprise MCPM and tristrontium phosphate.

In some embodiments, MCPM is mixed with TCP or tristrontium phosphate at a 1:1 weight ratio. Preferably, the reactive components comprise 40-60 wt % MCPM and 40-60 wt % TCP or tristrontium phosphate.

Preferably, the filler comprises about 0-90, 10-90, 10-80, 10-70, 10-60, 10-50, 20-80, 20-70, 20-60, 20-50, 0-80, 0-70, 0-60, 0-50, 0-40, 0-30, 0-20 or about 0-10 wt % reactive component (e.g CaP or SrP). In some embodiments, the reactive component comprises about 10, 15, 20, 25, 30, 40, 50, 60, 70, 80 or 90 wt % of the filler, most preferably 20 wt % of the filler.

In some embodiments, the filler comprises about 10 to 90 wt % reactive component, optionally about 10-20 wt % reactive component.

In some preferred embodiments, the reactive component comprises TCP and MCPM, and comprises 20 wt % of the filler. In further preferred embodiments, the reactive component comprises MCPM and tristrontium phosphate and comprises 20 wt % of the filler. Preferably, the molar ratio of TCP or TSP to MCPM is about 1:1.

In some embodiments, the filler further comprises an "inert" dental glass powder, that is preferably silane-treated to enable interface bonding with methacrylates. In some embodiments, the glass powder comprises about 0-90 wt % of the filler, preferably about 0-20, 0-30, 0-40, 0-50, 0-60, 0-70, 0-80, 10-80, 20-80 wt %, 20-70, 20-60 or 20-50 wt % of the total formulation. In some embodiments, the filler comprises about 0, 10, 20, 30, 40, 50, 60, 65, 70, 75, 80, 85, 90 or 95 wt % glass powder, or any range therein.

Preferably, the silane-treated glass powder is a radiopaque alumino silicate consisting of primarily 5-10 wt % $Al_2O_3$, 65-75 wt % $SiO_2$, and 15-25 wt % BaO. The most commonly used dental glass silane is A174, gamma-methacryloxypropyltrimethoxysilane. Typically this will be added at 1-5 wt % of the glass but may be higher for finer nanoparticles. Alternative inert dental glasses consists of 5-20 wt % $Al_2O_3$, 30-60 wt % $SiO_2$, 5-15 wt % B2O3 and radiopacifying oxides eg BaO, O520, ZnO, $La_2O_3$ or $ZrO_2$ up to about 30 wt %.

Furthermore, alternative silane treated basic glasses (eg those in resin modified glass ionomer cements that can react with acids) could be included. Alternative reactive inorganic fillers could also include those found in mineral trioxide aggregate (MTA or Portland cement). Components of MTA can include tricalcium silicate with dicalcium silicate, tricalcium aluminate, tetracalcium aluminoferrite and calcium sulfate.

In one aspect of the invention, the fluid formulation, e.g. the filler, comprises an active agent. In some embodiments, the active agent is an antibacterial or antibiotic agent or the like. Preferably the filler comprises one, two or more active agents. In some embodiments, the active agent is a cationic polymer, e.g. polylysine. Preferably, the filler comprises between about 0.5 and 10 wt % polylysine.

Examples of antibacterial and antifungal agents include chlorhexidine (e.g. chlorhexidine diacetate), cetyl pyridinium chloride, thymol and the like. Preferably, chlorhexidine is present in formulations for use in tooth applications, e.g. at between about 2 to 10 wt % of the filler.

Examples of suitable antibiotics include gentamicin, tetracycline, oxycycline, minocycline and the like. Preferably, gentamicin is present in formulations for use in bone applications, e.g. at between about 2 to 10 wt % of the filler.

Other active agents may also be present, for example anti-inflammatory agents (prednisolone and ketoprofen and analgesics (morphine, codeine), or agents for the treatment of disease, e.g. bisphosphonates or strontium compounds for osteoporosis. Preferably these active agents are present in the formulation in quantities between 1 and 20 wt %. Additionally, biological molecules such as proteins, DNA, SiRNA or antibacterial phage and the like may be included at lower levels. DNA and other biological molecules may be present at between about 0.01 to about 1 wt % of the filler.

In some embodiments, the filler comprises an active agent selected from one or more of an antibacterial agent, optionally chlorhexidine, cetyl pyridinium chloride or thymol, and an antibiotic, optionally gentamicin, tetracycline, oxycycline or minocycline.

In a preferred embodiment, the filler comprises chlorhexidine or gentamicin.

In some embodiments, the filler comprises about 0.5 to 50 wt % active agent, preferably between about 0.5 to 30, 0.5 to 25, 1-30, 1-25, 1-20 wt % or 1-10 wt % active agent. In some embodiments the filler comprises about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 wt % anti-bacterial agent.

In some embodiments, the filler comprises about 0-20, 0.5-20, 0-10, 0.5-10, 1-20, 1-10 or preferably about 2-10 wt % chlorhexidine (CHX) or gentamicin. Preferably the filler comprises about 0.5, 1, 2, 3, 4, 5, 6, 7, 8, 9, 10, 11, 12, 13, 14, 15, 16, 17, 18, 19 or 20 wt % chlorhexidine or gentamicin.

In some preferred embodiments, the filler comprises PLS and chlorhexidine (CHX) at the wt % levels described herein. Preferably, the filler comprises about 0.5-20 wt % PLS, e.g. about 0.5%, 1%, 2%, 3%, 4%, 5%, 6%, 7%, 8%, 9%, 10%, 15% or 20 by weight, and 0-10 wt % CHX, e.g. 0, 1%, 2%, 3%, 4%, 5%, 6%, 7%, 8%, 9% or 10% by weight. In some embodiments, the filler comprises about 0-10 wt % CHX and 0.5-10 or 0.5-20 wt % PLS. In some embodiments, the filler comprises about 2-10 wt % CHX and about 0.5-10 wt % PLS.

In some preferred embodiments, the filler comprises PLS and gentamicin at the wt % levels described herein. Preferably, the filler comprises about 0.5-20 wt % PLS, e.g. about 0.5%, 1%, 2%, 3%, 4%, 5%, 6%, 7%, 8%, 9%, 10%, 15% or 20 by weight, and 0-10 wt % gentamicin, e.g. 0, 1%, 2%, 3%, 4%, 5%, 6%, 7%, 8%, 9% or 10% by weight. In some embodiments, the filler comprises about 0-10 wt % gentamicin and 0.5-10 or 0.5-20 wt % PLS. In some embodiments, the filler comprises about 2-10 wt % gentamicin and about 0.5-10 wt % PLS.

The materials of the invention are therefore suitable for use as drug or DNA delivery devices, if these active compounds are incorporated into the formulations.

Accordingly a preferred aspect of the present invention provides a method of DNA delivery comprising the steps of:
  i) providing a formulation according to the invention comprising a cationic polymer, e.g. polylysine, and further comprising the desired DNA molecules;
  ii) introducing said formulation into a treatment site;
  iii) curing said formulation to produce a material according to the invention;
  iv) allowing release of the cationic polymer and DNA molecules and formation of polyplexes with enhanced transfection ability.

A further aspect of the invention provides the use of a formulation according to the invention in a method of DNA delivery (or in the preparation of medicament, carrier, or implant for this) for example as described above.

The slow-release of DNA, as can be attained using formulations of the present invention are therefore of great benefit in providing prolonged treatment as well as a constant supply of the DNA in the body to increase the chance of successful and continuing uptake.

In one aspect of the invention, the filler comprises fibres. Fibres will provide material toughening and provide bridging to allow time for "self repair" mechanisms. The fibres may be formed from carbon, glass or any other suitable material. Preferably, the fibres are glass fibres.

In some embodiments, the filler comprises about 0-25, 1-25, 0-10 or 1-10 wt % fibres, e.g. glass fibres. Preferably, the filler comprises about 1, 5, 10, 15, 20 or 25 wt % fibres.

One aspect of the invention provides calcium and/or strontium phosphate cements, e.g. brushite, hydroxyapatite and the like, comprising a cationic polymer, and formulations and methods for the production of said cements.

In some embodiments, the invention provides a process for the production of cement, e.g. brushite, comprising
  i) providing a fluid formulation comprising an aqueous cationic polymer solution and a reactive component selected from one or more of reactive calcium phosphates and reactive strontium phosphates;
  ii) optionally introducing said formulation into a site of use; and
  iii) causing or allowing said reactive calcium or strontium phosphates to react with water to produce brushite comprising the cationic polymer.

A further aspect of the invention provides a fluid formulation for the production of brushite bone cement comprising a cationic polymer, preferably polylysine, and a reactive component.

In some embodiments, a fluid formulation of the invention for the production of brushite comprises a cationic polymer and a filler comprising reactive calcium and/or strontium phosphates, wherein said filler is capable of reaction to produce brushite comprising the cationic polymer.

In some embodiments, the process for the production of brushite comprises
  i) providing a fluid formulation, e.g. as described herein, comprising a cationic polymer and a reactive component selected from one or more of reactive calcium phosphates and reactive strontium phosphates;
  ii) optionally introducing said formulation into a site of use; and
  iii) causing or allowing said reactive calcium or strontium phosphates to react with water to produce brushite comprising the cationic polymer.

In preferred embodiments, the fluid formulation comprises a wt % cationic polymer as described herein, e.g. about 0.1 to 50, 10 to 50 or 10-40 wt % aqueous cationic polymer. In some embodiments, the brushite or fluid formulation comprises about 1, 5, 10, 20, 30, 40 or 50 wt % aqueous cationic polymer or any range therein. In a preferred embodiment, the cationic polymer is present in a fluid phase, e.g. an aqueous phase, of the fluid formulation, e.g. as aqueous cationic polymer or polylysine. In a preferred embodiment, the cationic polymer is polylysine and the ratio of reactive filler to aqueous phase is 3:1 or 4:1.

In some embodiments, the reactive component comprises MCPM and TCP, preferably equimolar MCPM and TCP. In some embodiments, the reactive component comprises MCPM and tristrontium phosphate, preferably equimolar MCPM and tristrontium phosphate. In some embodiments, the reactive component is as described herein.

Most preferably, the brushite or fluid formulation comprises MCPM, TCP and polylysine.

In some embodiments, the fluid formulation may comprise a setting retardant, e.g. citric acid, preferably at between about 400 and 800 mM in the aqueous phase of the cement. As described herein, a setting retardant may not be required in the presence of polylysine. Therefore one aspect of the invention provides polylysine for use as a setting retardant in the production of brushite. In this case the fluids produced can have improved handling properties. Specifically, they can be more cohesive. Furthermore, replacement of the citric acid could improve cell compatibility.

In some embodiments, the fluid formulation may comprise a polymeric setting retardant, e.g. polyacrylic acid in addition or replacing citric acid. As described herein, polyacrylic acid can interact with cationic antibacterial chlorhexidine within a brushite cement and thereby enhance flexural strength. Polylysine should interact more strongly with polyacrylic acid. Therefore one aspect of the invention proposes use of polylysine with polyacrylic acid containing brushite cements to enhance both mechanical and antibacterial properties.

In preferred embodiments of the present invention, the compounds capable of (further) polymerising and/or cross-linking to form a solid polymeric matrix (the polymerisable/cross-linkable compound) may be one or more monomers, which can be polymerised in situ. Alternatively, some fluid polymers, in particular short chain polymers (oligomers) with methacrylate chain ends, which are also capable of further polymerisation may be used.

Furthermore polymers with acid groups may be able to crosslink through neutralisation (e.g. carboxylic acid groups on polyacrylic acid when converted to calcium polyacrylate will be crosslinked through the divalent calcium ions.

The term polymer is well known in the art, and refers to a macromolecule made up of multiple repeating units (monomers). Polymers may be formed of more than one type of monomer, in which case they can also be referred to as co-polymers. Short-chain polymers of relatively low molecular weight, made up of a finite number of monomer units (for example, from 5 to 1000 units), may also be referred to as oligomers. In the context of this application, the term polymer expressly includes both short-chain (oligomers) and long-chain polymers. In some embodiments of the present invention, it is preferred that the polymerisable fluid primarily consists of larger compounds such as oligomers or high molecular weight monomers to reduce heat and shrinkage of polymerisation.

Although the ensuing discussion is focussed primarily on the use of high molecular weight monomers and oligomeric compounds, in the light of this disclosure it will be readily understood by one skilled in the art that the principles of the invention apply mutatis mutandis to the use of smaller polymerisable monomers (eg methylmethacrylate) and crosslinkable polymers. Indeed, in some applications low levels of small monomers can be beneficial in improving handling and wetting of surfaces for greater adhesion. Additionally in other formulations the monomers may be pre-polymerised but then made fluid through the use of solvents or through dispersion/dissolution in other monomers.

In some embodiments, for example wherein the formulation is for production of a material selected from a glass ionomer cement, a resin modified glass ionomer cement, surface coating or compomer, at least one of the polymerisable/cross-linkable compounds is a polyacid, e.g. a polyalkenoic acid. Preferably, the polyacid is polyacrylic acid (PAA). In some embodiments, the PAA has a molecular weight of between about 1,000 and 10,000 g/mol, preferably about 2000 g/mol.

Monomers capable of cross-linking by either chemical or physical processes, which may be suitable for use in the invention, are known in the art.

In some embodiments, the at least one compound capable of polymerisation and/or cross-linking comprises a polymerisable methacrylate moiety, and is optionally selected from UDMA, PPGDMA, BISGMA, methylmethacrylate, acrylic acid, HEMA, TEGDMA, polyacid, e.g. PAA, and the like.

Non Degradable Formulations

Monomers/oligomers that are considered primarily non degradable include methacrylates in bone and dental materials, composites and adhesives. These include urethane dimethacrylate (UDMA), triethylene glycol dimethacrylate (TEGDMA), bisphenol A glycidyl (BISGMA), 4-methacryloxy-ethyl trimellitate anhydride (4-META), HEMA phosphate (2-hydroxyethylmethacrylate add phosphate), Pyromellitic Dimethacrylate (PMDM), Methylmethacrylate, hydroxyethylmethacrylate (HEMA) and the like e.g. as described in reference [24], incorporated herein by reference. Alternative larger monomers include polypropylene glycol dimethacrylate (PPGDMA).

In some embodiments, the monomers may be pre-polymerised. For example, pre-polymerised PMMA beads are used in many PMMA bone cements. There must be sufficient solvent and/or fluid monomer, however, to ensure polymer dissolution/injectability.

In some embodiments, the fluid formulation comprises a fluid phase comprising more than one compound capable of polymerisation and/or cross-linking. Preferably, the fluid phase comprises PPGDMA and UDMA. The low glass transition temperature (Tg) of polypropylene glycol (PPG) results in a composite that is flexible instead of brittle, as shown herein. Most preferably, the fluid phase comprises between about 20-80 wt % PPGDMA and about 20-80 wt % UDMA, even more preferably about 23-70 wt % PPGDMA and about 23-70 wt % UDMA. In some embodiments, the fluid phase may further include diluents, for example HEMA, preferably at about 7 wt %.

In some embodiments, the fluid formulation comprises TEGDMA and UDMA. Most preferably, the fluid phase comprises between about 10-50 wt % TEGDMA and about 50-90 wt % UDMA, even more preferably about 20-30 wt % TEGDMA and about 60-80 wt % UDMA. In some embodiments, the fluid phase may further include other diluents, for example HEMA, preferably at about 5 wt %. Adhesive monomers such as 4 META, PMDM, HEMA phosphate at 2-10 wt % may also be beneficial to promote bonding to calcium phosphate species.

In some applications it is preferred that the resultant polymer is non-degradable. The term "non-degradable" refers to materials which do not significantly decompose or erode over time. Depending on their application, some decomposition or erosion (for example due to mechanical wear) of the material of the invention may be inevitable over long periods of time. Additionally, in the proposed formulations it is required that active agents are released to provide beneficial surrounding effects. Preferably, however, the non-degradable polymer surrounding the active fillers should not significantly decompose or erode over a period of at least 1 year, more preferably at least 2, 3, 4, 5, 10 or 20 years.

Applications where a non-degradable polymer is preferable are described below and include restorative dentistry e.g. tooth restoration, vertebroplasty (fixation of vertebral osteoporotic fractures), cements for total hip or knee replacement, and replacement of metal screws for osteoporotic hip fractures. In these applications it will be appreciated that it is acceptable that some calcium phosphate species may leach from the set material provided there is not an unacceptable decline in material strength. This leached material may remineralise the surrounding tooth structure reducing its susceptibility to recurrent caries infection. It may also fill gaps between the tooth and restoration to prevent leakage of bacteria from the surface of the tooth. In bone applications the leached components could aid remineralisation and repair of surrounding bone.

In some embodiments of the invention, it is preferred that the polymers are capable of chemical cross-linking, i.e. of forming covalent bonds between chains. This is achieved with dimethacrylate monomers such as UDMA, TEGDMA and PPGDMA particularly when methacrylate conversion exceeds 50%.

Covalent bonds may be formed by reaction of radicals generated, for example, by irradiation with UV or visible light, in the presence of an initiator and activator compounds, or by means of a chemical cure system. Such initiator and activator compounds include (i) camphorquinone (CQ), benzoyl peroxide (BP) or the like, together with (ii) dimethylparatoluidine (DMPT) or N-tolylglycine glycidyl methacrylate (NTGGMA) or the like. In a preferred embodiment, the activator is NTGGMA.

In some embodiments of the invention, these compounds are present at about 0.25-2 wt % of the compound capable of polymerisation and/or cross-linking, preferably about 1 wt % of the compound capable of polymerisation and/or cross-linking. In a preferred embodiment, the initiator and activator compounds are BP and NTGGMA, wherein NTGGMA is about 0.75 wt % of the compound capable of polymerisation and/or cross-linking, and BP is about 0.75 wt % of the compound capable of polymerisation and/or cross-linking.

Alternative initiators include but are not limited to 2-(N, N-dimethylamino)ethyl methacrylate (DMAEMA), benzoin, Irgacure 651®, phenylpropanedione (PPD), monoacylphosphate oxide (Lucirin TPO), bisacylphosphine oxide (Irgacure 819), benzyldimethyl ketal (Igracure 651) These are also preferably at concentrations between 0.25 and 2 wt % of the fluid phase In other compounds capable of polymerisation and/or cross-linking, additional acidic groups such as carboxylic or phosphoric acid are included (eg 4 META, NTGGMA, PMDM, HEMA phosphate, acrylic acid, maleic acid, itaconic acid and phosphoric acid equivalents). These give interaction between the restorative material/adhesive and hydroxyapatite in the surrounding tooth structure. Such acidic chemical groups could also provide greater interaction between the compounds capable of polymerisation and/or cross-linking, and calcium phosphate fillers thereby raising mechanical properties. The presence of the polyacids may also aid transformation of brushite to less soluble hydroxyapatite. A wide range of such compounds capable of polymerisation and/or cross-linking are present in current dental adhesives.

In some embodiments polymerisation inhibitors, e.g. monomethyl ether hydroquinone (MEHQ), may also be present. Other stabilisers/inhibitors may include hydroxyquinone or butylated hydroxytolune (BHT) (all preferably at 0.005 to 0.05 wt %).

In some embodiments, the formulation, i.e. the fluid phase of the formulation, further comprises one or more of the following additives: a polymerisation initiator; diluent monomers; hydroxyquinone; an active agent.

Degradable Monomers and Polymers

In some bone applications where high cement strength is less of an issue (eg as a bone filler after tumour removal or infection control or jaw augmentation after periodontal disease or tooth removal) it is preferred that the formation is degradable to enable full bone repair. This can be achieved using water as the fluid phase to form brushite cements or through use of degradable monomers/oligomers. The term 'degradable' refers to materials which decompose or erode over time to produce molecules, which are soluble in the surrounding medium. Preferably this degradation occurs over a timescale of a few weeks (for shorter term drug delivery devices, for example for periodontal treatment) or months (for longer term drug release and bone repair). If this decomposition occurs in biological conditions, such as inside the body, and on a biologically relevant timescale, the materials may be referred to as 'bio-degradable'.

Degradable oligomers/monomers capable of chemical cross-linking include, but are not limited to: poly(ether-co-esters) (in particular poly(lactide-co-propylene glycol-co-lactide)) with (meth)acrylate groups on the chain ends; polyanhydrides, and polypropylene fumarates combined with other cross-linking dimethacrylates [9-12]. In these preferred embodiments as well as non-degradable dental restorative materials the cross-linking generally involves acrylate or methacrylate end groups on the monomer/polymer chains.

Further examples of polymers which may be suitable for use in this invention include, but are not limited to, polyesters (such as polylactide, polyglycolide, polycaprolactone), polycyanoacrylates, polyacrylic acid, polyacrylamide, polyorthoesters, natural polymers such as hydroxybutyric acid, cellulose, chitosan, collagen and co-polymers thereof.

Preferred cross-linkable degradable polymers for use in the formulations of the invention include short-chain poly (ether esters), polyanhydrides and polypropylene fumarates. Advantageously, these units may comprise methacrylate groups on the chain ends which enable chemical cross-linking of the chains.

Preferably the cross-linkable degradable polymers used in the present invention are short chain methacrylate capped poly(ether-co-esters). The cross-linkable polymers may have the general formula (I):

Formula (I)

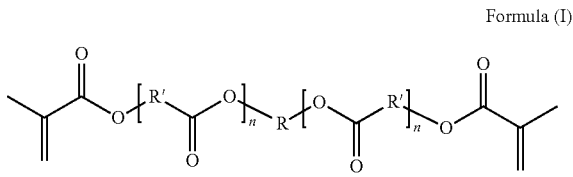

wherein R' for example may be straight or branched alkyl having 1 to 10 carbon atoms, preferably $CH_2$ (glycolide), $CH(CH_3)$ (lactide) and/or $(CH_2)_5$ (caprolactone).

To increase or decrease polymer degradation rates, lactide groups may be partially replaced by caprolactone and glycolide groups, respectively. The choice of R' will therefore depend upon the specific application and the required rate of degradation. Generally, although not exclusively, with polyesters, as the ratio of carbon to oxygen atoms increases hydrophobicity is raised and degradation rate decreased and it will be appreciated that such changes may be tested and optimised without undue burden in the light of the present disclosure.

If the ester group is replaced simply by C=O, polyanhydrides are then formed upon polymerisation of the methacrylate group. In polypropylene fumarates degradable 0020=0002 chemical groups are present in addition or instead of methacrylate groups. The polyesters are, however, preferable because the high reactivity of the anhydride group can make purification less easy and the sterically hindered fumarate groups can be slower to polymerise that methacrylate end groups.

R for example may be poly(propylene)glycol, poly(ethylene)glycol or poly(propylene co ethylene)glycol. With longer, more hydrophobic, chains degradation rate can be reduced. R may also be a straight chain hydrocarbon having 2 to 6 carbon atoms (derived from the corresponding terminal diols e.g. 1,2-ethanediol and 1,6-hexanediol), In principle, however, any molecule with alcohol ends may also be used to form a wide range of monomers.

Those skilled in the art will be readily able to provide appropriate polymers for use in the invention disclosed herein without undue burden and using known methods. For example more branched polymer structures (e.g. containing 3 and 4 methacrylate groups) may be provided using glycerol $(HC(OH)(CH_2OH)_2)$, pentaerythritol $(C(CHOH)_4$ or polyvinyl alcohol in place of R.

Particularly preferable are poly(lactide-co-propylene glycol-co-lactide)dimethacrylates. Most preferably these are triblock dimethacrylates with a central polypropylene glycol (PPG) section of molecular weight 400 to 2000 g/mol (equivalent to 7 and 34 propylene glycol units respectively), capped both ends with lactide segments (LA) with between 2 and 8 lactic acid units (equivalent to molecular weights of 144 to 576 g/mol) and then methacrylate groups. PPGnLAmDMA indicates a dimethacrylate with a total of n 'PG' and 2m 'LA' units, respectively.

Combination of PPGnLAmDMA with reactive calcium phosphate fillers has been discussed in references [25-29], incorporated herein by reference. These papers also describe additional components (eg initiators, activators, inhibitors, diluents) required within the formulations. These are also covered above in more detail with the non degradable monomers. The formulations described in references [25-29] are specifically incorporated herein by reference. Thus some embodiments of the invention relate to the formulations described in references [25-29] further comprising a cationic polymer, e.g. polylysine, as described herein. With the further addition of a cationic polymer these formulations are anticipated to have many of the improvements in properties discussed above for non degradable formulations. In some embodiments, these formulations further comprise DNA. With added DNA they could additionally provide prolonged transfection of cells.

Other formulations, without reactive CaP fillers for which addition of polylysine would provide beneficial antibacterial properties are provided herein. These include formulations for the production of more conventional dental composites, compomers, RMGICs and GICs. For compomers, RMGICs and GICs, further advantages would be encouragement of greater water sorption from the surroundings. This could enable greater polyacid/base reactions within the material enhancing properties such as expansion to compensate polymerisation shrinkage, fluoride release and adhesion. This would be particularly beneficial with the compomers. These contain no water initially to allow polyacid/glass reaction. Furthermore, the hydrophobicity of compomers prevents high water sorption. Reaction between acid groups and basic glass in the formulations is therefore limited. Addition of a cationic polymer, e.g. polylysine, would overcome this problem. We additionally, anticipate that replacement of some of the water in RMGICs and GICs by polylysine could improve other mechanical properties.

Materials for Bone and Tooth Repair

Another aspect of the present invention provides a material formed from a fluid formulation according to the invention comprising a cationic polymer, the material comprising:
1) a polymer matrix, and
(2) a cationic polymer distributed in said matrix.

Preferably, the material is a composite, compomer, glass ionomer cement, resin modified glass ionomer cement or adhesive.

In some embodiments, polymerisation/cross-linking of the polymerisable/cross-linkable compound produces the polymer matrix. The polymer matrix therefore incorporates the particles of the filler within said matrix. These particles may preferably be in the range of 0.5 to 200 μm in size. Preferably the material is formed by cross-linking of a preferred fluid formulation as described above, wherein the polymerisable/cross-linkable compound is a monomer, polymer or oligomer.

Such materials may be used, for example, as fillers, scaffolds, or membranes in bone or other tissue repair, cements or adhesives in fixing bio-implants, restorative dental or other medical composites per se, or to release or provide actives such as bacteriocides (either in these contexts, or as preparations solely for that purpose).

In some embodiments, the material further comprises a solid filler formed by reaction of a reactive component as described herein.

A composite material is a complex material, in which two or more distinct, structurally complementary substances, especially glasses or polymers, combine to produce structural or functional properties which differ from those of any individual component.

In the context of this application, the term 'composite material' refers to a material formed from setting or curing of a fluid formulation, such as a formulation according to the invention, comprising a polymer matrix, preferably a cross-linked polymer matrix, and dispersed solid particles. In some embodiments, the solid particles may be made up of the water-consuming reactive component described above, of the material produced when said reactive component has reacted with water, or of a mixture comprising these species. Preferably, the reactive component is between about 0-90 wt % of the composite material, e.g. about 0, 10, 15, 20, 25, 30, 40, 50, 60, 70, 80 or 90 wt % of the composite material or any range therein. Preferred reactive component species, and the materials formed therefrom, are discussed above.

As described above for the fluid formulations, the formation of the polymer matrix may be by either chemical or physical mechanisms, including cross-linking. Preferred cross-linkable polymers, from which the polymer matrix may be formed, are discussed above.

Preferably, the solid particles of the material are initially well distributed throughout the polymer matrix.

Raising homogeneity via reaction of the filler particles is potentially advantageous for many reasons, primarily because the weak abrupt interfacial region between the polymer and filler is lost. This may improve mechanical and wear characteristics. For degradable formulations the inorganic and polymer phases are also more likely to dissolve/degrade together if the organic and inorganic phases are interacting at the molecular level rather than purely at polymer particle interfaces. Addition of filler can also provide a means to alter the rate of polymer degradation (in embodiments wherein the polymer is degradable). Further, its simultaneous release with any acidic degradation products (which are produced during degradation of many biomedical degradable polymers) may buffer the surroundings and reduce any acid irritant effects. Such buffers may also prevent bulk catastrophic degradation of polymers which can occur with build up of acidic products in the material cores.

Properties of the non degradable [30-31] and degradable composites [25-29] improved through reactive calcium phosphate addition have been described in these references, incorporated herein by reference. Examples of mechanical properties which may be improved by the present invention, and in particular the use of cationic polymers as described herein, include surface hardness, elasticity, dynamic modulus, compressive and flexural strength and wear resistance. Other properties which may be improved in the material of the invention, compared to polymerised/cross-linked compounds in the absence of fillers, include cell compatibility/attachment, a reduction in the heat or shrinkage generated during polymerisation/cross-linking, due to the lower volume fraction of the polymer, and degradation, which may be easier to control through variations in filler loading.

Advantageously, the properties of the material may be controlled by altering the properties of the polymerisable/cross-linkable compound, or other variables, such as the amount and identity of the filler, may also affect the final mechanical properties of the material.

As will be appreciated by those in the art, the choice of preferred filler may vary depending on the type of polymerisable/cross-linkable compound used, and vice versa. Depending on the required properties for a particular material, different combinations of the preferences laid out above may be suitable. The optimum choice and amount of filler may also be dependent on the degree of cross-linking of the polymer, for example. Increasing cross-linking, for example by reducing the length of polymer chains in the initial formulation, may reduce the amount of water sorption.

Control of mechanical properties is particularly useful in the development of materials for use in both tooth and bone repair applications, where properties close to those of real tissue are optimal [8,9].

It is preferable that the strength of the material (the stress at which the material breaks) is as high as possible so that it may be used in weight-bearing bone fixation (eg in the lower body) or to fix teeth where occlusal load may be high and in filling of regions where stresses may be more minimal. Bone and tooth strengths are dependent upon age and health of a subject as well as type (cortical versus cancellous and enamel versus dentine) and location but can be over 150 MPa in both compression and tension.

In addition the modulus of a bone or tooth-fixation material and its response to any forces should preferably be comparable to that of the surrounding tissue. As described herein, cationic polymers, e.g. polylysine, can be used to modulate the modulus to achieve the desired effect. For elastic solids modulus may be defined as stress divided by strain. Stress is the force per unit area and strain the extension per unit length. Calcium phosphate cements are generally brittle with high modulus and a low level of strain at break point but polymers can be much more flexible and extend much further before break. Polymers are also viscoelastic in that modulus can vary with time and flow can occur under a continuous stress as occurs with a liquid. This viscoelastic mechanical behaviour can be monitored using dynamic mechanical analysis which provides both the storage modulus (which can be identified with the elastic nature of the material) and the loss modulus (which quantifies the fluid nature of the polymer).

The modulus of bone and tooth is highly variable but primarily dependent upon tissue porosity and the relative levels of collagen, hydroxyapatite and water. Cancellous bone and dentine have higher collagen and water content and so lower modulus than cortical bone and tooth enamel. Their viscoelastic behaviour in particular is more likely therefore to be matched using a combination of calcium phosphate and polymers rather than either individually. The modulus of bone, or of any material, is also dependant upon the exact mode of measurement, which can vary widely. Tooth and bone typically has an elastic or storage modulus between 0.2 and 20 GPa.

In preferred embodiments of the present invention, the mechanical properties of the material are closer to those of real tooth and bone, than those of the polymerised/cross-linked compound in the absence of filler. More preferably, the mechanical properties of the materials after reaction of the fillers with the absorbed water are closer to those of tooth and bone than before this reaction occurs. In more preferred embodiments, the mechanical properties of the materials, at least in the early stages of material placement (i.e. within a few hours after injecting and setting/curing) are a close match to those of tooth and bone.

Mechanical properties of bone may include, but are not limited to:
Elastic modulus (E):
  Low strain ~10-20 GPa
  High strain ~10 GPa
Dynamic modulus
  Storage E' ~8 GPa
  Loss E" ~0.2 GPa
Strength
  Compressive 5-10 MPa (cancellous) 130-220 MPa (cortical)
  Tensile 5-10 MPa (cancellous) 80-150 MPa (cortical)
[see refs 4,8, 10-12]
  Trabecular bone may have an elastic modulus of <3 GPa [32].

In some embodiments it may be preferable that the materials of the invention are degradable. More preferably this degradation occurs from the surface of the material, in a controlled manner. Preferably the inorganic particles and the polymeric matrix degrade at approximately the same rate. This may in preferred embodiments be readily controllable over periods ranging from days to months for different applications. For periodontal treatment, for example, the material should degrade in about 6 weeks but for large bone defects the material would need to remain in place for much longer but preferably become porous and permeable to cells with time, so as to act as a scaffold for new bone formation. If the degradation products of the polymer are acidic (for example, polylactides degrade to release lactic acid) it is preferred that the degradation products of the inorganic particles are basic, and create a buffering effect to neutralise these acidic products.

In other embodiments it may be preferable that the materials of the invention are non-degradable. The term "non-degradable" refers to materials which do not significantly decompose or erode over time. Some decomposition or erosion (for example due to mechanical wear) may be inevitable over long periods of time. Preferably, a non-degradable material does not significantly decompose or erode over a period of at least 1 year, more preferably at least 2, 3, 4, 5, 10 or 20 years.

Applications where a non-degradable material is preferable include restorative dentistry e.g. tooth restoration, fissure sealants and adhesives for crowns and orthodontic brackets. In bone repair non degradable formulations could be used for vertebroplasty, total hip and knee replacement surgeries, screw augmentation and preformed screw replacement. Non degradable bone cements are particularly required for older patients if the bone is osteoporotic, for revision surgeries when a hip or knee implant must be replaced or after complications arising with infection.

As described herein, one aspect of the invention relates to a fluid formulation comprising:
(1) at least one compound capable of polymerising and/or cross-linking to form a solid polymer matrix,
(2) a cationic polymer, and
(3) optionally a filler.

Preferably, the fluid formulation is as described herein.

Optionally, the filler further comprises a reactive component, wherein said filler is capable of reaction within the solid polymer matrix with water to produce a solid filler compound comprising the cationic polymer.

In some embodiments, the cationic polymer is polylysine, and the filler comprises 0.5 to 10 wt % polylysine, 0 to 10 wt % chlorhexidine or gentamicin, 0 to 50 wt % reactive component, 0 to 25 wt % glass fibres and 0 to 80 wt % glass powder. Preferably, the reactive component comprises monocalcium phosphate monohydrate and one of tricalcium phosphate and tristrontium phosphate. Preferably, the filler comprises 10 wt % polylysine, 10 wt % chlorhexidine, 10 wt % tricalcium phosphate, 10 wt % monocalcium phosphate monohydrate and 60 wt % glass powder. In some embodiments, the fluid formulation comprises 70 to 90 wt % filler.

Different applications will require different amounts and ratios of various components. Certain preferred embodiments are discussed below.

Non-Degradable Dental Composites, Base Restorative Materials and Adhesives

Dental composite (e.g. Z250, Gradia) restorative pastes consist of hydrophobic dimethacrylates (e.g. BISGMA, TEGDMA and UDMA) filled with about 80 wt % inorganic particles. After placement in a tooth cavity they set in seconds via blue light activated free radical polymerisation. Current composites are bonded to the tooth using adhesives. This bonding enhances damaged tissue stability. Composite shrinkage during polymerisation, thermal changes, cyclic loading and composite stiffness, however, can all cause high stress on, and damage to, the bond. Micro gap formation and bacterial penetration between the tooth and restoration then occurs. As composites have no antibacterial action, re-infection and continuing demineralisation subsequently occurs. The problem is exacerbated by enzymatic degradation of both demineralised collagen and composite adhesive. Shrinkage effects can be reduced by placing the composite in layers but this further complicates tooth restoration procedures.

One aspect of the invention provides a fluid formulation for use in a process as described herein for production of a composite material, e.g. a non-degradable dental composite, base restorative material and/or adhesive. The fluid formulation comprises a fluid phase and a filler, wherein the fluid phase comprises about 20 wt % to about 80 wt %, and the filler comprises about 80 wt % to about 20 wt %.

In this aspect, the filler comprises (i) about 0.5 to about 10 wt % cationic polymer, e.g. polylysine; (ii) about 2 to about 10 wt % active agent, e.g. chlorhexidine; (iii) about 10 to about 90 wt % reactive component, e.g. a 1:1 molar ratio of (a) MCPM and (b) tristrontium phosphate and/or tricalcium phosphate; (iv) about 0 to about 87 wt % radiopaque glass powder; and (v) about 0 to about 20 wt % glass fibres.

The fluid formulation and composite material produced therefrom provides a number of advantages over the prior art, as described herein. For example, higher polymerisation reduces toxicity. Enhanced water sorption compensates shrinkage during setting. Enhanced active agent, e.g. chlorhexidine, release reduces recurrent caries beneath restoration. Enhanced water sorption promotes reactive component reaction. Greater HA layer formation enhances natural repair. The cationic polymer, e.g. polylysine, in HA surface confers antibacterial activity, makes it more dentine like, and promotes "self-repair". Greater self adhesion simplifies placement and reduces bond failure. Antibacterial and remineralising action enables reduced tissue removal. Greater toughness prevents crack propagation and fracture. Further, the formulation is compatible with dual cure (light and chemical) for when light exposure is difficult.

In some embodiments, the fluid formulation is for use in adult dental cavity restoration. The filler comprises (i) about 1 wt % polylysine; (ii) about 2 wt % chlorhexidine; (iii) about 10 wt % of a 1:1 molar ratio of (a) MCPM and (b)tristrontium phosphate and/or tricalcium phosphate; and (iv) about 87 wt % radiopaque glass powder. The fluid formulation comprises about 80 wt % filler and about 20 wt % fluid phase. This formulation provides a stronger and more aesthetic material, which is desirable for this application.

In some embodiments, the fluid formulation is for use in child dental cavity restoration. The filler comprises (i) about 2 wt % polylysine; (ii) about 5 wt % chlorhexidine; (iii) about 20 wt % of a 1:1 molar ratio of (a) MCPM and (b)tristrontium phosphate and/or tricalcium phosphate; (iv) about 53 wt % radiopaque glass powder; and (v) about 20 wt % glass fibres. The fluid formulation comprises about 80 wt % filler and about 20 wt % fluid phase. This formulation provides a tough material resistant to bacteria, desirable as a child's tooth is primarily dentine and may have a greater bacterial load.

In some embodiments, the fluid formulation is for use in endodontic restoration or base restoration. The filler comprises (i) about 5 wt % polylysine; (ii) about 10 wt % chlorhexidine; (iii) about 30 wt % of a 1:1 molar ratio of (a)

MCPM and (b) tristrontium phosphate and/or tricalcium phosphate; (iv) about 35 wt % radiopaque glass powder; and (v) about 20 wt % glass fibres. The fluid formulation comprises about 50 wt % filler and about 50 wt % fluid phase. This formulation provides increased flexibility and antibacterial action, as it replaces dentine.

In some embodiments, the fluid formulation is for use as a fissure sealant, surface coating or as an orthodontic bracket adhesive. The filler comprises (i) about 10 wt % polylysine; (ii) about 4 wt % chlorhexidine; and (iii) about 86 wt % of a 1:1 molar ratio of (a) MCPM and (b) tristrontium phosphate and/or tricalcium phosphate. The fluid formulation comprises about 50 wt % filler and about 50 wt % fluid phase. For these applications, strength is less important than remineralising and antibacterial action. Fluidity enables good bonding to dentine and/or enamel.

In some embodiments, the fluid formulation is for use as a post or crown adhesive. The filler comprises (i) about 10 wt % polylysine; (ii) about 4 wt % chlorhexidine; and (iii) about 80 wt % of a 1:1 molar ratio of (a) MCPM and (b) tristrontium phosphate and/or tricalcium phosphate. The fluid formulation comprises about 20 wt % filler and about 80 wt % fluid phase. This formulation provides increased remineralising and antibacterial action, which is desired due to difficulty in tooth cleaning, and increased fluidity to provide good bonding to (e.g. acid-etched) enamel.

The fluid phase in the above embodiments comprises at least one compound capable of polymerisation and/or cross-linking, as described herein. Preferably, the fluid phase comprises (i) about 60 to about 75 wt % UDMA; (ii) about 20 to about 30 wt % TEDGMA or PPGDMA; (iii) about 1 to about 10 wt % 4META or PMDM; (iv) about 0.25 to about 2 wt % CQ and/or BP; (v) about 0.25 wt % to about 2 wt % DMPT or NTGGMA; and (vi) about 100 to about 1000 ppm polymerisation inhibitor, e.g. MEHQ. Most preferably, the fluid phase comprises (i) about 68 wt % UDMA; (ii) about 25 wt % TEDGMA or PPGDMA; (iii) about 5 wt % 4META or PMDM; (iv) about 1 wt % CQ and/or 0.25 to about 2 wt % BP; (v) about 0.25 wt % to about 2 wt % DMPT or NTGGMA; and (vi) about 100 to about 1000 ppm polymerisation inhibitor, e.g. MEHQ One optimised dental composite (termed 'F1' in the Examples below) comprises reactive calcium and strontium phosphates (CaSrP) in addition to polylysine (PLS). The formulation F1 comprises a fluid phase:
(i), (ii) a dental monomer phase UDMA/TEGDMA 3/1 with
(iii) 5% 4META and light activated polymerisation initiators.

This liquid was combined with 80 wt % powder. The powder consisted of
(iv) a silanated barium alumino silicate dental glass,
(v) polylysine (PLS, 2.5%),
(vi) tristrontium phosphate (15%) and
(vii) MCPM (10%).

A further dental composite material used in the Examples below comprises the following formula in the monomer (liquid) phase:
(i), (ii) UDMA: 72 wt. %; PPGDMA: 24 wt. %
(iii) 4 META: 3 wt. % and CQ: 1 wt. % And in the powder phase either:

| Formula A: | Glass: | 89 wt. % (1:3:6 nano:0.7:7) |
| | CaP: | 10 wt. % (1:1 MCPM:TCP) |
| | Polylysine: | 1 wt. % |
| Or: | | |
| Formula C: | Glass: | 78 wt. % (1:3:6 nano:0.7:7 μm) |
| | CaP: | 20 wt. % (1:1 MCPM:TCP) |
| | Polylysine: | 2 wt. % |

Non-Degradable PMMA Bone Cements or Bone Composite Materials

Polymethylmethacrylate (PMMA) bone cements (e.g. Palacos and Simplex) are extensively used with metal implants. They are additionally used without metal components to fix vertebra via minimally invasive vertebroplasty. PMMA can also be combined with antibiotics (e.g. gentamicin) to treat or prevent infection [16]. Typical PMMA cement components include methyl methacrylate liquid (MMA) with dimethylparatoluidine (DMPT) activator. Upon mixing with a powder containing poly(methyl methacylate co styrene) beads, barium sulphate radiopacifier, gentamicin antibiotic and benzoyl peroxide (BP) initiator, MMA polymerises and sets the cement. Problems, however, can include high MMA volatility, toxicity and heat generation upon polymerisation due to low monomer molecular weight (100 g/mol) and therefore high double bond concentrations. Monomer conversion can also be slow and incomplete at body temperature. Theatre mixing of powder and liquid may also reduce sterility and material reproducibility. PMMA has only moderate strength but this is about 8% of its modulus. PMMA bonding to bone is limited. With low antibiotic incorporation some early surface release is achieved. Higher drug addition is required to effectively treat osteomyelitis, but this reduces strength.

Bone composites (e.g. Cortoss and Comp06) were developed from dental composite restoratives and are currently used for vertebroplasty [17]. They consist of high molecular weight base cross-linkable/polymerisable compounds (e.g. BISGMA) with lower viscosity diluents (e.g. TEGDMA). These are combined with about 70 wt % radiopaque, silane treated calcium and barium silicate glasses. These composites are supplied as two pastes in double barrelled syringes with automatic mixing tips that enable direct in vivo injection. Preventing surgeon contact upon mixing reduces the possibility of infections, however the current aseptic methods required for sterilisation are costly.

Bone composites have the advantage that polymerisation kinetics and paste viscosities are easier to control than with PMMA. Furthermore, as the cross-linkable/polymerisable compounds are dimethacrylates, less than 100% conversion is required to bond all of the compound. A problem, however, is the greater aqueous solubility and slower conversion of TEGDMA compared with BISGMA. This may lead to TEGDMA release from the set cement which would adversely affect cell compatibility. High BISGMA level and molecular weight does significantly reduce heat generation and shrinkage compared with PMMA. Cortoss strength is initially comparable with that of PMMA but it can decline substantially over a few weeks in water. Unfortunately, initial Cortoss modulus is higher than that of PMMA and the material brittle rather than tough and resilient. Production of hydroxyapatite can advantageously occur on set Cortoss and may improve long term bone bonding. The amount of hydroxyapatite is limited, however, and can take weeks to form. Furthermore, antibacterial agents are not currently included in commercial bone composites. Given their similarity with dental composites, however, antibiotic release percentage is predicted to be very low.

A further aspect of the invention provides a fluid formulation for use in a process as described herein for production of a composite material, e.g. a non-degradable PMMA bone cement or bone composite material. The fluid formulation comprises a fluid phase and a filler, wherein the fluid phase comprises about 20 wt % and the filler comprises about 80 wt %.

In this aspect, the filler comprises (i) about 1 to about 5 wt % cationic polymer, e.g. polylysine; (ii) about 5 to about 10 wt % active agent, e.g. gentamicin; (iii) about 10 to about 25 wt % reactive component, e.g. a 1:1 molar ratio of (a) MCPM and (b) tristrontium phosphate and/or tricalcium phosphate; (iv) about 40 to about 65 wt % radiopaque glass powder; and (v) about 20 wt % glass fibres.

The fluid formulation and composite material produced therefrom provides a number of advantages over the prior art, as described herein. For example, higher polymerisation reduces set material toxicity. Enhanced water sorption compensates shrinkage during set. Enhanced active agent, e.g. gentamicin, release reduces e.g. infection probability. Enhanced water sorption promotes reactive component reaction. Greater HA layer formation enhances oseointegration and surrounding bone repair. Strontium release enhances bone forming osteoblast action, and reduces osteoclast bone resorption.

In some embodiments, the fluid formulation is for use in preformed bone screws to replace metal. The filler comprises (i) about 1 wt % polylysine; (ii) about 5 wt % gentamicin; (iii) about 10 wt % of a 1:1 molar ratio of (a) MCPM and (b) tristrontium phosphate and/or tricalcium phosphate; (iv) about 64 wt % radiopaque glass powder; and (v) about 20 wt % glass fibres. This formulation provides high strength in addition to the other benefits described herein.

In some embodiments, the fluid formulation is for use in cement for hip and knee implant fixation and screw augmentation. The filler comprises (i) about 2.5 wt % polylysine; (ii) about 5 wt % gentamicin; (iii) about 12.5 wt % of a 1:1 molar ratio of (a) MCPM and (b) tristrontium phosphate and/or tricalcium phosphate; (iv) about 60 wt % radiopaque glass powder; and (v) about 20 wt % glass fibres. This formulation provides lower modulus, in addition to the other benefits described herein.

In some embodiments, the fluid formulation is for use in vertebroplasty (e.g. osteoporotic vertebral fracture repair). The filler comprises (i) about 5 wt % polylysine; (ii) about 5 wt % gentamicin; (iii) about 25 wt % of a 1:1 molar ratio of (a) MCPM and (b) tristrontium phosphate and/or tricalcium phosphate; (iv) about 45 wt % radiopaque glass powder; and (v) about 20 wt % glass fibres. This formulation provides lower modulus, in addition to the other benefits described herein.

In some embodiments, the fluid formulation is for use as cement for hip and knee implant fixation, e.g. after infection. The filler comprises (i) about 5 wt % polylysine; (ii) about 10 wt % gentamicin; (iii) about 25 wt % of a 1:1 molar ratio of (a) MCPM and (b) tristrontium phosphate and/or tricalcium phosphate; (iv) about 40 wt % radiopaque glass powder; and (v) about 20 wt % glass fibres.

The fluid phase in the above embodiments comprises at least one compound capable of polymerisation and/or cross-linking, as described herein. Preferably, the fluid phase comprises (i) about 20 to about 74 wt % UDMA; (ii) about 75 to about 25 wt % PPGDMA, or about 25 wt % TEDGMA; (iii) 0.5 to about 2 wt % BP; (iv) about 0.5 wt % to about 2 wt % NTGGMA; and (v) about 100 to about 1000 ppm polymerisation inhibitor, e.g. MEHQ.

The combination of fluid phase and filler provides a number of advantages over the prior art. For example, PPGDMA high molecular weight reduces heat generation/monomer toxicity. PPGDMA with a strontium or calcium reactive component, glass fibres and polylysine enhances flexibility/toughness to prevent stress shielding. NTGGMA enhances polymerisation and strength. There is greater adhesion to both implants and surrounding bone by NTGGMA with PLS and strontium or calcium reactive component. In addition, high radiopacity due to higher glass content with UDMA instead of BISGMA enables visualisation with X-rays.

Polylysine Modified Brushite Bone Cements

An alternative to polymeric adhesives and fillers is the use of calcium phosphate cements (CPCs). These are generally considered to be more biocompatible than the polymers and are widely used e.g. in craniofacial surgery and dental applications [4,5]. For example, cements that form of hydroxyapatite (HA, $Ca_{10}(PO_4)_6(OH_2)$— the primary mineral component of bone, enamel and dentine) have been developed. One example involves reaction between tetracalcium phosphate and anhydrous dicalcium phosphate

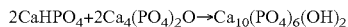
$$2CaHPO_4 + 2Ca_4(PO_4)_2O \rightarrow Ca_{10}(PO_4)_6(OH)_2$$

Upon mixing these phosphates with water, hydroxyapatite can slowly form. As the product crystallizes, it takes on a putty-like consistency and can be implanted or injected and contoured to a defect. The cement then completes the process and hardens, typically within ten to fifteen minutes, securing its position within the defect.

Faster setting aqueous calcium phosphate cements have also been developed using mixtures of high solubility monocalcium phosphate monohydrate (MCPM) and lower solubility tricalcium phosphate (β-TCP). These two phosphates combine rapidly when mixed with water to form lower density dicalcium phosphate dihydrate (DCPD, also known as brushite) according to the expression [6,7].

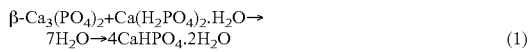
$$\beta\text{-}Ca_3(PO_4)_2 + Ca(H_2PO_4)_2 \cdot H_2O + 7H_2O \rightarrow 4CaHPO_4 \cdot 2H_2O \quad (1)$$

In these fast-setting cements the MCPM particles dissolve in water, then re-precipitate, solidifying the cement and forming brushite (DCPD) or monetite (dicalcium phosphate anhydrous (DCPA)) crystallites. In the body these may be slowly transformed to hydroxyapatite required for remineralisation of bone, and may further enhance stability. This may provide the material with a mechanism to repair damage caused by strain or water sorption.

Calcium phosphate bone cements (CPCs) (e.g. Norian, Bone Source) have also been used for vertebroplasty, screw augmentation and bone filling. These cements generally form either hydroxyapatite or brushite. Their major material advantage is chemical similarity with the inorganic component of tooth and bone and the ability to degrade to enable complete natural repair. Major concerns, however, can include difficulty in control of setting, dispersion in blood due to hydrophilicity or lack of cohesion, very low (particularly flexural) strength, high modulus, poor bone bonding and rapid drug release. There have been many attempts to overcome these problems by polymer or glass fibre addition but with only limited success.

Reactive calcium phosphate composites produced with brushite cement particles and methacrylate cross-linkable/polymerisable compounds are a newer class of experimental materials for tooth or bone repair. Calcium phosphates have been added to many experimental composites but most studies have focused upon the addition of only one type at a time that is relatively insoluble in water (e.g. amorphous calcium phosphate or hydroxyapatite or tricalcium phosphate or brushite).

A further aspect of the invention provides a fluid formulation for use in a process as described herein for production of a brushite bone cement. The fluid formulation comprises a fluid phase and a filler, wherein the fluid phase comprises about 20 wt % and the filler comprises about 80 wt %.

In this aspect, the filler comprises (i) between about 5 and 10 wt % active agent, e.g. chlorhexidine or gentamicin; and (ii) between about 90 and 95 wt % reactive component, e.g. a 1:1 molar ratio of (a) MCPM and (b) tristrontium phosphate and/or tricalcium phosphate; and the fluid phase comprises (iii) about 30 to about 50 wt % aqueous cationic polymer, e.g. aqueous polylysine, (iv) between about 0 and 20 wt % aqueous polyacrylic acid (PAA), and (v) between about 0 and 800 mM aqueous citric acid.

The fluid formulation and cements produced therefrom provide a number of advantages over the prior art, as described herein. For example, the cements provide an increased rate of active agent delivery than a polymer composite. The concentration of polylysine and polyacrylic acid (PAA) enable control over the drug delivery rate. The interactions between PAA/polylysine and the reactive component provide increased strength, reduced modulus, improved active agent release control, and enhanced bonding to surrounding tissue.

In some embodiments, the fluid formulation is for an antibacterial bone filler after tooth removal (e.g. jaw augmentation). The filler comprises (i) about 5 wt % chlorhexidine; and (ii) about 95 wt % of a 1:1 molar ratio of (a) MCPM and (b) tristrontium phosphate and/or tricalcium phosphate; and the fluid phase comprises (iii) about 30 wt % aqueous polylysine, (iv) about 20 wt % aqueous PAA, and (v) between about 0 and 400 mM aqueous citric acid.

In some embodiments, the fluid formulation is for an antibacterial bone filler after periodontal infection, or for cement around infected tooth implant (e.g. perioimplantitis treatment). The filler comprises (i) about 10 wt % chlorhexidine; and (ii) about 90 wt % of a 1:1 molar ratio of (a) MCPM and (b) tristrontium phosphate and/or tricalcium phosphate; and the fluid phase comprises (iii) about 30 wt % aqueous polylysine, (iv) about 20 wt % aqueous PAA, and (v) between about 0 and 400 mM aqueous citric acid.

In some embodiments, the fluid formulation is for an antibacterial coating for a titanium dental implant (e.g. tooth replacement). The coating comprises (i) about 10 wt % chlorhexidine or tetracycline; and (ii) about 90 wt % of a 1:1 molar ratio of (a) MCPM and (b) tristrontium phosphate and/or tricalcium phosphate; and the fluid phase comprises (iii) about 30 wt % aqueous polylysine, (iv) between 0 and 20 wt % aqueous PAA, and (v) between 0 and 400 mM aqueous citric acid.

In some embodiments, the fluid formulation is for a bone filler, e.g. after tumour removal. The filler comprises (i) about 5 wt % gentamicin; and (ii) about 95 wt % of a 1:1 molar ratio of (a) MCPM and (b) tristrontium phosphate; and the fluid phase comprises (iii) about 50 wt % aqueous polylysine; and (iv) between about 0 and 400 mM aqueous citric acid. Strontium with polylysine will enhance antibacterial properties and bone repair In some embodiments, the fluid formulation is for a bone filler e.g. for prophylactic osteoporotic fracture prevention. The filler comprises (i) about 5 wt % gentamicin; and (ii) about 95 wt % of a 1:1 molar ratio of (a) MCPM and (b) tristrontium phosphate and/or tricalcium phosphate; and the fluid phase comprises (iii) about 50 wt % aqueous polylysine; and (iv) between about 0 and 400 mM aqueous citric acid.

In some embodiments, the fluid formulation is for osteomyelitis treatment. The filler comprises (i) about 10 wt % gentamicin; and (ii) about 90 wt % of a 1:1 molar ratio of (a) MCPM and (b) tristrontium phosphate and/or tricalcium phosphate; and the fluid phase comprises (iii) about 50 wt % aqueous polylysine; and (iv) between about 0 and 400 mM aqueous citric acid.

In some embodiments, the fluid formulation is for an antibacterial coating or cement for a titanium bone implant (e.g. surface active and antibacterial titanium screws or pins and bone augmentation). The coating or cement comprises (i) about 10 wt % gentamicin or tetracycline; and (ii) about 90 wt % of a 1:1 molar ratio of (a) MCPM and (b) tristrontium phosphate and/or tricalcium phosphate; and the fluid phase comprises (iii) about 30 wt % aqueous polylysine, (iv) between 0 and 20 wt % aqueous PAA, and (v) between about 0 and 400 mM aqueous citric acid.

A further aspect of the invention provides a fluid formulation for use in sustained release of DNA. The fluid formulation comprises a fluid phase and a filler, wherein the fluid phase comprises between about 10 and 30 wt % and the filler comprises about 70 and 90 wt %. Preferably, the fluid phase comprises about 20 wt % and the filler comprises about 80 wt %.

In this aspect, the filler comprises between about 90 and 100 wt % reactive component, preferably 100 wt % reactive component e.g. a 1:1 molar ratio of (a) MCPM and (b) tristrontium phosphate and/or tricalcium phosphate; and the fluid phase comprises about 30 to about 70 wt % aqueous cationic polymer, e.g. aqueous polylysine, and between about 0.001 to about 10 wt % DNA. Preferably, the filler comprises about 100 wt % reactive component, and the fluid phase comprises about 50 wt % polylysine and between about 0.001 and 10 wt % DNA. Sustained release of DNA with polylysine will enable increased and prolonged non-viral gene transfection.

Degradable Composites

A further aspect of the invention provides a fluid formulation for use in a process as described herein for production of a degradable composite. The fluid formulation comprises a fluid phase and a filler, wherein the fluid phase comprises about 25 wt % and the filler comprises about 75 wt %.

In this aspect, the filler comprises (i) about 1 to about 20 wt % cationic polymer, e.g. polylysine; (ii) about 5 to about 20 wt % active agent, e.g. chlorhexidine or antibiotic agent; and (iii) about 50 to about 90 wt % reactive component, e.g. a 1:1 molar ratio of (a) MCPM and (b) tristrontium phosphate and/or tricalcium phosphate.

The fluid phase in this aspect comprises at least one compound capable of polymerisation and/or cross-linking to form a degradable material, as described herein. Preferably, the fluid phase comprises (i) about 50 to about 99 wt % PPGnLAmDMA; (ii) about 1 wt % CQ and/or about 0.25 to about 2 wt % BP; (iii) about 0.25 wt % to about 2 wt % DMPT or NTGGMA; and (iv) about 100 to about 1000 ppm polymerisation inhibitor, e.g. MEHQ.

Preferably, n is between about 5 and 40, and m is between about 2 and 10. In some embodiments, n is 7, 17 or 34 and m is 2, 4 or 8.

The fluid formulation and degradable composite material produced therefrom provides a number of advantages over the prior art, as described herein. For example, enhanced water sorption may increase the rate of degradation. In addition, enhanced water sorption compensates shrinkage during setting, and polymerisation enhancement by the cationic polymer, e.g. polylysine, may reduce set material toxicity. The enhanced water sorption promotes reactive filler reaction, which is required if the PPGnLAmDMA monomer is hydrophobic, i.e. when "n" and "m" are small. Adhesion to both implants and surrounding bone may be increased. The degradable composite material further provides very high flexibility and/or toughness to prevent stress shielding.

In some embodiments, the fluid formulation is for a flexible cement around an infected tooth implant (e.g. peri-oimplantitis), or for an antibacterial flexible membrane or cement for a periodontal pocket. The filler comprises (i) about 20 wt % polylysine; (ii) about 20 wt % chlorhexidine and/or antibiotic agent; and (iii) about 60 wt % reactive component, e.g. a 1:1 molar ratio of (a) MCPM and (b) tristrontium phosphate and/or tricalcium phosphate.

In some embodiments, the fluid formulation is for a bone glue. The filler comprises (i) about 4 wt % polylysine; (ii) about 6 wt % chlorhexidine and/or antibiotic agent; and (iii) about 90 wt % reactive component, e.g. a 1:1 molar ratio of (a) MCPM and (b) tristrontium phosphate and/or tricalcium phosphate.

Compomers

Compomers contain components of composites and acid group containing monomers but no water. In principle, the acid groups could provide adhesion but in practice compomers like composites, require additional adhesives for dentine bonding. Compomers additionally contain basic fluoride containing glass particles. The surfaces of these particles may react with acid groups when the material absorbs water to provide fluoride release. The level of water sorption and therefore the extent of this reaction and fluoride release, however, can be severely restricted by the hydrophobicity of the surrounding polymer matrix.

A further aspect of the invention provides a fluid formulation for use in a process as described herein for production of a compomer. The fluid formulation comprises a fluid phase and a filler, wherein the fluid phase comprises about 10-30, preferably 20 wt % and the filler comprises about 70-90, preferably 80 wt %.

In this aspect, the filler comprises (i) about 0.2 to about 12.5 wt %, preferably about 5 wt % cationic polymer, e.g. polylysine; (ii) about 0 to about 12.5 wt % active agent, e.g. chlorhexidine or antibiotic agent; and (iii) about 5 to about 20 wt %, preferably 10 wt % basic reactive glass, and (iv) between about 70 and 90 wt %, preferably about 80 wt % radiopaque glass.

In some embodiments, the filler comprises about 5 wt % polylysine, about 5 wt % chlorhexidine, about 10 wt % basic reactive glass and about 80 wt % radiopaque glass.

Compomers are hybrids of dental composites and GICs. Therefore the fluid phase comprises at least two compounds capable of polymerisation and/or cross-linking, as described herein. Preferably, one of the at least two compounds is a polyacid as described herein, and the second is a methacrylate as described herein. In some embodiments, the fluid phase comprises UDMA:TEGDMA:acidic monomer in a 3:1:0.5 by wt ratio, and preferably 1% CQ and NTGGMA.

Basic reactive dental glasses typically contain 20-30% $Al_2O_3$, 20-30% $SiO_2$, 10-20% fluoride, and 10-30% calcium strontium and zinc oxides. In formulations such as compomers and RMGICs, basic reactive glass is preferentially coated with silane.

Glass Ionomer Cements (GICs)

Other types of dental repair materials include glass ionomer cements (GICs), e.g. Fuji IX. GICs consist of an aqueous polyacid solution that reacts with basic aluminosilicate fillers. The polyacids ensure GICs can bond directly to untreated dentine, but preconditioning with a diluted polyacid solution improves bond strength. GIC early bond strength is lower than with composites, and the failure in larger multisurface tooth restorations is common due to poor GIC flexural strength. In simple one surface cavity restorations, however, the GIC bond may be clinically more durable.

A further aspect of the invention provides a fluid formulation for use in a process as described herein for production of a glass ionomer cement. The fluid formulation comprises a fluid phase and a filler, wherein the fluid phase comprises about 15-35, preferably about 25 wt % and the filler comprises about 65-85, preferably about 75 wt %.

In this aspect, the filler comprises (i) about 0.2 to about 12.5 wt %, preferably about 5 wt % cationic polymer, e.g. polylysine; (ii) about 0 to about 12.5 wt % active agent, e.g. chlorhexidine or antibiotic agent; and (iii) about 80 to about 95 wt %, preferably 90 wt % basic reactive glass.

In some embodiments, the filler comprises about 5 wt % polylysine, about 5 wt % chlorhexidine, and about 90 wt % basic reactive glass.

The fluid phase comprises water and a polyacid, e.g. a polyalkenoic acid, preferably PAA, at a weight ratio of between about 0.5:1 and 1:0.5, preferably about 1:1 by weight. Preferably, the polyacid is 2000 g/mol PAA and the water:PAA ratio is 1:1.

In embodiments wherein the material is a GIC, the cationic polymer, e.g. polylysine, may be comprised in the fluid phase, e.g. as an aqueous cationic polymer as described herein. In such embodiments, the total wt % of the cationic in the fluid formulation or material will be the same as embodiments in which the cationic polymer is in the filler.

Resin Modified GICs (RMGICs)

Hybrid restoration materials (e.g. Fuji II LC) have also been produced to overcome limitations of GICs and composites. The resin modified glass ionomer cements (RMGICs) for example, consist of GIC components (including water) and usually hydrophilic polymerisable compounds such as HEMA. The polymerisable compound additions can double the GIC flexural strength, but this is still generally significantly below that of composites.

A further aspect of the invention provides a fluid formulation for use in a process as described herein for production of a resin modified glass ionomer cement. The fluid formulation comprises a fluid phase and a filler, wherein the fluid phase comprises about 15-35, preferably about 25 wt % and the filler comprises about 65-85, preferably about 75 wt %.

In this aspect, the filler comprises (i) about 0.2 to about 12.5 wt %, preferably about 5 wt % cationic polymer, e.g. polylysine; (ii) about 0 to about 12.5 wt % active agent, e.g. chlorhexidine or antibiotic agent; and (iii) about 80 to about 95 wt %, preferably 90 wt % basic reactive glass.

In some embodiments, the filler comprises about 5 wt % polylysine, about 5 wt % chlorhexidine, and about 90 wt % basic reactive glass.

The fluid phase comprises water, a polyacid, e.g. a polyalkenoic acid, preferably PAA, and a methacrylate, preferably HEMA, at e.g. a 1:1:2 weight ratio. Preferably, the fluid phase comprises HEMA:water:PAA at a 2:1:1 weight ratio. Preferably, the fluid phase further comprises 1% CQ and NTGGMA.

In embodiments wherein the material is a RMGIC, the cationic polymer, e.g. polylysine, may be comprised in the fluid phase, e.g. as an aqueous cationic polymer as described herein. In such embodiments, the total wt % of the cationic in the fluid formulation or material will be the same as embodiments in which the cationic polymer is in the filler.

Dental Adhesives and Coatings

A further aspect of the invention provides a fluid formulation for use in a process as described herein for production of a dental adhesive or coating. The fluid formulation comprises a fluid phase and a filler, wherein the fluid phase comprises about 85-95, preferably about 92 wt % and the filler comprises about 5-15, preferably about 8 wt %.

In this aspect, the filler comprises (i) about 0 to about 60 wt %, 40-60, or preferably about 50 wt % cationic polymer, e.g. polylysine; and (ii) about 0 to about 60, 40-60 wt % or preferably about 50 wt % active agent, e.g. chlorhexidine or antibiotic agent.

In some embodiments, the filler comprises about 50 wt % polylysine and about 50 wt % chlorhexidine.

Preferably, the fluid phase comprises HEMA, UDMA, TEGDMA and 4META at a weight ratio of about 3:2:1:0.5. Preferably, the fluid phase further comprises 1% CQ and NTGGMA.

Uses

In one aspect, the invention provides a method of tooth or bone repair, which method comprises performing a process for production of a material of the invention, wherein:
(i) a fluid formulation of the invention is introduced into the site of tooth or bone damage; and
(ii) polymerising and/or cross-linking of the compound capable of polymerisation and/or cross-linking is performed by curing said formulation to form a material which is adhered to the damaged tooth or bone.

A further aspect of the invention provides a method of fixation of a dental or surgical implant into a cavity or location, which method comprises performing a process for production of a material of the invention, wherein:
(i) the fluid formulation is introduced into the cavity or location;
(ii) polymerising and/or cross-linking said compound is performed by curing said formulation to form a material which is adhered to said dental or surgical implant In some embodiments of the above methods, the cationic polymer may
(i) promote water sorption of the material; and/or
(ii) promote formation of a layer on the material comprising the cationic polymer;
(iii) promote formation of a bone or dentine-like layer on the material, and re-adsorbs on this layer; and/or
(iv) enhance conversion of the polymerising and/or cross-linking compound to a polymer matrix.

In preferred embodiments, the material comprises an active agent as described herein, and the cationic polymer promotes release of the active agent.

One aspect of the invention provides the fluid formulations or materials of the invention for use in therapy. In some embodiments, the therapy comprises the treatment of dental caries, the treatment of bone damage or the treatment of osteoporosis and the like.

A further aspect of the invention relates to a cationic polymer, e.g. polylysine, for use in fluid formulation to achieve the advantageous properties described herein.

The invention provides a cationic polymer, e.g. polylysine for use in a material or fluid formulation for the production of a composite or cement for tooth or bone repair. Preferably, the material or fluid formulation are as described herein.

In some embodiments, the cationic polymer, e.g. polylysine, is released from the material after setting, and readsorbs onto the surface of the material.

In some embodiments, the cationic polymer, e.g. polylysine, enhances production of self-repairing surface layers that are antibacterial and remineralising.

In some embodiments, the cationic polymer, e.g. polylysine, enhances production of surface hydroxyapatite layers on the material after setting.

In some embodiments, the cationic polymer, e.g. polylysine, enhances water sorption of the material.

One aspect of the invention provides a cationic polymer, e.g. polylysine, for use in decreasing the modulus of a material used for tooth or bone repair. Preferably, the material are as described herein, or produced from a fluid formulation of the invention as described herein A further aspect provides a cationic polymer, e.g. polylysine, for use in a composite, cement or fluid formulation for treating osteoporosis. Preferably, the composite, cement or fluid formulation are of the invention as described herein.

A further aspect provides a cationic polymer, e.g. polylysine for use in a composite, cement or fluid formulation for treating dental caries. Preferably, the composite, cement or fluid formulation are of the invention as described herein A further aspect provides a cationic polymer, e.g. polylysine, for use in promoting release of an active agent from a composite, cement or fluid formulation for the production of a material for tooth or bone repair. Preferably, the active agent is as described herein. Most preferably the active agent is chlorhexidine. Preferably, the material or fluid formulation are of the invention as described herein.

A further aspect provides a cationic polymer, e.g. polylysine for use as a polymerization activator of polymerisable methacrylates. Preferably, the polymerisable methacrylate is as described herein.

A further aspect provides polylysine for use in reducing or reversing the shrinkage of a fluid formulation of the invention during polymerisation/cross-linking of the fluid formulation or compound capable of polymerisation and/or cross-linking.

Further aspects of the invention relate to a method of treating tooth or bone defects using the formulations, materials and methods described herein.

A further aspect provides the use of a fluid formulation or material as described herein in the manufacture of a medicament for the treatment of tooth or bone defects.

Kits

A further aspect of the present invention provides a kit for producing a fluid formulation and/or a material according to the invention, e.g. for tooth or bone repair, comprising:
(a) at least one compound capable of polymerising and/or cross-linking to form a solid polymer matrix;
(b) optionally a filler optionally comprising a reactive component capable of reaction with water absorbed into the polymer matrix to produce a solid material;
(c) a cationic polymer, optionally forming part of the filler; and
(d) optionally written instructions for combining the compound capable of polymerising and/or cross-linking, cationic polymer and optional filler and curing them.

Preferably the material, polymerisable/cross-linkable compound, filler and cationic polymer are as described herein.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

BRIEF DESCRIPTION OF THE FIGURES

FIG. 23: Solubility of dental composites of Example 13

EXAMPLES

Methods

The formulations described herein mostly had a fluid phase comprising largely of the base monomer UDMA (a compound capable of polymerisation and/or cross-linking), unless otherwise stated. The diluent was either TEGDMA or PPGDMA. The ratio of base:diluent monomer was 3:1 unless otherwise stated HEMA was typically also added at 5 wt %.

The filler was primarily silane-treated glass, combined with varying levels of chlorhexidine (CHX), polylysine (PLS), glass fibres and reactive calcium phosphate (CaP). Unless otherwise stated the reactive calcium phosphate consists of equal mass of MCPM and TCP. Unless otherwise stated, the total powder to liquid ratio was fixed at 4:1 by weight, i.e. 80 wt % filler to 20 wt % fluid phase.

Light cure dental formulations contained CQ with DMPT at 1 wt % of the monomer. Monomer was mixed with powder by hand on a mixing pad. To set these materials they were exposed to a blue dental light for sufficient time (typically 60s) to ensure maximum monomer conversion.

Figure 1:
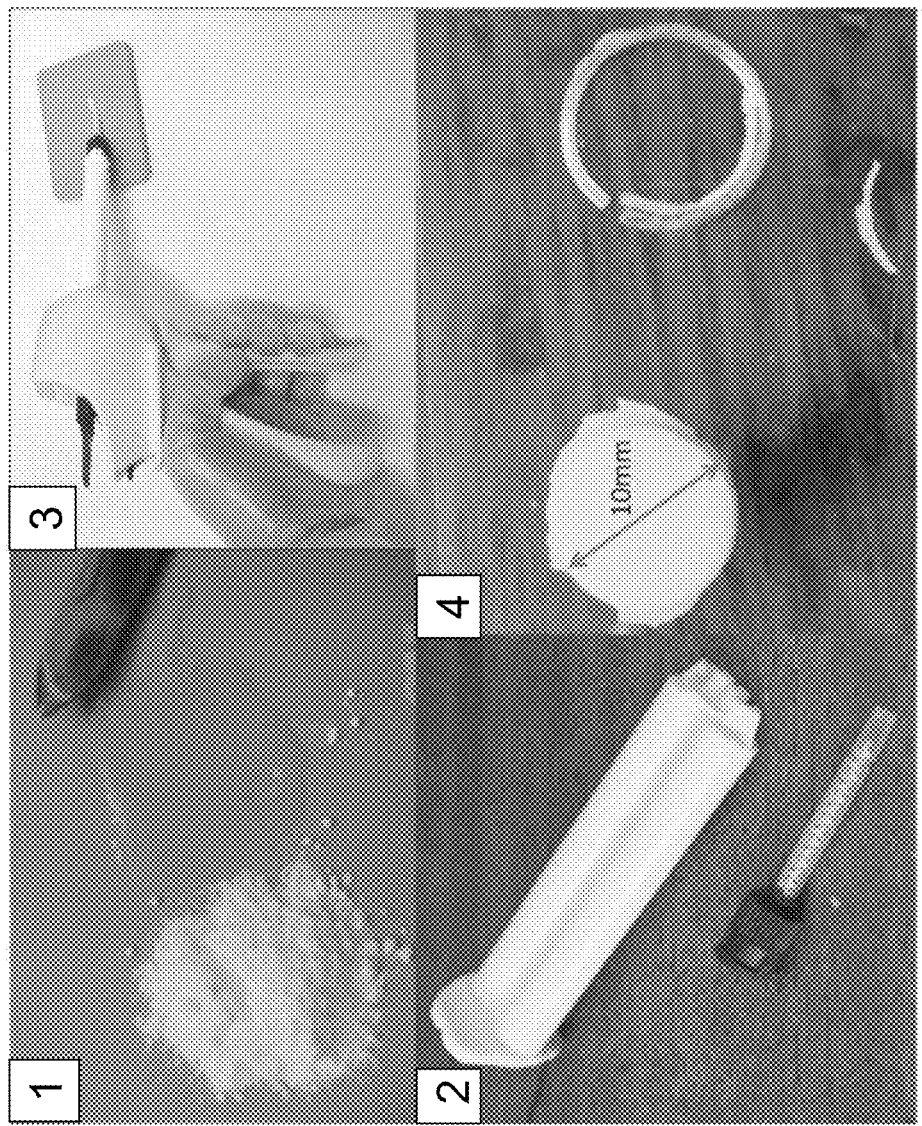
FIG. 1: Mixing of pastes and production of specimens for sample testing

Chemical cure bone composites contained BP and DMPT or NTGGMA. Levels in the monomer were varied to determine concentrations that provided sufficient mixing time before rapid polymerisation. Chemical cure formulations were prepared as initiator and activator pastes and mixed using double barrelled syringes with automatic mixing tips (FIG. 1).

Specimens of 10 mm diameter and 1 mm thick were prepared using split bass rings for all tests unless otherwise specified. After curing excess material from around the discs was removed prior to testing.

Samples were stored for 24 hours at 37° C. prior to testing or placement in 10 ml water or simulated body fluid (SBF). Samples were removed typically at 2, 4, 6, 24, 48 hours, 1,2,3,4 and 6 weeks to assess properties and/or storage solutions and returned to fresh solutions at these times. The composition of SBF conformed to ISO 23317. (Implants for surgery—In vitro evaluation for apatite-forming ability of implant materials (2007))

The time taken for the UDMA to polymerise (also known as the monomer conversion time) was determined using Fourier transform infrared spectroscopy (FTIR) with a golden gate diamond attenuated total reflectance (ATR) attachment (Specac) and Timebase software (Khan 2012, Zhao 2011).

Shrinkage and heat generation were calculated by assuming one mole of polymerising C=C bonds generates 57 kJ of heat and gives volumetric shrinkage of 23 cm³. The total heat generation and shrinkage due to the composite curing process can therefore be estimated using equations $$\text{vol }(\%) = 23N*100$$

$$\text{Heat}(kJ/cc) = 57N$$

N is the number of moles of reacted bonds per unit volume. This can be estimated using $$N = mC\rho_{comp} \sum_i \left(\frac{n_i x_i}{W_i}\right)$$

m is the total monomer mass fraction and C the final fractional monomer conversion calculated from FTIR. $n_i$, $W_i$ and $x_i$ are number of c=c bonds per molecule, molecular weight (g/mol) and mass fraction of monomer i respectively. Assuming the formulation density, $\rho_{comp}$ (g/cm³), behaves "ideally" it can be estimated using a simple rule of mixtures $$1/\rho_{comp} = m/\rho_{monomer} + (1-m)/\rho_{filler}$$

$\rho_{monomer}$ and $\rho_{filler}$ are the densities of the monomer mixture and filler.

Biaxial flexural strength (BFS) and modulus was determined using a 'Ball on Ring' method (Mehdawi 2009 and 2013, Zhao 2011).

Fatigue testing was undertaken for 1,000 cycles, at 1 Hz. A preload of 5N and a peak load of 80% of the estimated yield were used. The peak load was either lowered or raised by 5%, depending on whether the previous specimen studied failed or not.

Mass change was assessed via gravimetric analysis of specimens (Mehdawi 2009, Zhao 2011).

Water content and mass loss were assessed by vacuum drying specimens and determining any changes in mass.

CHX and PLS release into sample storage solutions were quantified using UV spectrometry (Mehdawi 2009, Zhao 2011) and HPLC respectively.

Calcium phosphate precipitation on material surfaces was assessed after storing samples in water and simulated body fluid (SBF, ISO 23177, 2007). Scanning electron microscopy (SEM) was used to assess layer homogeneity and Raman to confirm chemical composition. The difference in mass change in water versus simulated body fluid (SBF) was used to evaluate average layer mass/thickness.

Bonding to ivory dentine was determined by drilling and filling/restoring holes 3 mm diameter through 5 mm thick ivory slabs and assessing force required to push out the material cylinder. Prior to filing, the ivory cavity was treated with 37% phosphoric acid gel and rinsed with water.

Example 1

Light Cure Composites for Tooth Restoration

Fracture Behaviour

Figure 2:
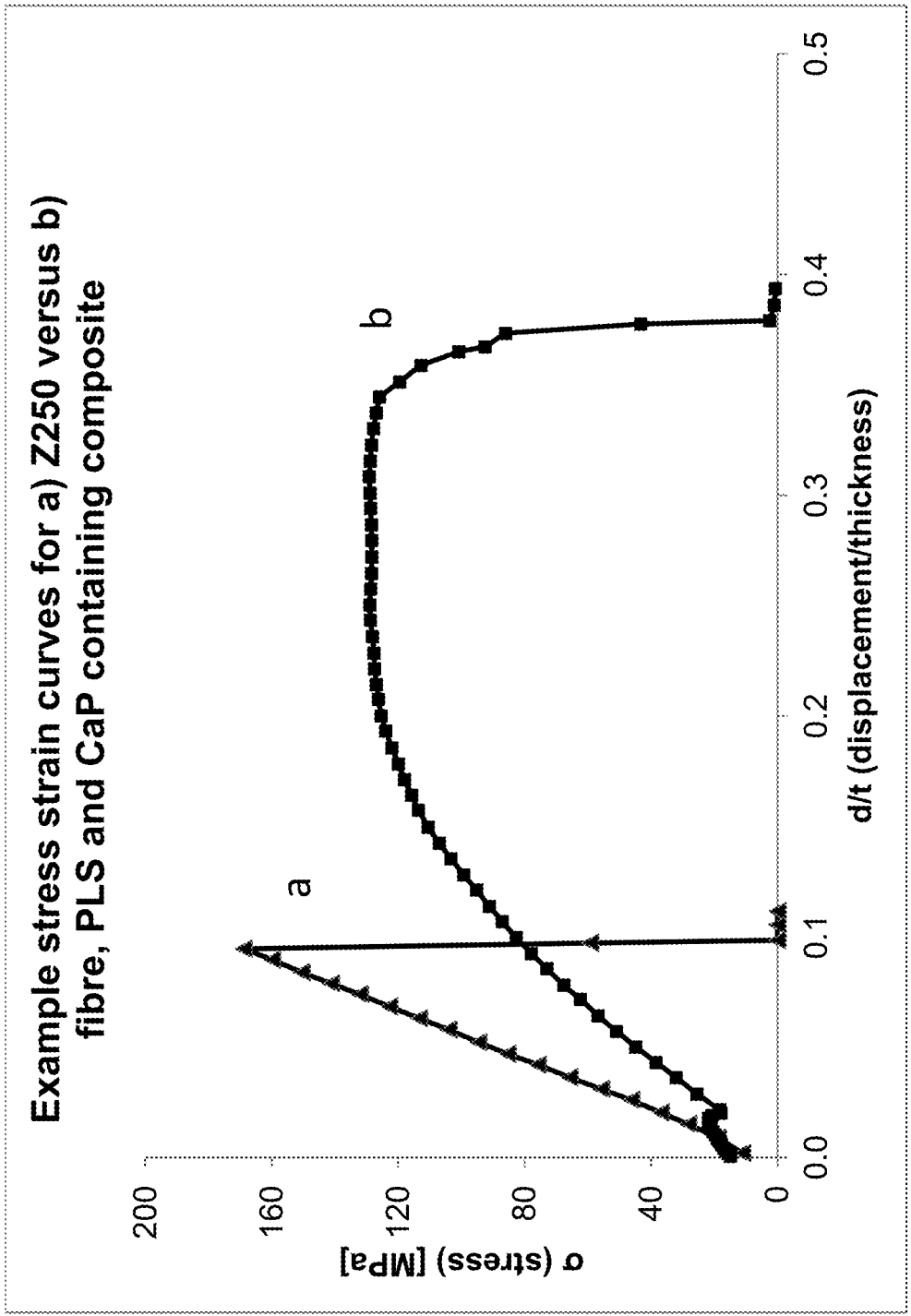
FIG. 2: Example stress strain curves for a) Z250 and b) fibre, PLS and CaP containing composites of the invention.

All commercial materials tested exhibited brittle fracture (see for example Z250 in FIG. 2a). The only exception was a fibre reinforced composite (FRC) which could maintain some load after a yield point. Conversely, the experimental composites with reactive CaP fillers, fibres and PLS could all maintain load at high levels of central displacement (FIG. 2b).

Strength, Modulus and Toughness

Figure 3:
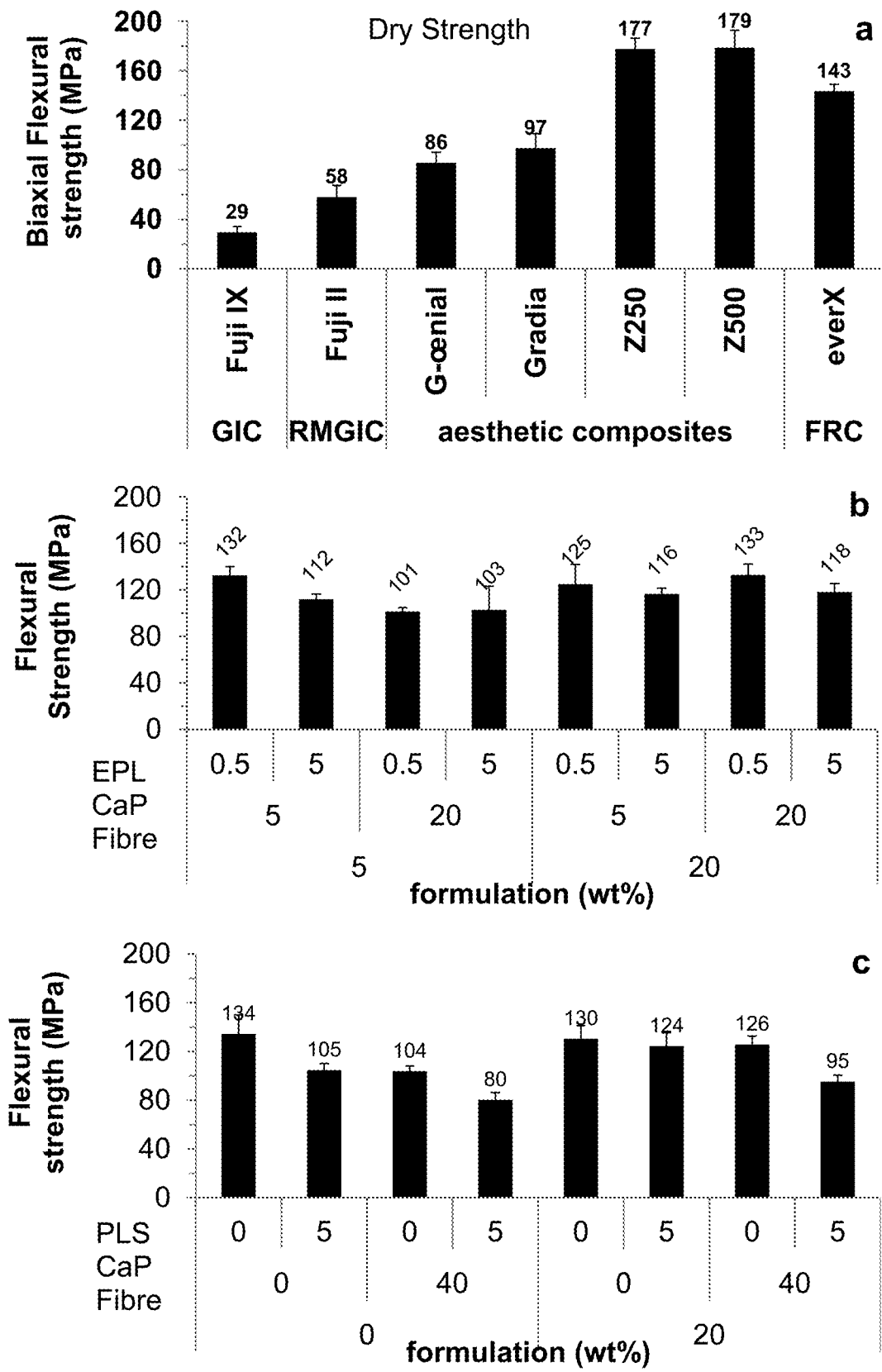
FIG. 3: Dry strength, modulus and toughness of (a) commercial, and PLS, CaP and fibre containing experimental composites prepared using (b) TEGDMA or (c) PPGDMA diluent
Figure 3:
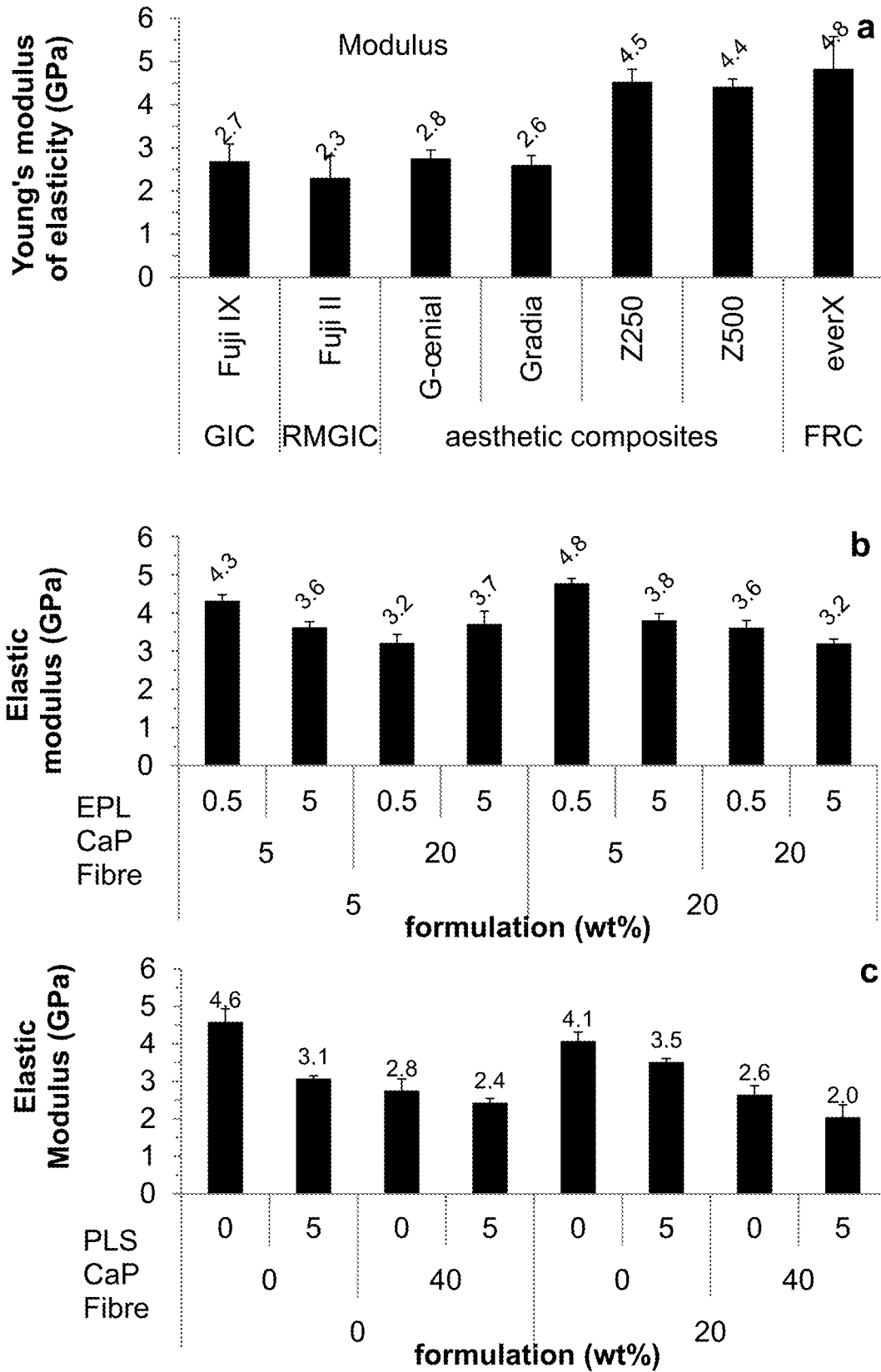
Figure 3:
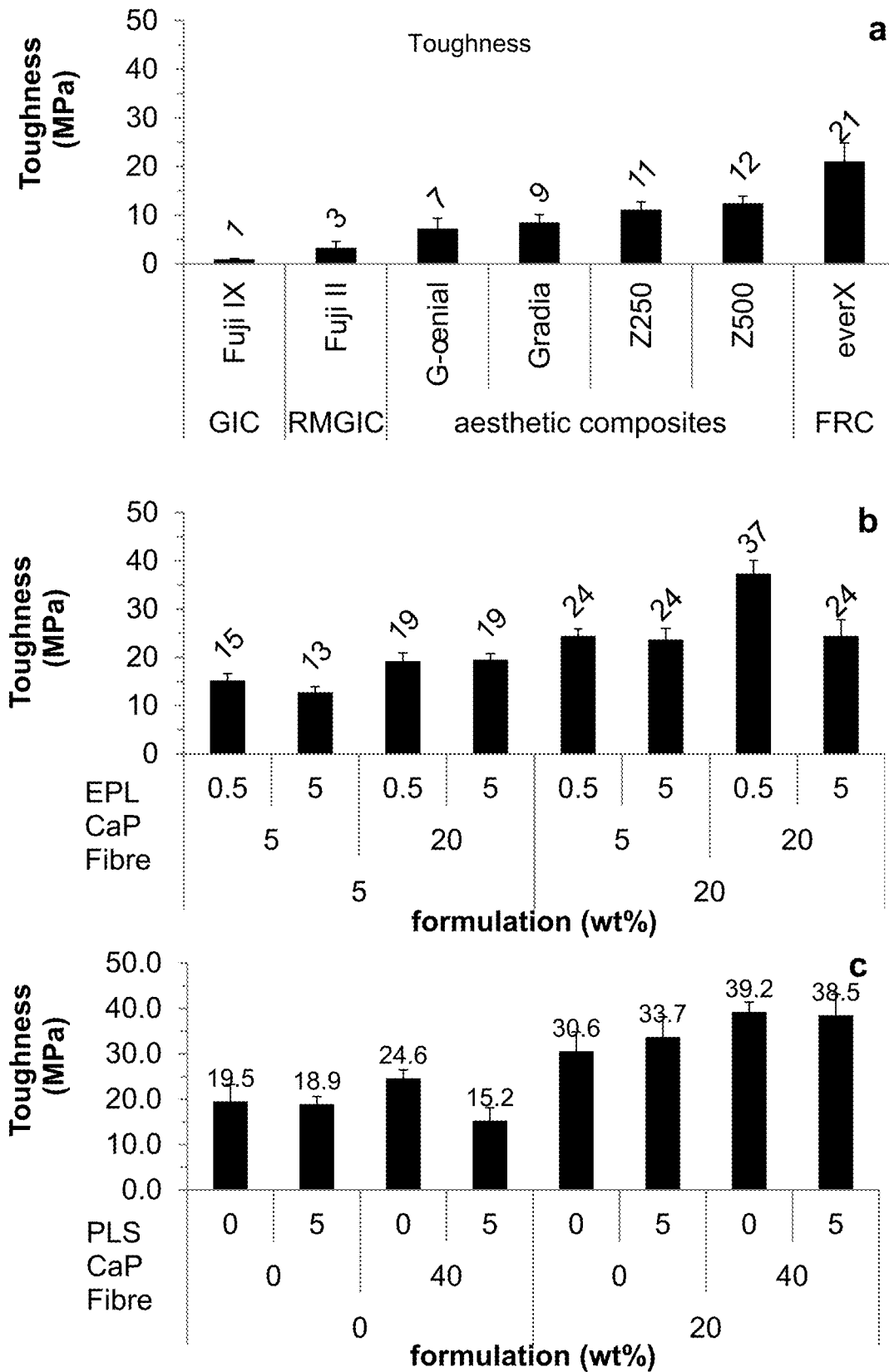

As shown in FIG. 3a, the biaxial flexural strengths of commercial composites ranged between 86 and 180 MPa, and the modulus between 2.6 and 4.8 MPa. Strength was 3-4% of modulus. Area under curves was 12 MPa or less, except for the FRC with an area of 21 MPa. Experimental formulations containing TEGDMA diluent (FIG. 3b) or PPGDMA diluent (FIG. 3c) had similar strengths and moduli but with the addition of fibres CaP and PLS (EPL=ε-polylysine) could be much tougher even than the commercial FRC (see FIGS. 2b, 3b and 3c). In FIG. 3 PLS is at 0, 0.5 or 5 wt %, CaP at 0, 50, 20 or 40 wt % and Fibre at 0, 5 or 20 wt % of the powder.

Fatigue Testing

Tough formulations are expected to resist cyclic loading. A PPGDMA composite containing glass particles only in the powder phase had a yield stress of 164±16 MPa and toughness of 17±5 MPa. Under fatigue testing, 60% of specimens failed at 70 to 80% of the failure load. Conversely reactive filler composites containing 20 wt % fibres and 40 wt % CaP (in the powder phase) had a yield stress of 101±6 MPa and toughness of 39±3 MPa. One hundred percent of these survived loading at 75% of the estimated failure load. Some specimens survived 80 and 85% of the estimated failure load. We propose this resistance to cyclic loading could provide time for the material to self-repair through dynamic ionic bonds within the material and dissolution/reprecipitation of reactive calcium phosphates.

Bonding

Figure 4:
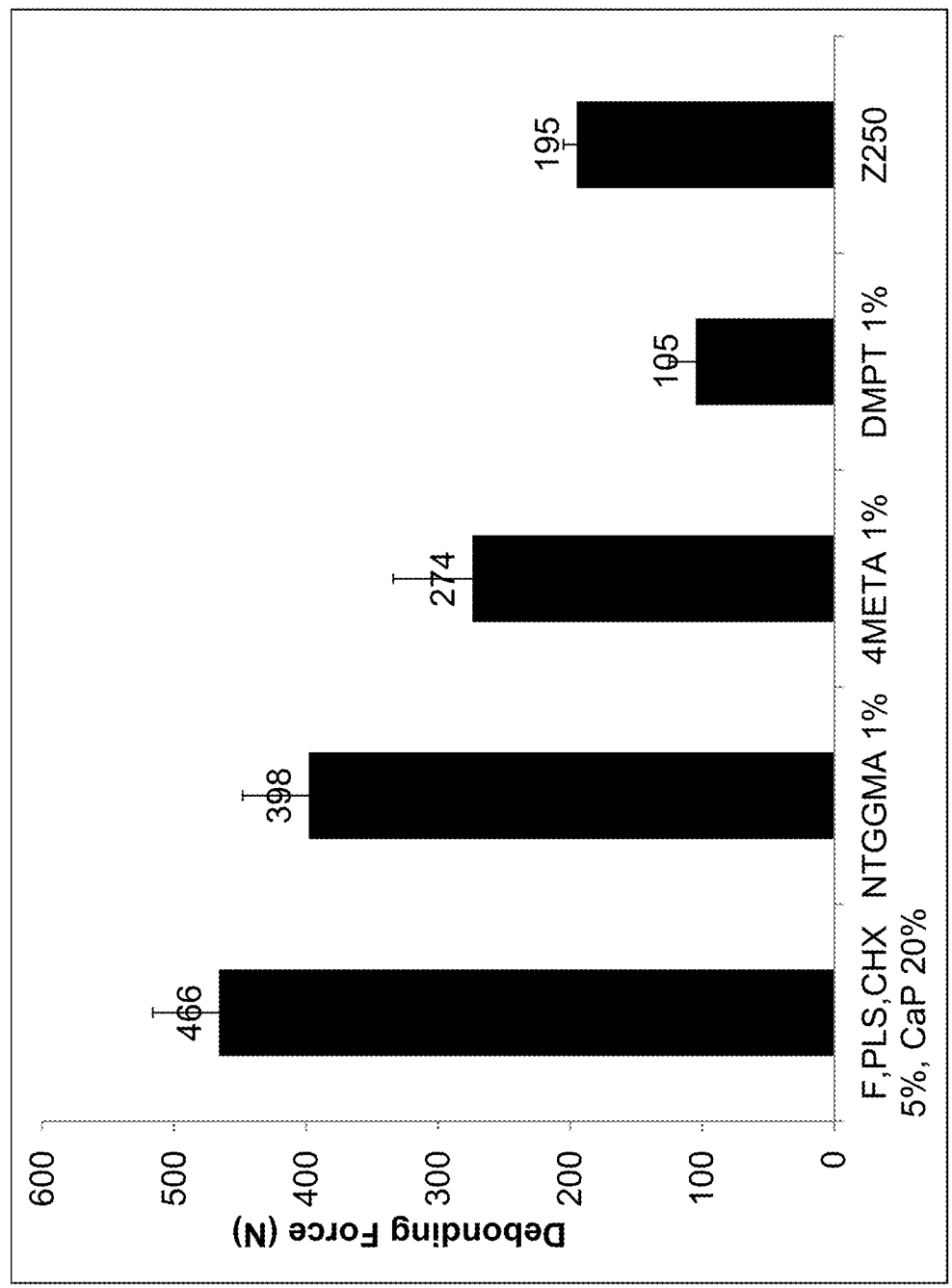
FIG. 4: Debonding force required to push out cylinders of composites from phosphoric acid treated ivory dentine

The bonding of light cure composites to dentine was assessed using elephant ivory. When the commercial composite Z250 was used to fill an ivory dentine cavity, less than 200N force was required to push the material cylinder out if no adhesive was used. Standard UDMA composites produced using DMPT and a filler of glass only (i.e. no reactive components) required even less push out force. Adding, 1% 4META or replacing the DMPT with NTGGMA increased this force to 274 and 398N respectively, as would be expected with the addition of dentine bonding carboxylic acid groups. By contrast, a reactive filler composite of the invention comprising a fluid phase comprising UDMA and DMPT, and a filler of 20 wt % reactive CaP, 5 wt % PLS, 5 wt % CHX, 5 wt % glass fibres, and 65 wt % barium aluminosilicate glass (DMG) glass powder, gave a push out force even higher at 466N. The composites of the invention therefore show good bonding with dentine without the need for a separate adhesive (see FIG. 4).

Example 2

Water Sorption and Calcium Phosphate Precipitation

Figure 5:
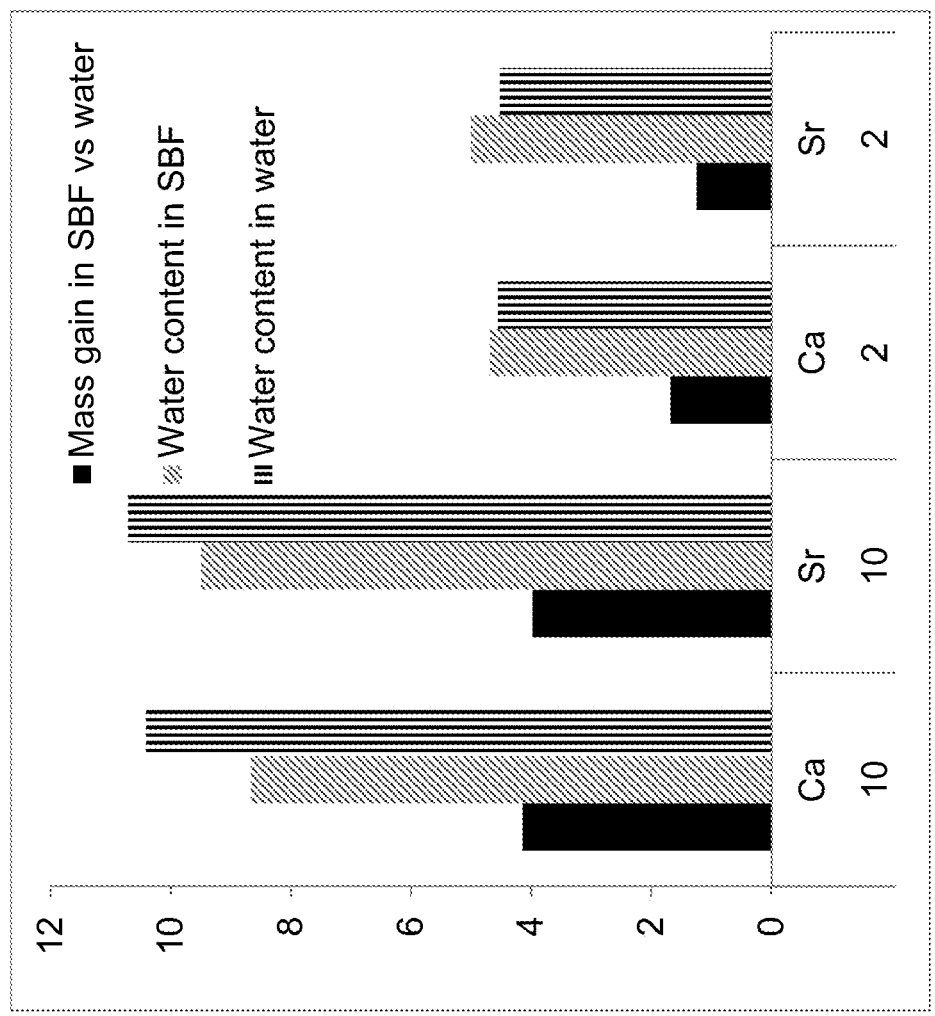
FIG. 5: Water content of UDMA/TEGDMA/CHX reactive filler composites (10 wt % TCP or tristrontium phosphate, 10 wt % MCPM and 2 or 10 wt % PLS in the silica based filler) after 2 weeks storage in water or SBF.

Composite discs were prepared using UDMA:TEGDMA diluent 3:1 mass ratio. This was combined with a barium aluminosilicate glass (DMG) mixed with polylysine (2 or 10 wt %), 10 wt % TCP or the strontium equivalent, 10 wt % MCPM and 10 wt % CHX. The filler comprised 80 wt % of the total formulation. All formulation combinations increased in mass in both water and simulated body fluid (SBF). Mass gain due to calcium phosphate precipitation was estimated from the percentage mass gain in SBF minus the percentage material loss in water. Most mass change was in the first 24 hours. Upon drying at 2 weeks the samples containing 2 wt % PLS in the filler were found to have absorbed 4-5% water (FIG. 5). From the chemical equation for brushite formation (1) given above, 1 g of MCPM requires 0.5 g of water for full reaction. 10 wt % MCPM in the filler (i.e. powder phase) is equivalent to 8% of the total composite. 4% water sorption is therefore sufficient to enable all the MCPM to react and form brushite in the composite. By contrast, in similar composites with no PLS, water sorption was too low (0.8%) for all the reactive filler to form brushite (Mehdawi 2013). Therefore PLS promotes water sorption and the conversion of reactive filler to brushite, which enhances biocompatibility and provides control over calcium phosphate release levels.

SEM images of "fracture surfaces" were consistent with this brushite-forming reaction occurring in the bulk of the material (FIG. 6a). Expansion associated with this water sorption can help combat polymerization shrinkage. Preferably, the expansion is less than about 4%, otherwise the tooth may be cracked.

Composite materials with 10 wt % PLS had absorbed 8-11% water in 2 weeks. SEM showed surfaces of these samples could be pitted (FIG. 6c), but were less so with 2 wt % PLS (FIGS. 6b and d). Furthermore, there was ~3% material loss from 10 wt % PLS containing samples in water but none from those with 2 wt % PLS. Excess water sorption and material loss would explain the reduction in composite strength observed upon placement in water if the PLS level is too high in comparison with reactive filler.

Figure 6:
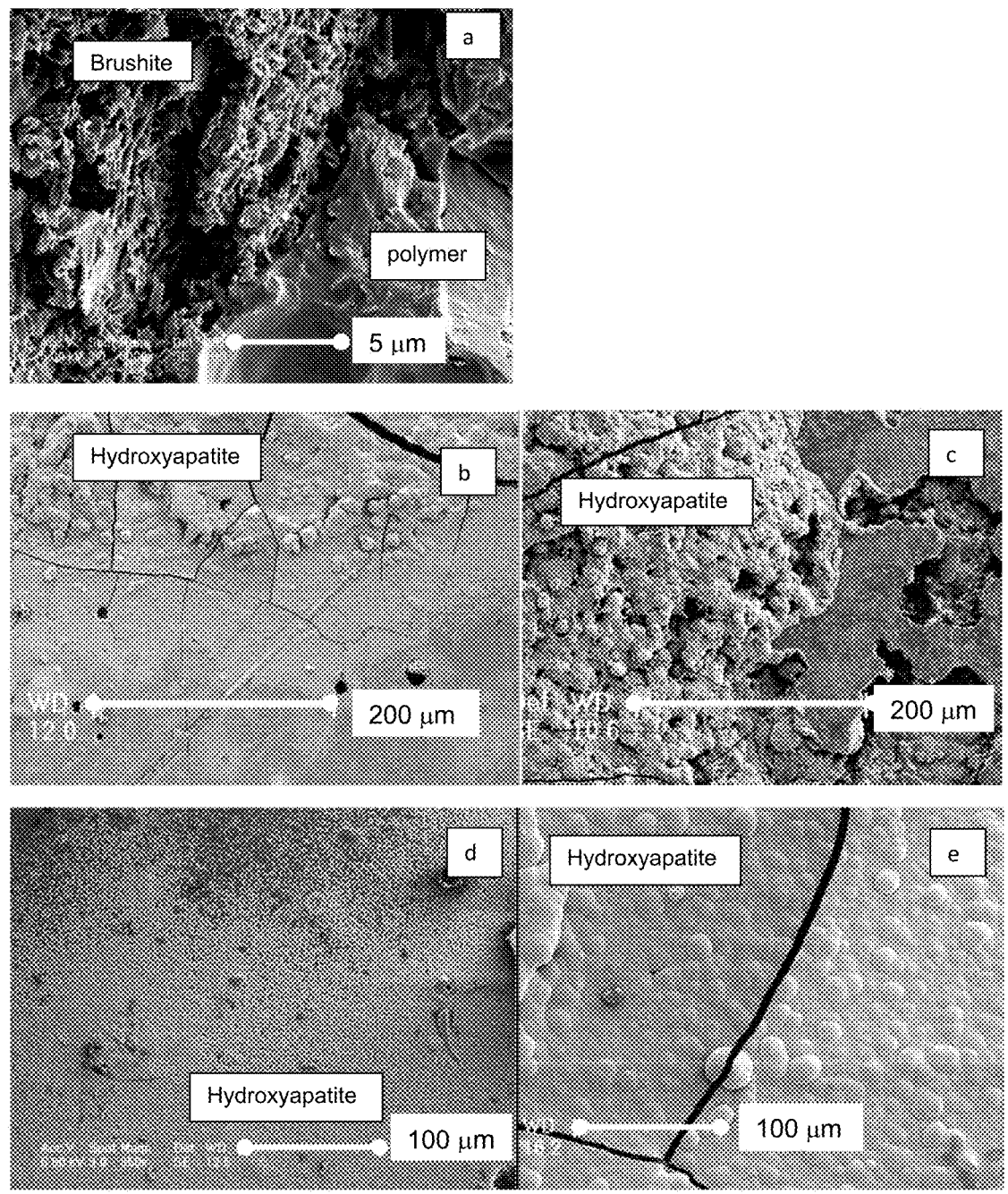
FIG. 6: SEM images showing a fracture surface demonstrating brushite formation within holes in the polymer composite (a) and calcium phosphate layers on surfaces of samples described in FIG. 5 after 2 weeks in SBF (b, c, d, and e). b and c contain TCP. a, d and e have the strontium equivalent. Images on the right (c and e) have 10% PLS whilst those on the left (a, b, d) have 2% PLS.

From SEM (FIG. 6) a precipitate was observed on the surface of all specimens stored in SBF. Raman spectroscopy confirmed this to be primarily hydroxyapatite. This was more homogeneous when tristrontium phosphate instead of tricalcium phosphate was used (FIG. 6, bottom panels d and e), and covered a greater percentage of the surface. Furthermore the layer was thicker when the PLS level was higher (FIG. 6, right panels c and e). The formulation with high PLS and TCP (FIG. 6,c) has obvious defects in the underlying material surface on the right of the image and a rough precipitated hydroxyapatite layer on the left. Thicker layers were more likely to become cracked during processing for SEM. The difference in mass change in water and SBF suggested the layer was 4 and 1.5% of the mass of the samples with 10 and 2 wt % PLS respectively (FIG. 5).

These data show that addition of PLS in the formulations of the invention can provide control over water sorption, brushite formation and the thickness of layers of calcium phosphate and hydroxyapatite that form on the surface of the composite.

Example 4

Chemical Cured Composites for Bone Repair

Testing of Commercial Products

FTIR was used to determine the monomer conversion time for a number of commercial cements and composites. As shown in Table 2, commercial PMMA cements Palacos and Simplex P and bone composites Cortoss and Comp06 exhibited a delay time $t_{inh}$ before reaction, which provides the clinician with "working time". The time for half maximum reaction varied between 232 and 416 s. Final methacrylate conversion was over 50% for the composite cements as required for dimethacrylates. With the PMMA cements, conversion was less than 100% indicating significant unreacted MMA which can reduce cell compatibility.

Figure 14:
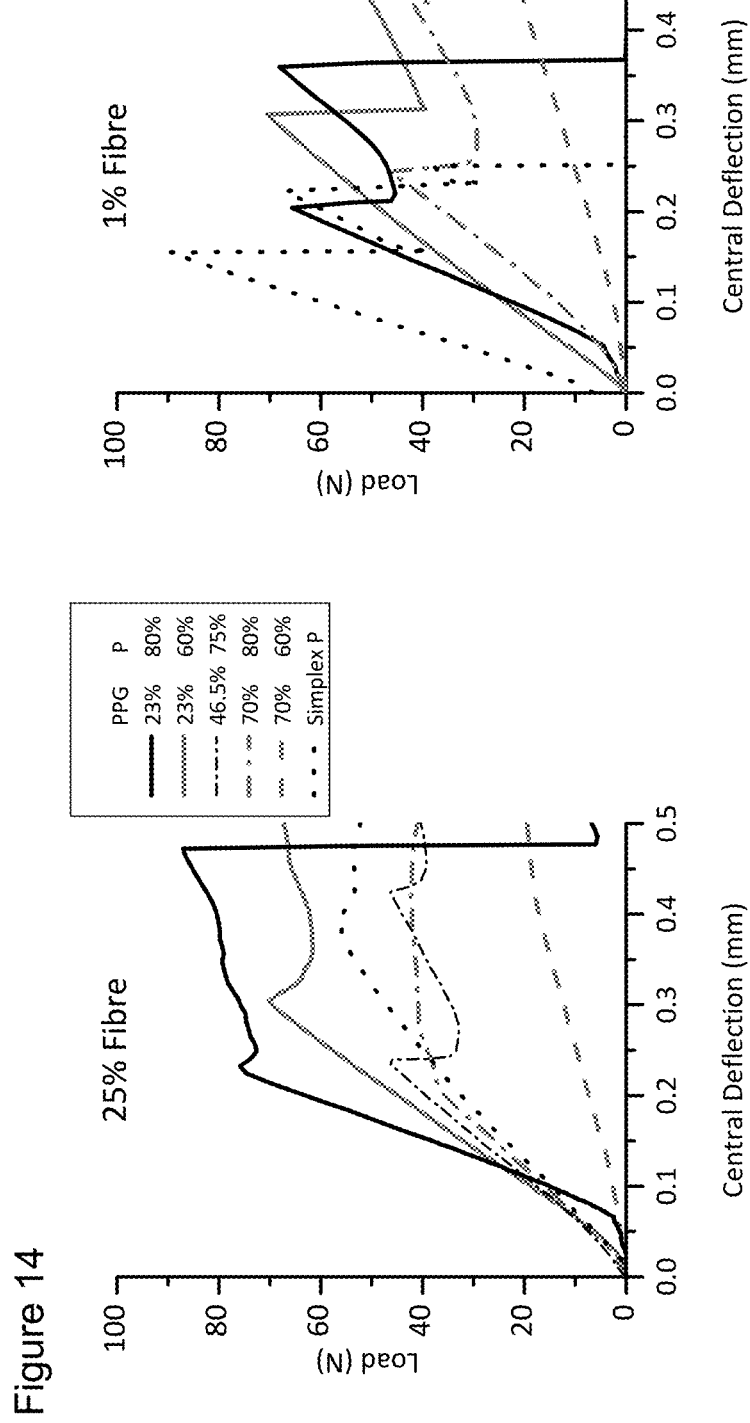
FIG. 14: Example load versus dentral deflection of experimental and commercial bone cements

Biaxial flexural strength of dry samples varied between 115 and 145 MPa. Modulus of the PMMA cements was advantageously lower than for the composites (Table 2). The PMMA cements also exhibited some plastic deformation after a yield point whereas the commercial composites exhibited brittle fracture and low toughness (FIG. 14).

TABLE 2

Final conversion, working time, time of half reaction, (at 25 C) biaxial flexural strength and modulus of commercial PMMA (Palacos and Simplex P) and composite (Cortoss and Comp06) bone cements.

| Product Name | Conversion (%) | $t_{inh}$ (s) | $t_{0.5}$ (s) | BFS (MPa) | Modulus (GPa) |
|---|---|---|---|---|---|
| Palacos | 86 ± 2 | 170 ± 16 | 281 ± 19 | 145 ± 17 | 1.6 ± 0.1 |
| Simplex P | 76 ± 1 | 276 ± 29 | 406 ± 28 | 126 ± 7 | 1.6 ± 0.1 |
| Cortoss | 64 ± 4 | 130 ± 29 | 232 ± 21 | 115 ± 9 | 3.4 ± 0.1 |
| Comp06 | 64 ± 0 | 171 ± 17 | 416 ± 15 | 140 ± 11 | 3.1 ± 0.2 |

Composites with Reactive CaP, CHX and PLS

PLS containing reactive filler composites were prepared using a fluid phase of 70% UDMA, 25% TEG-DMA, 5% HEMA, 300 ppm BHT DMPT 0.5% BP 0.5%. 25 wt % of this monomer was combined with 75 wt % powder filler. The filler consisted of Polylysine (1 or 10 wt %), Chlorhexidine (0 or 10 wt %), MCPM/TCP (CaP=10 or 20 wt %) and the remainder inert silane treated barium alumino silicate glass particles (Sci Pharm).

FTIR showed that addition of high levels (20 wt %) reactive calcium phosphates (CaP) can substantially increase the inhibition period and slow down the subsequent setting reaction. This problem was overcome by the addition of high chlorhexidine (CHX) or polylysine (PLS) showing these can act as additional activators (Table 3). Reaction rate advantageously increased at 37° C. reducing the potential risk or uncured monomer or leakage into surrounding blood supply when applied in vivo (Table 4).

TABLE 3

Inhibition time and half-life of reactive filler composites at 26° C.

| CaP | CHX | PLS | Inhibition time (26° C.) (s) | | Half-life (s) | |
|---|---|---|---|---|---|---|
| (wt % of powder) | | | | | | |
| 20 | 10 | 10 | 149 | ±1 | 295 | ±1 |
|  |  | 1 | 119 | ±3 | 267 | ±4 |
|  | 0 | 10 | 151 | ±13 | 479 | ±20 |
|  |  | 1 | 1083 | ±46 | 2475 | ±50 |
| 10 | 10 | 10 | 123 | ±4 | 263 | ±5 |
|  |  | 1 | 92 | ±4 | 216 | ±7 |
|  | 0 | 10 | 115 | ±3 | 329 | ±5 |
|  |  | 1 | 141 | ±6 | 442 | ±10 |

TABLE 4

Inhibition time and half-life of reactive filler composites at 37° C.

| CaP | CHX | PLS | Inhibition time 37° C. (s) | | Half-life (s) | |
|---|---|---|---|---|---|---|
| wt % of powder | | | | | | |
| 20 | 10 | 10 | 79 | ±4 | 155 | ±7 |
|  |  | 1 | 63 | ±4 | 138 | ±4 |
|  | 0 | 10 | 99 | ±2 | 219 | ±12 |
|  |  | 1 | 248 | ±10 | 522 | ±9 |

Figure 7:
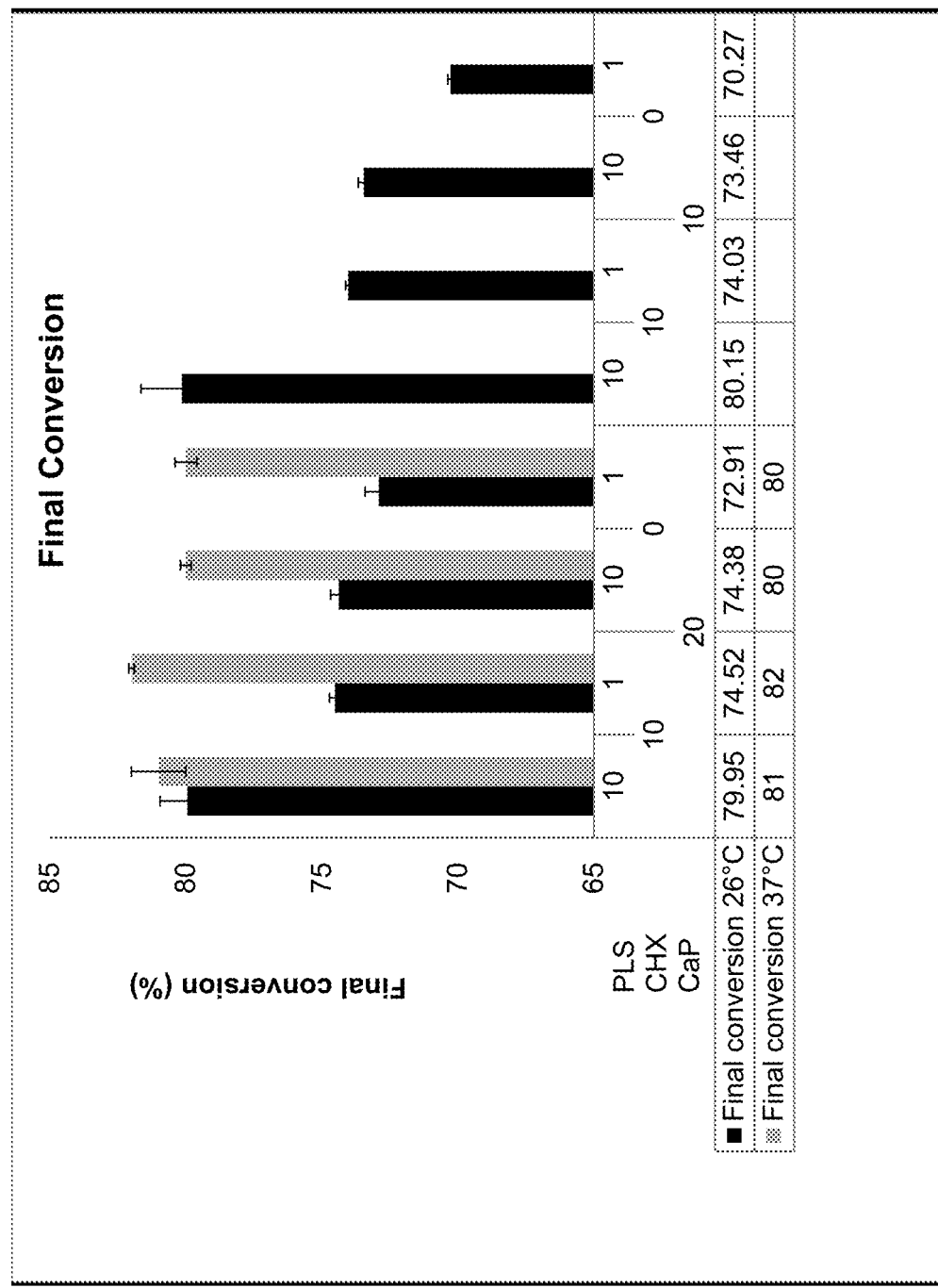
FIG. 7: Final conversion of chemical cured bone composites containing UDMA, TEGDMA, DMPT, PLS (1 or 10 wt %), CHX (0 or 10 wt %) and CaP (10 or 20 wt %)

The final conversion of chemical cured bone composites containing UDMA, TEGDMA, DMPT, PLS (1 or 10 wt %), CHX (0 or 10 wt %) and CaP (10 or 20 wt %) was measured using FTIR, as shown in FIG. 7. Both CHX and PLS increased final monomer conversion, and showed synergy when both CHX and PLS were present at higher concentrations (FIG. 7). The conversions achieved of 70 to 80% are also much higher than observed with the commercial bone composites (see Table 2), which would improve biocompatibility.

Figure 8:
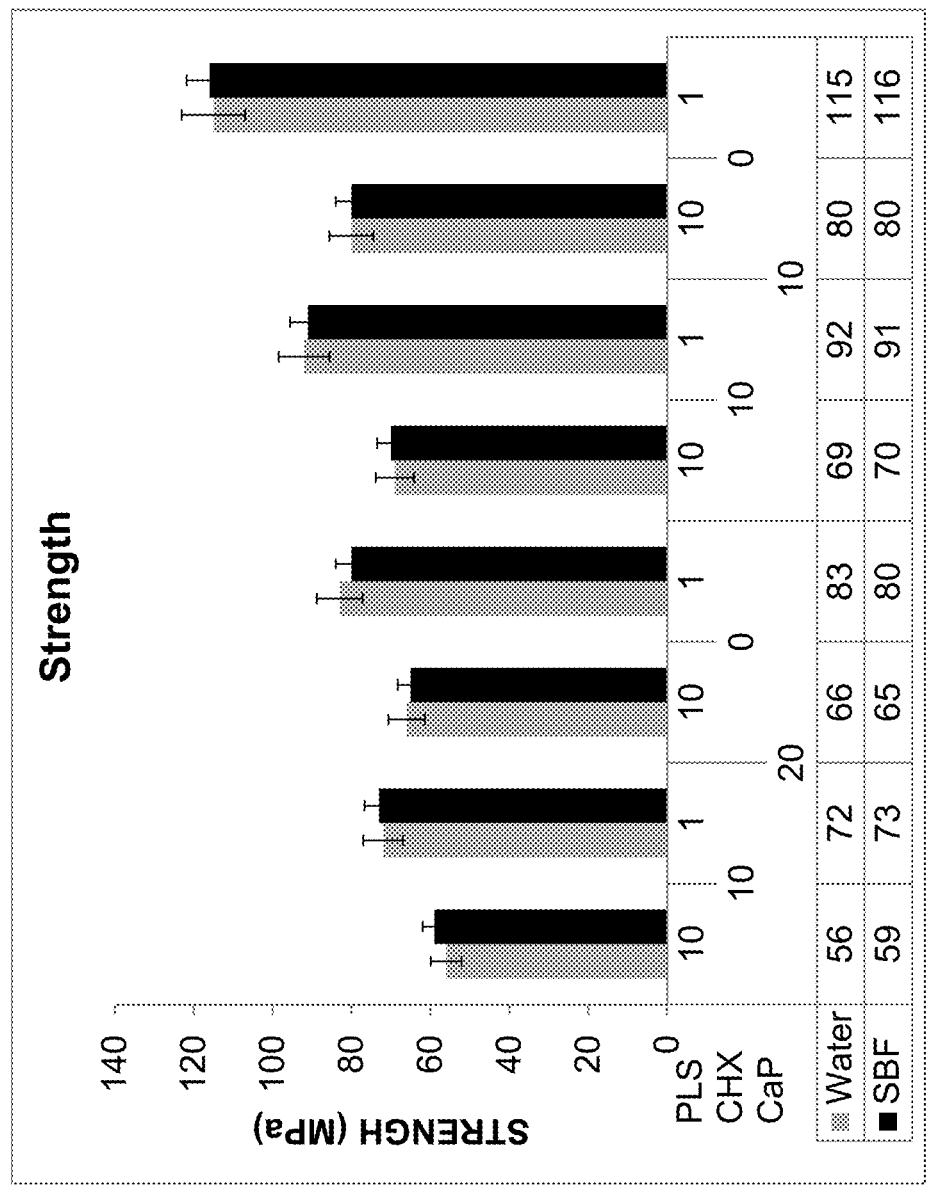
FIG. 8: Biaxial flexural strength and modulus of formulations shown in FIG. 7.
Figure 8:
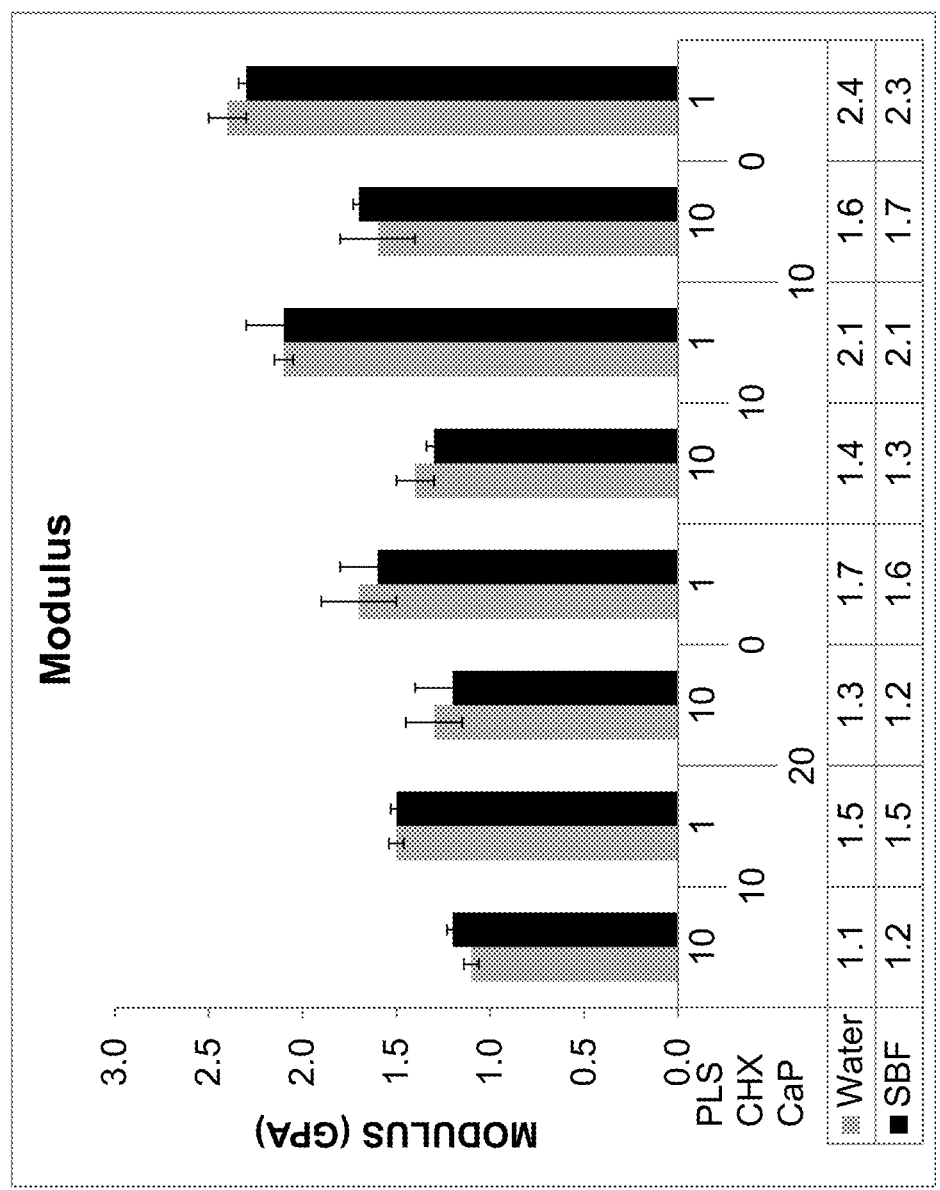

FIG. 8 shows the biaxial flexural strength and modulus after 24 hours in water or SBF. High PLS and CHX can somewhat decrease strength, however they also reduce stiffness (modulus), which could advantageously prevent bone stress shielding, raise resilience and bonding capability. However, formulations with low CaP and PLS, but no CHX, have comparable strength to commercial bone composites but additionally lower modulus and the advantages of lower modulus described above.

Example 5

Antibacterial Release Rates

Reactive filler composites containing PLS were prepared as 1 mm thick composite discs. The fluid phase contained 70% UDMA, 25% TEG-DMA, 5% HEMA, 300 ppm BHT, DMPT 0.5%, BP 0.5%. 25 wt % of this fluid phase was combined with 75 wt % powder filler. The filler contained polylysine (1 or 10 wt %), chlorhexidine (0 or 10 wt %), MCPM/TCP (CaP=10 or 20 wt %) and the remainder glass particles (Sci Pharm).

The release rate of CHX and PLS in water was determined over a period of 6 weeks, as shown in FIG. 9.

Figure 9A:
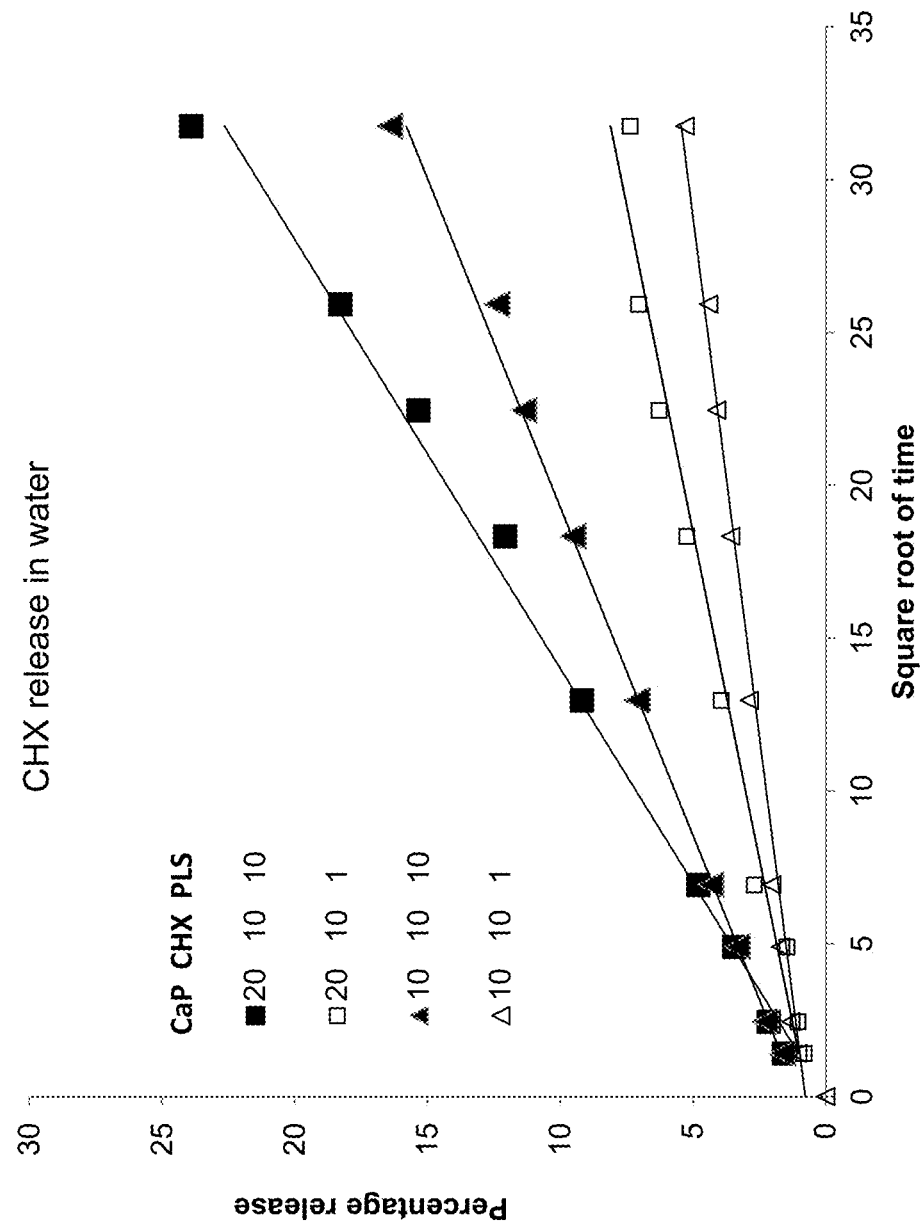
FIG. 9: Release of agent versus square root of time of a) CHX and b) PLS for composites containing CaP (10 or 20 wt %), CHX (0 or 10 wt %) and PLS (1 or 10 wt %)

CHX release increased upon raising both CaP and PLS percentages in reactive filler composites. The level of release was proportional to the square root of time as expected with a diffusion controlled process (FIG. 9a). These data show that PLS enhances CHX release. In vitro studies have demonstrated that very low CHX release from dental materials can totally prevent bacterial penetration between the material and dentine, and therefore the composites of the invention comprising CHX would have effective anti-bacterial properties. By contrast, CHX release from conventional dental composites or GICs is very low, and requires high drug content which usually decreases material strength.

Figure 9B:
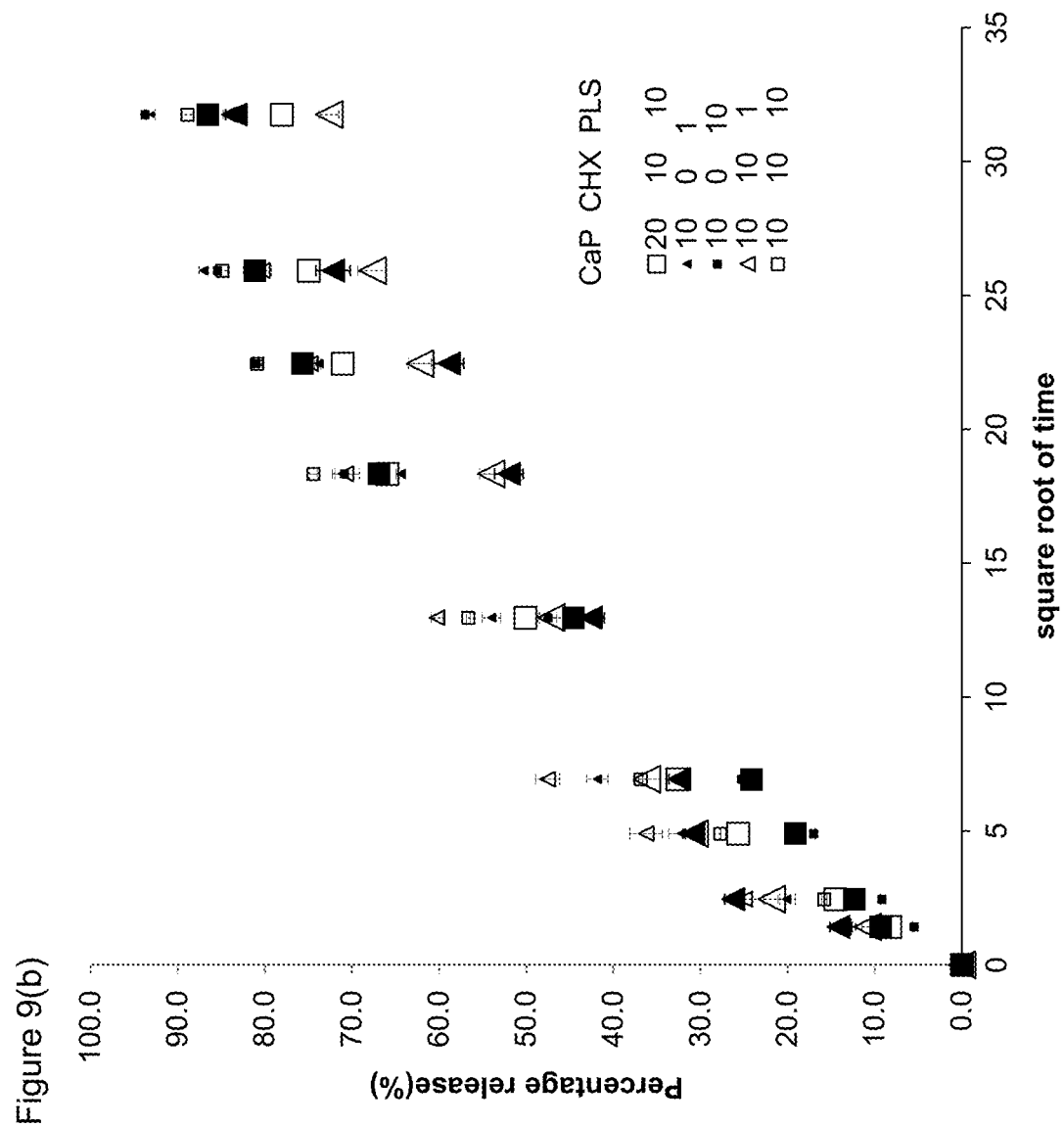

Higher percentages of PLS (over 70% of that in 1 mm thick composite discs) were released over a period of 6 weeks than CHX. Release percentage was approximately proportional to the square root of time initially but tended to 100% at later times (FIG. 9b).

Example 6

Mass Change in SBF Vs Water

Figure 10A:
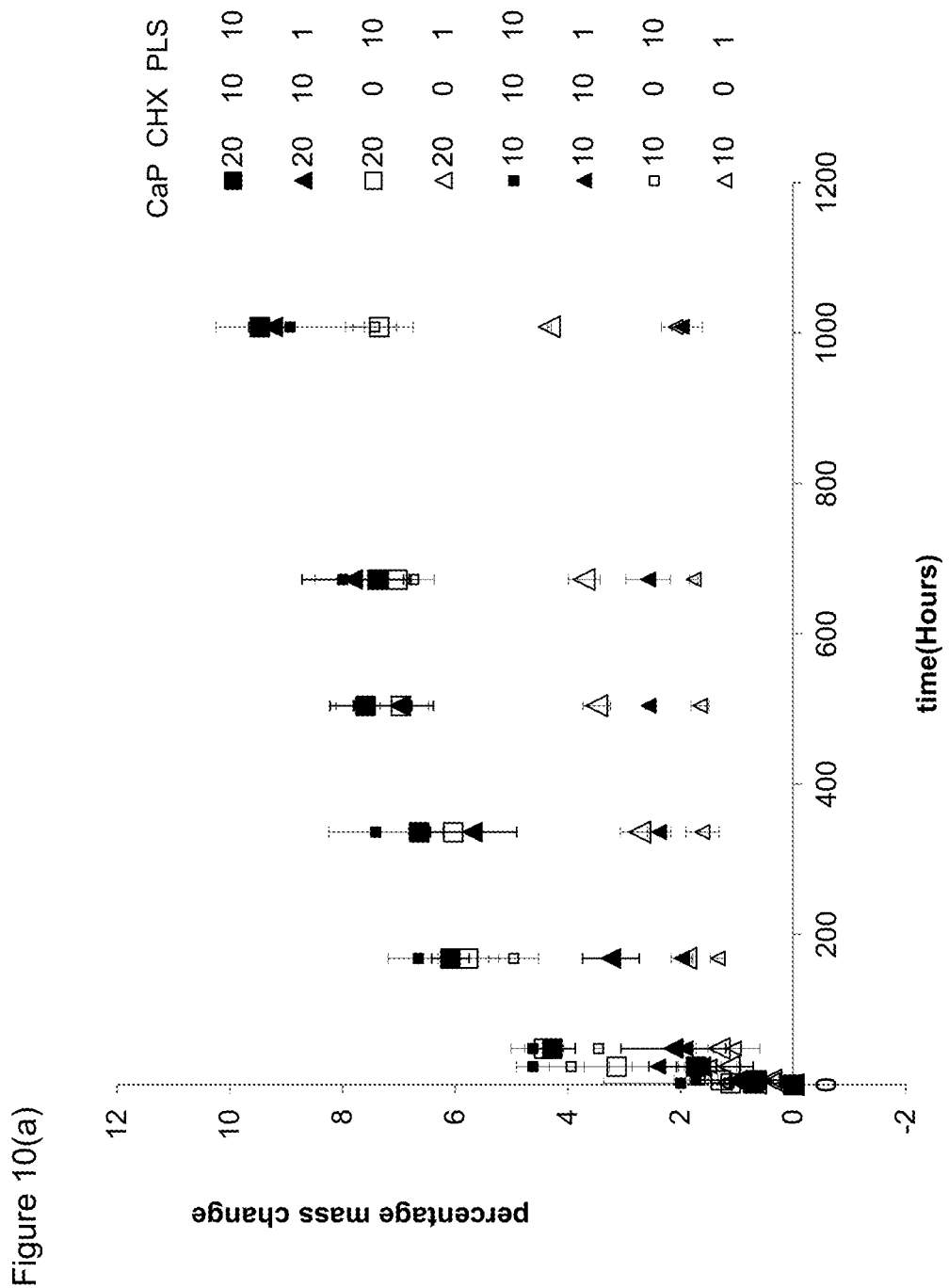
FIG. 10: Percentage mass change a) versus time in SBF and b) at 6 weeks in SBF and water.
Figure 10B:
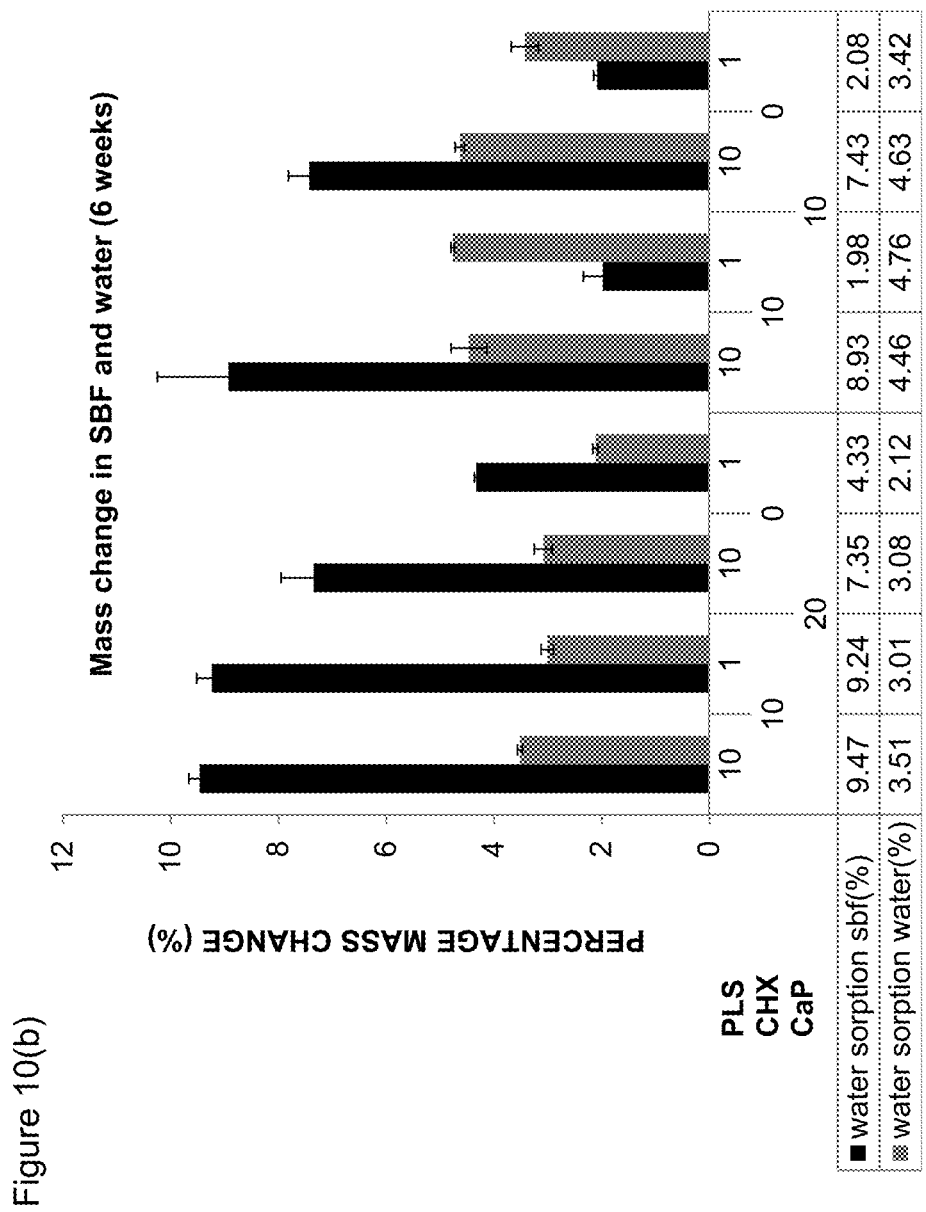
Figure 11:
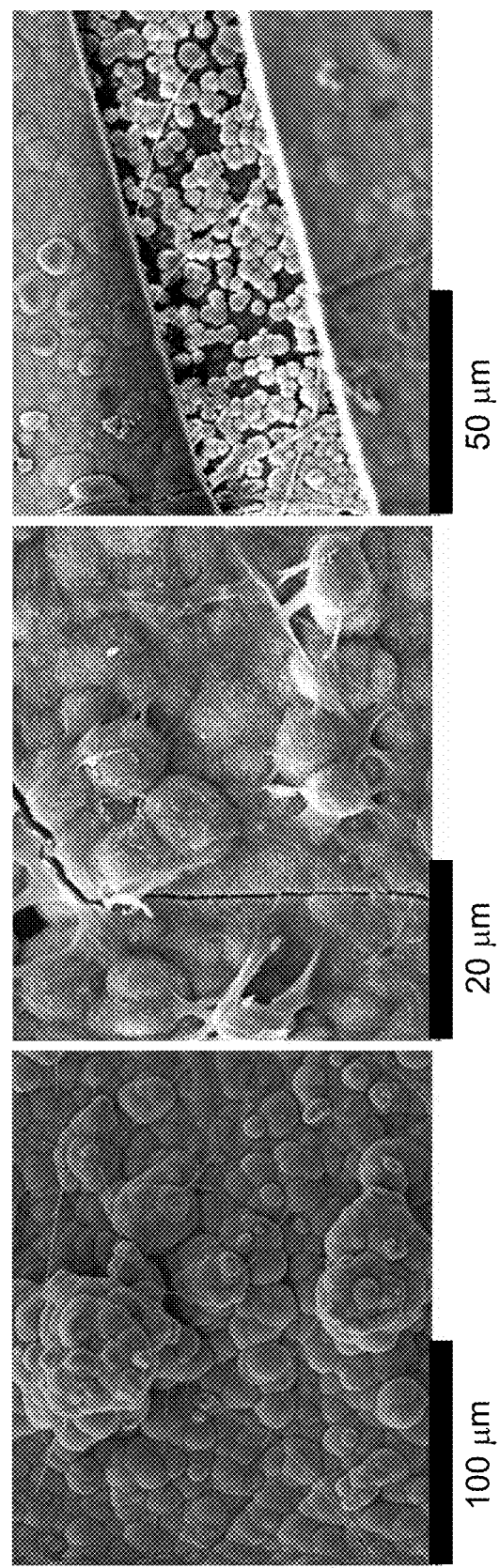
FIG. 11: SEM images of hydroxyapatite formation on the surfaces of PLS containing reactive filler composites. This intermingles with ropes of PLS. Cracks in the hydroxyapatite layer can repair with time.

The reactive filler composites of Example 5 were placed in water or simulated body fluid (SBF) to determine changes in mass and structure over time. In SBF, higher levels of PLS (10 wt %) significantly enhanced mass increase compared to formulations with lower (1 wt %) PLS. Formulations with lower CaP (10 wt %) increased more in weight in water than in SBF due to osmotic pressure difference encouraging greater water sorption in the former (FIG. 10b). Samples with high PLS increased significantly more in mass in SBF than in water, and this was particularly apparent at low CaP (10 wt %) or in the absence of CHX. Most of the mass increase occurs in the first 24 hours (FIG. 10a). SEM images (FIG. 11) show this is due to the formation of a hydroxyapatite/PLS layer that is similar to dentine/bone. A significant advantage of this is that if it becomes cracked, the layer can reform. PLS can also be detected within this layer.

Example 7

Optimisation of Initiator and Activator in Composites Produced Using NTGGMA

"Chemical curing" composites for bone repair were prepared using 70% UDMA, 25% TEG-DMA and 5% HEMA, BP and NTGGMA. Initiator and activator concentrations ranged between 0.25 and 1 wt % in the final mixed paste. Glass powder from barium aluminosilicate glass (DMG) was included at 75 wt %.

Results

Conversion—FTIR results show that NTGGMA can replace DMPT as an activator.

Additionally, faster reaction after a given start time for the reaction was seen in composites with NTGGMA than seen using DMPT in the PPGDMA materials described above (Table 5). Greater final conversion was obtained with higher initiator and activator levels without high loss of working time at room temperature. Reaction rate and final conversion were advantageously greater at body temperature. Higher conversion should improve wear but also raise strength and modulus.

TABLE 5

Polymerisation start time, time of half reaction and final conversion of TEGDMA containing composites prepared using varying levels of BP and NTGGMA at a) 26° C. and b) 37° C.

| BP(wt % of monomer) | NTG-GMA (wt % of monomer) | Starting time (s) | Half-life (s) | Final conversion (%) |
|---|---|---|---|---|
| (a) | | | | |
| 0.25 | 0.25 | 1127 ± 32 | 1397 ± 47 | 62.3 ± 0.3 |
| 0.5 | 0.5 | 365 ± 21 | 523 ± 25 | 69.4 ± 0.6 |
| 0.5 | 0.75 | 292 ± 7 | 429 ± 6 | 71.6 ± 0.4 |
| 0.75 | 0.5 | 257 ± 5 | 393 ± 5 | 74.8 ± 0.3 |
| 0.75 | 0.75 | 197 ± 8 | 310 ± 7 | 74.6 ± 0.6 |
| 0.75 | 1 | 180 ± 6 | 292 ± 10 | 74.4 ± 0.2 |
| 1 | 0.75 | 125 ± 7 | 226 ± 5 | 74.5 ± 0.4 |
| 1 | 1 | 94 ± 7 | 180 ± 7 | 76.2 ± 0.5 |
| (b) | | | | |
| 0.25 | 0.25 | 612 ± 24 | 807 ± 24 | 74.7 ± 0.2 |
| 0.5 | 0.5 | 135 ± 8 | 222 ± 9 | 75.3 ± 0.4 |
| 0.5 | 0.75 | 108 ± 4 | 179 ± 9 | 76.8 ± 0.2 |
| 0.75 | 0.5 | 107 ± 4 | 186 ± 4 | 79.8 ± 0.2 |
| 0.75 | 0.75 | 60 ± 2 | 113 ± 7 | 80.0 ± 0.2 |
| 0.75 | 1 | 70 ± 3 | 122 ± 4 | 83.5 ± 0.2 |
| 1 | 0.75 | 54 ± 2 | 107 ± 3 | 83.3 ± 0.2 |
| 1 | 1 | 41 ± 2 | 98 ± 3 | 84.0 ± 0.2 |

Figure 12A:
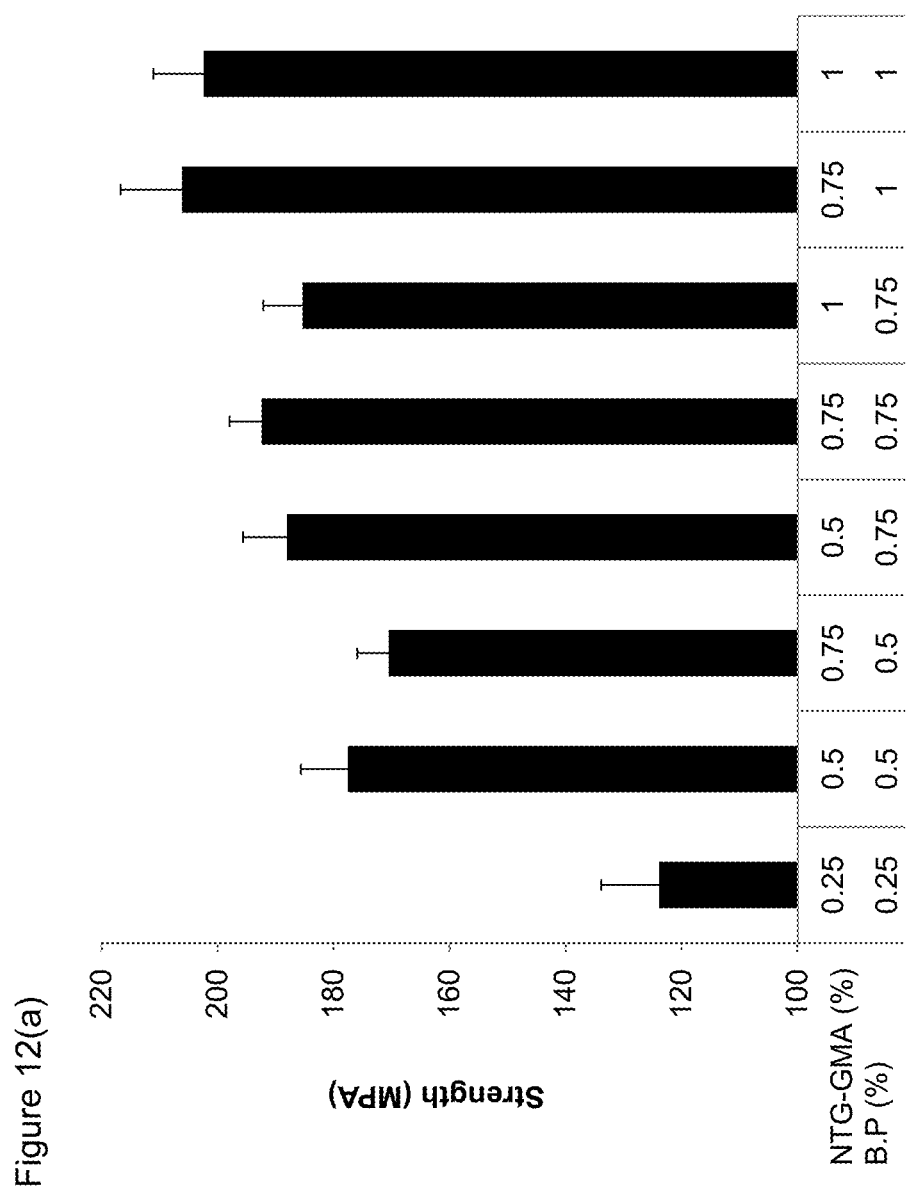
FIG. 12: Strength and modulus of composites produced using BP with NTGGMA at varying levels.
Figure 12B:
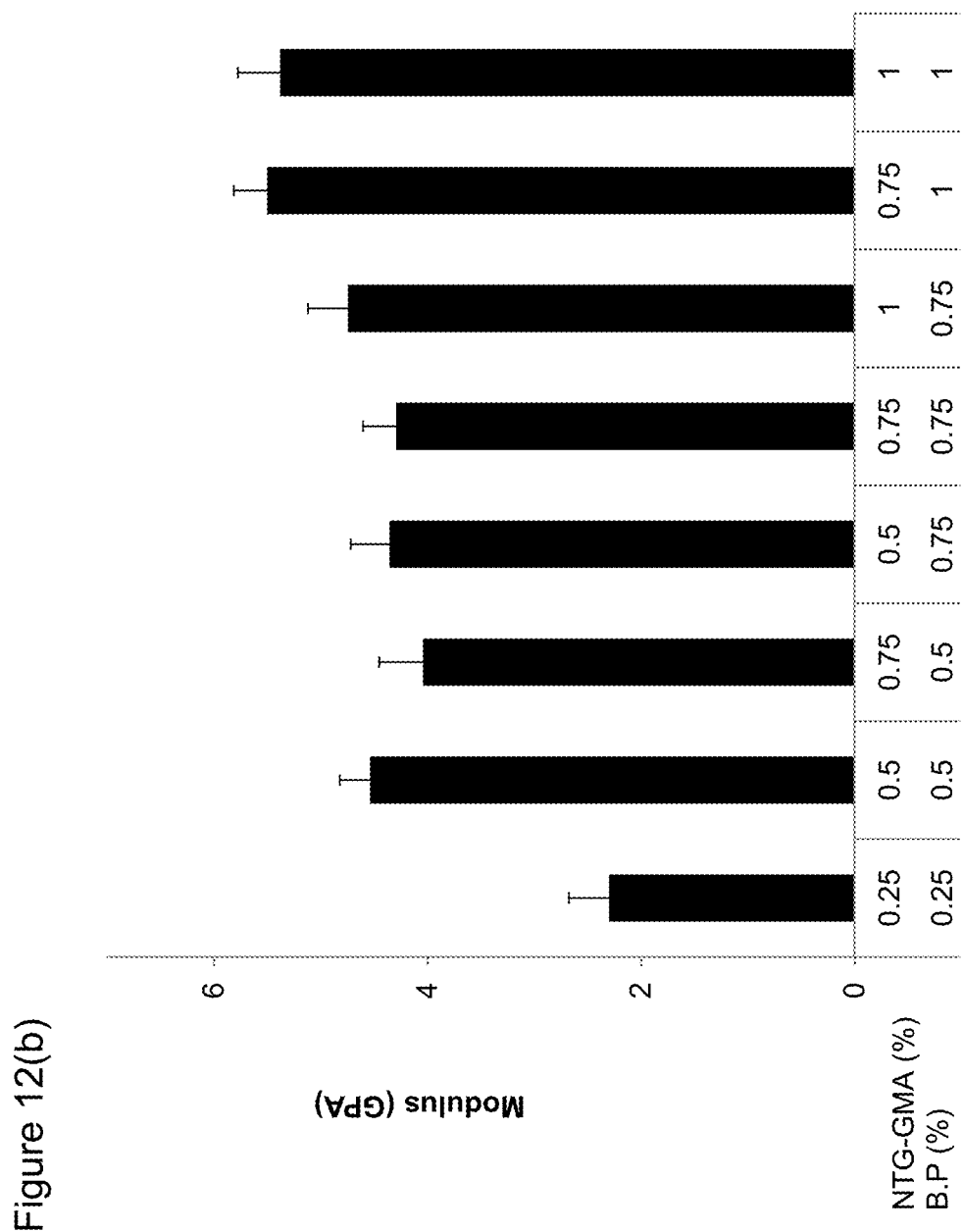

The flexural strength and modulus of these composites was measured as described above. As expected, the rise in monomer conversion with increasing NTGGMA level enabled a significant increase in strength (FIG. 12a). This, however, also increased modulus (FIG. 12b).

Example 8

Bone Composites with Fibres, Reactive CaP, PLS, CHX and NTGGMA

Monomer mixtures were prepared using 70 wt % UDMA, 25 wt % TEG-DMA and 5 wt % HEMA combined with 0.5 wt % B.P/DMPT or 0.75 wt % of B.P/NTG-GMA. The powder filler consisted of fibre (0 or 5 or 10 wt %), PLS (10 wt %), CHX (0 or 10 wt %), CaP (20 wt %) and glass powder to provide a total filler content in the formulation of 75 wt %. Samples were tested after 24 hours in water.

Mechanical Properties

Figure 13:
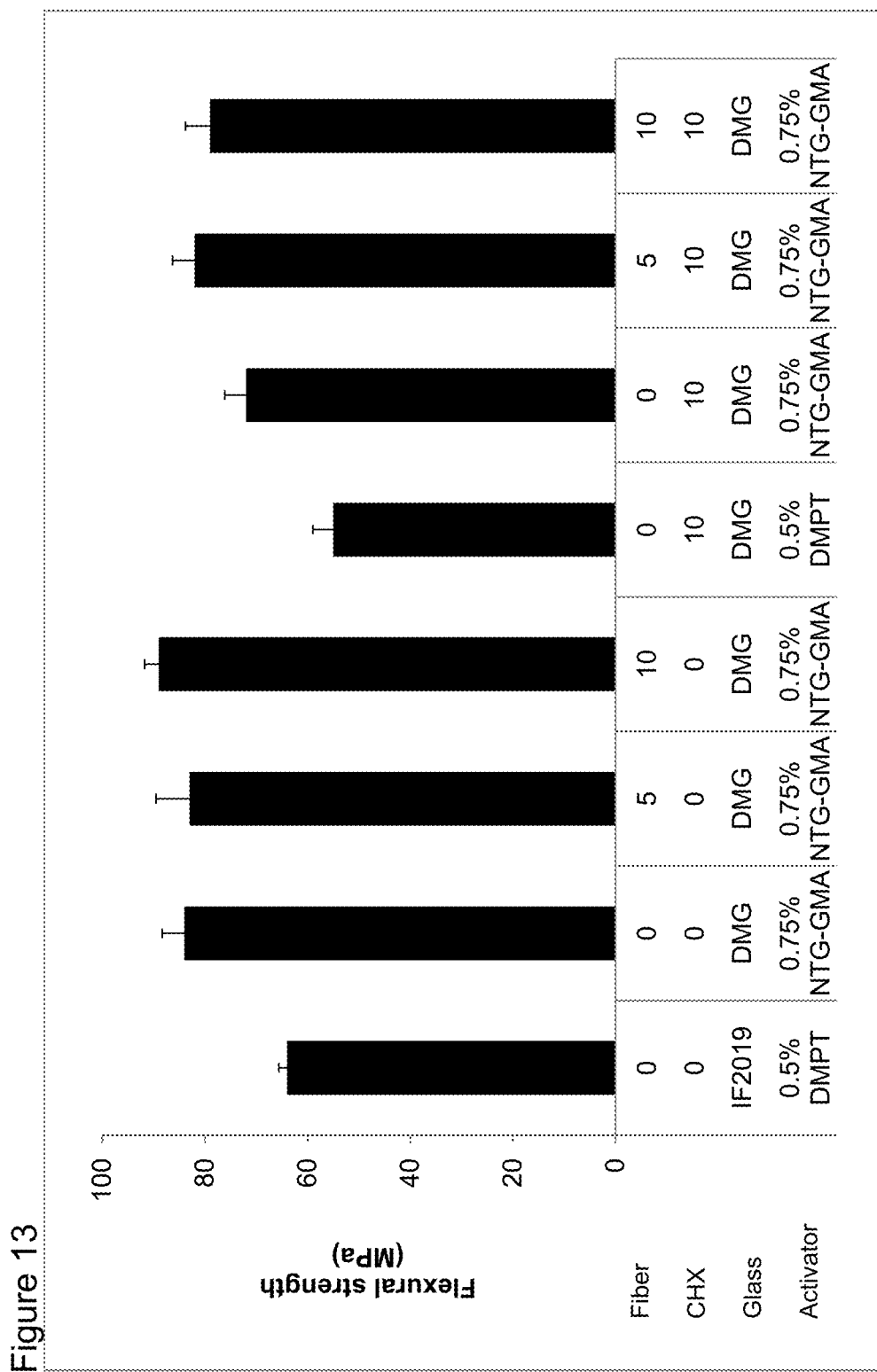
FIG. 13: Strength, modulus and toughness of bone composites containing fibres, reactive CaP (20 wt %), PLS (10 wt %) CHX and NTGGMA versus DMPT.
Figure 13:
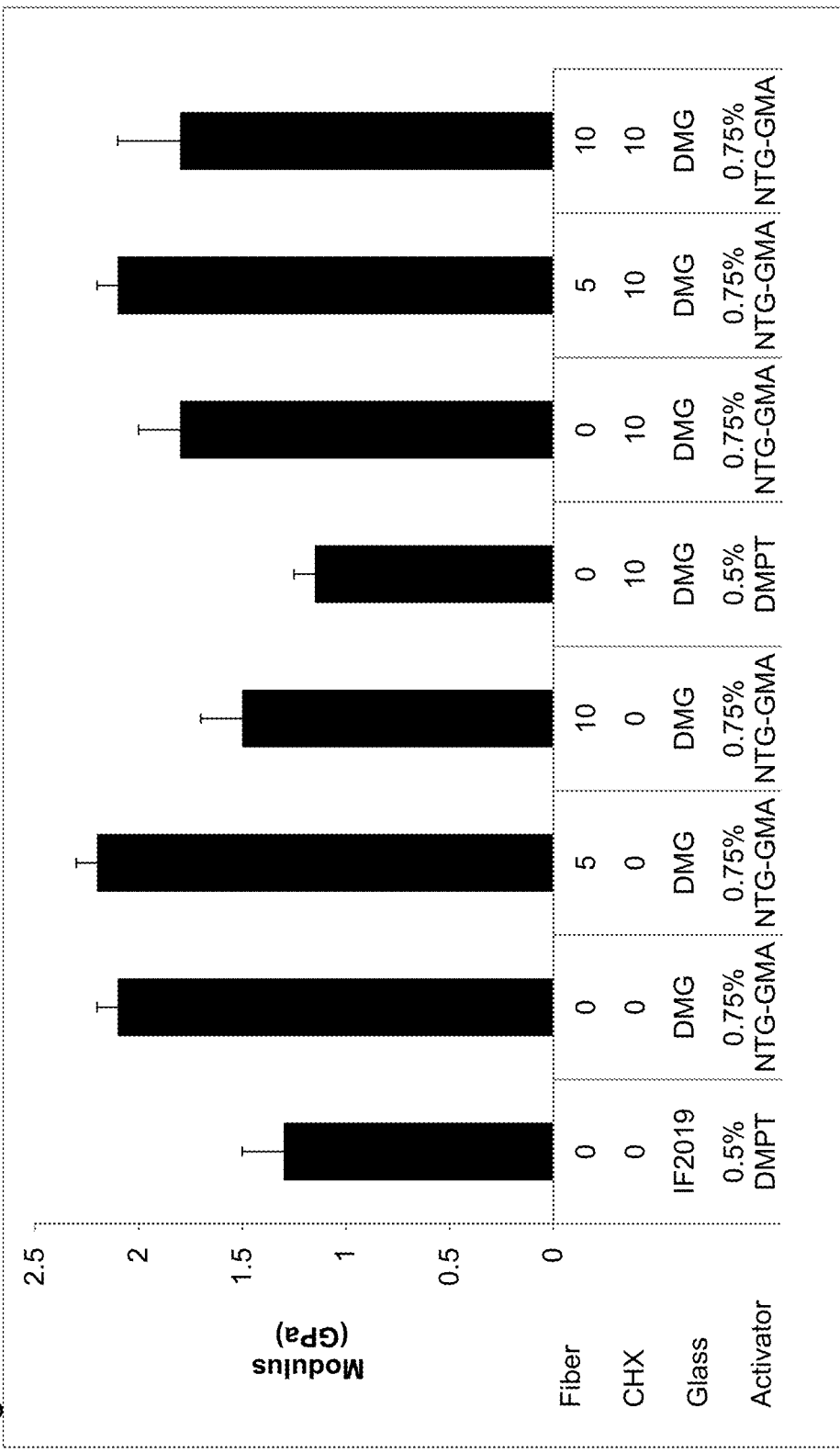
Figure 13:
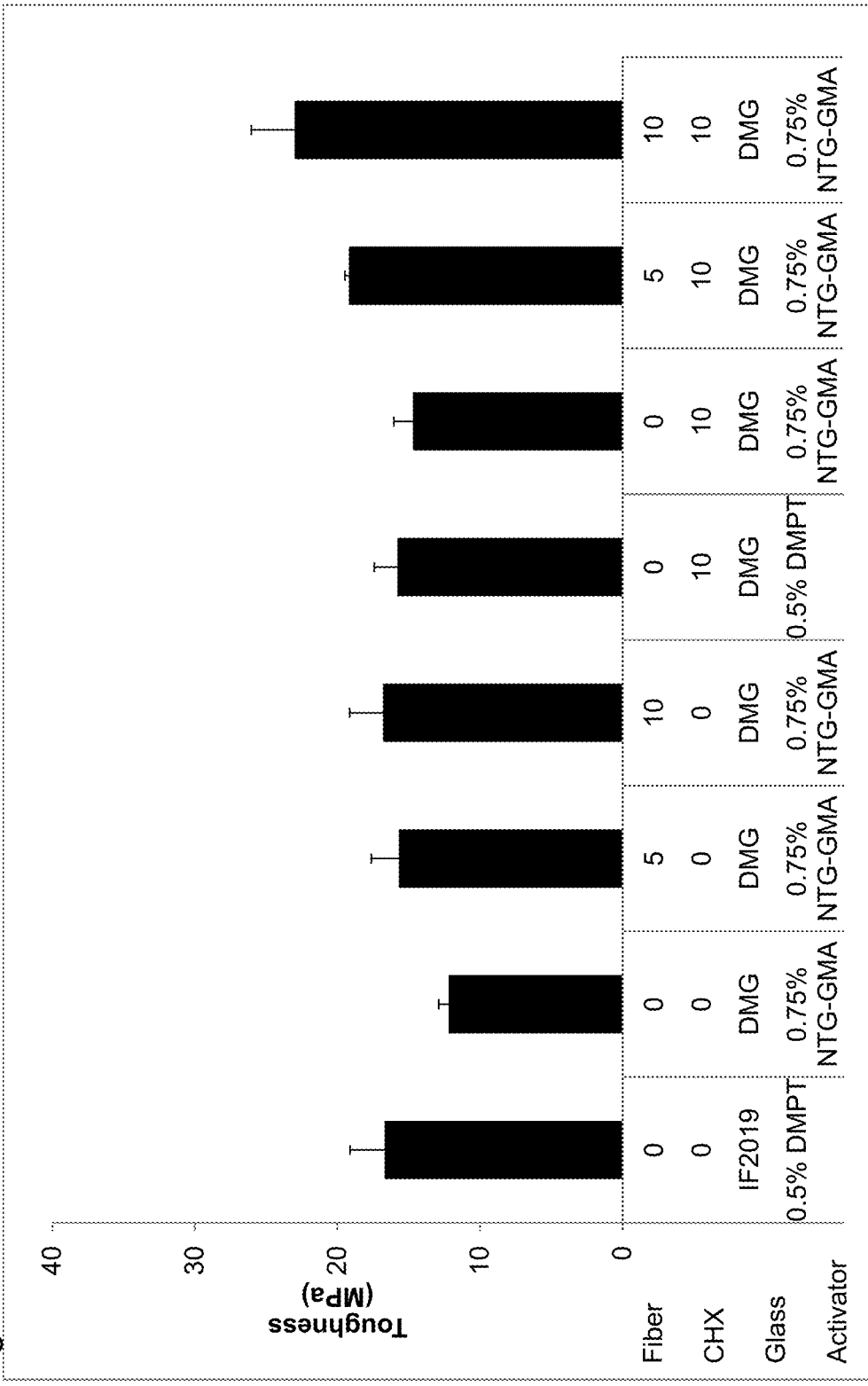

The flexural strength, modulus and toughness of these PLS-containing composites was measured as described above. The results showed that replacement of DMPT with NTGGMA can increase flexural strength of composites with high levels of reactive/active fillers (FIG. 13).

Example 9

Composites Prepared Using PPGDMA and Fibres

To produce chemical cure composites of lower modulus, formulations were prepared using the monomers and powders shown in Table 6. UDMA and PPGDMA contained approximately 150 and 100 ppm monomethyl ether hydroquinone (MEHQ) inhibitor respectively. In addition, UDMA and PPGDMA were supplemented with 70 and 170 ppm butylated hydroxyl toluene (BHT). 7 wt % Hydroxyethyl Methacrylate (HEMA, Esschem plc) glass powder and fibres were included. BP and DMPT were added both at 0.25 wt % as this gave cure times comparable with commercial products. For all experimental formulations, there was a delay equal to ⅓rd of the time for half reaction before any observable polymerisation reaction. Time for half reaction was enhanced with higher UDMA content or lower powder level. Calculated shrinkage (and therefore also heat generation) was lower for all materials than for the PMMA cement Simplex P. Final conversion was enhanced to over 95% by increasing PPG content.

strontium phosphate to produce materials that could treat osteoporosis and prevent infection.

Example 10

Brushite Cements with PLS (PAM)

Figure 16:
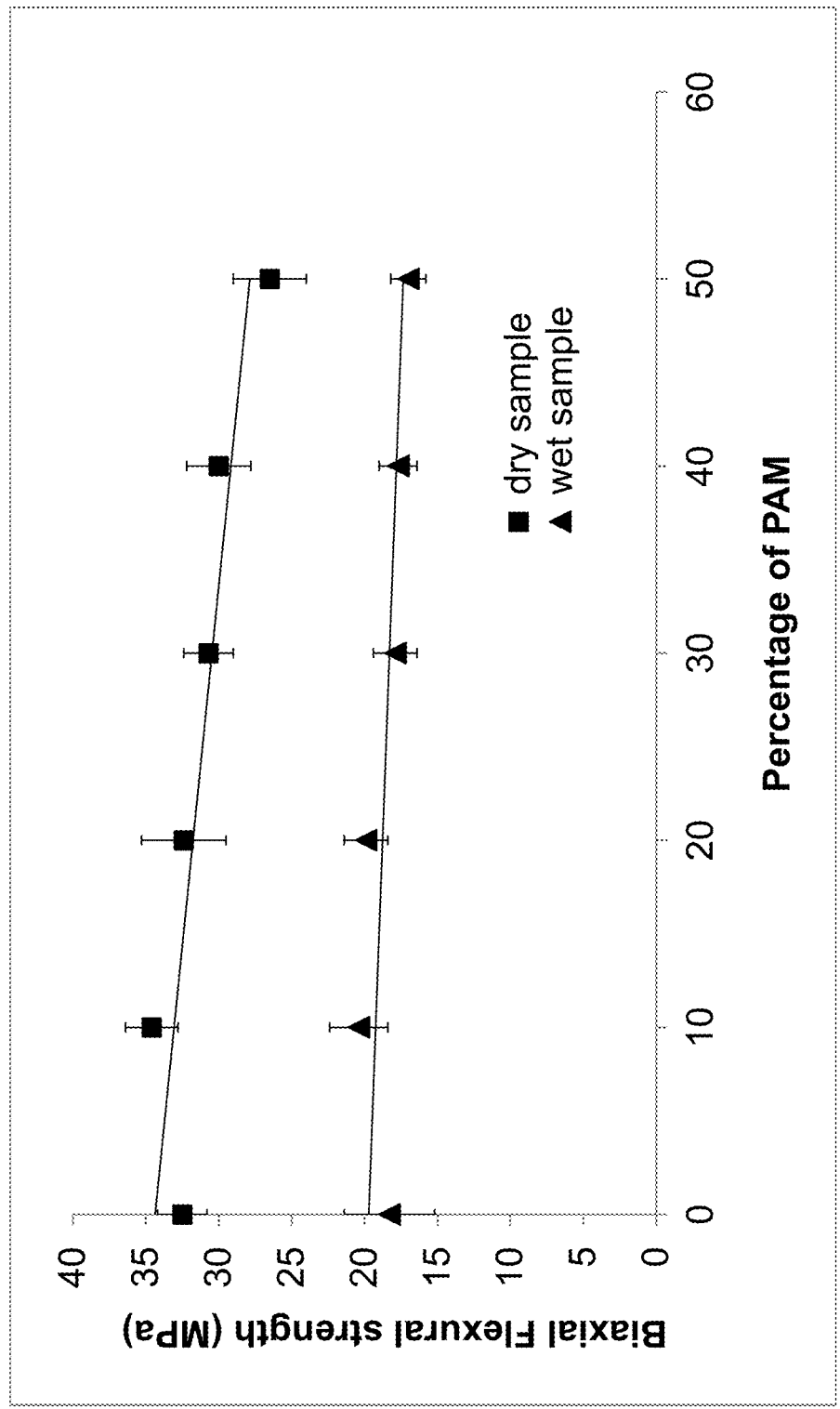
FIG. 16: Flexural strength and modulus of brushite cements containing up to 50 wt % PLS in the aqueous phase after dry storage or after 24 hours in water.
Figure 16:
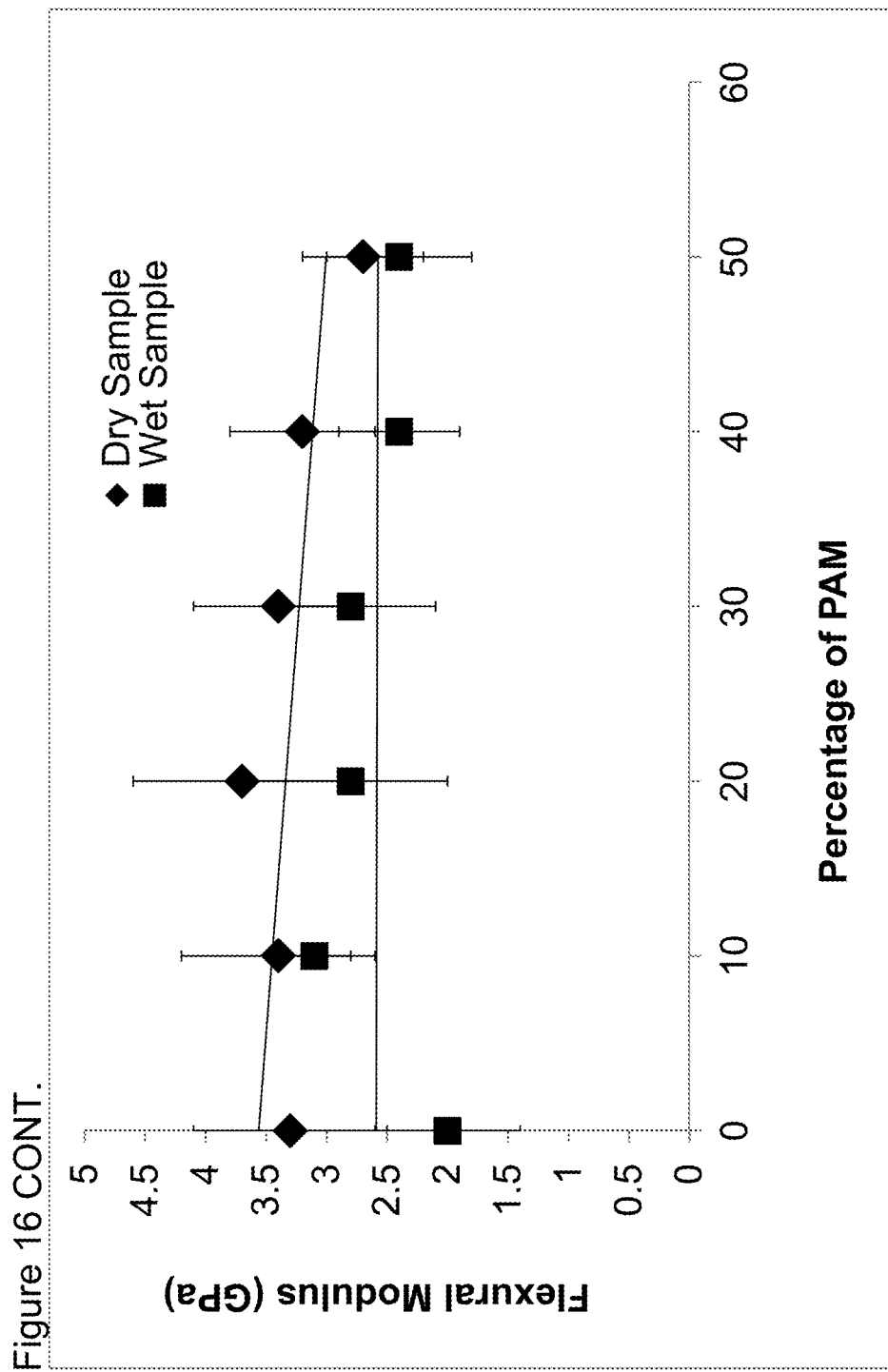
Figure 17:
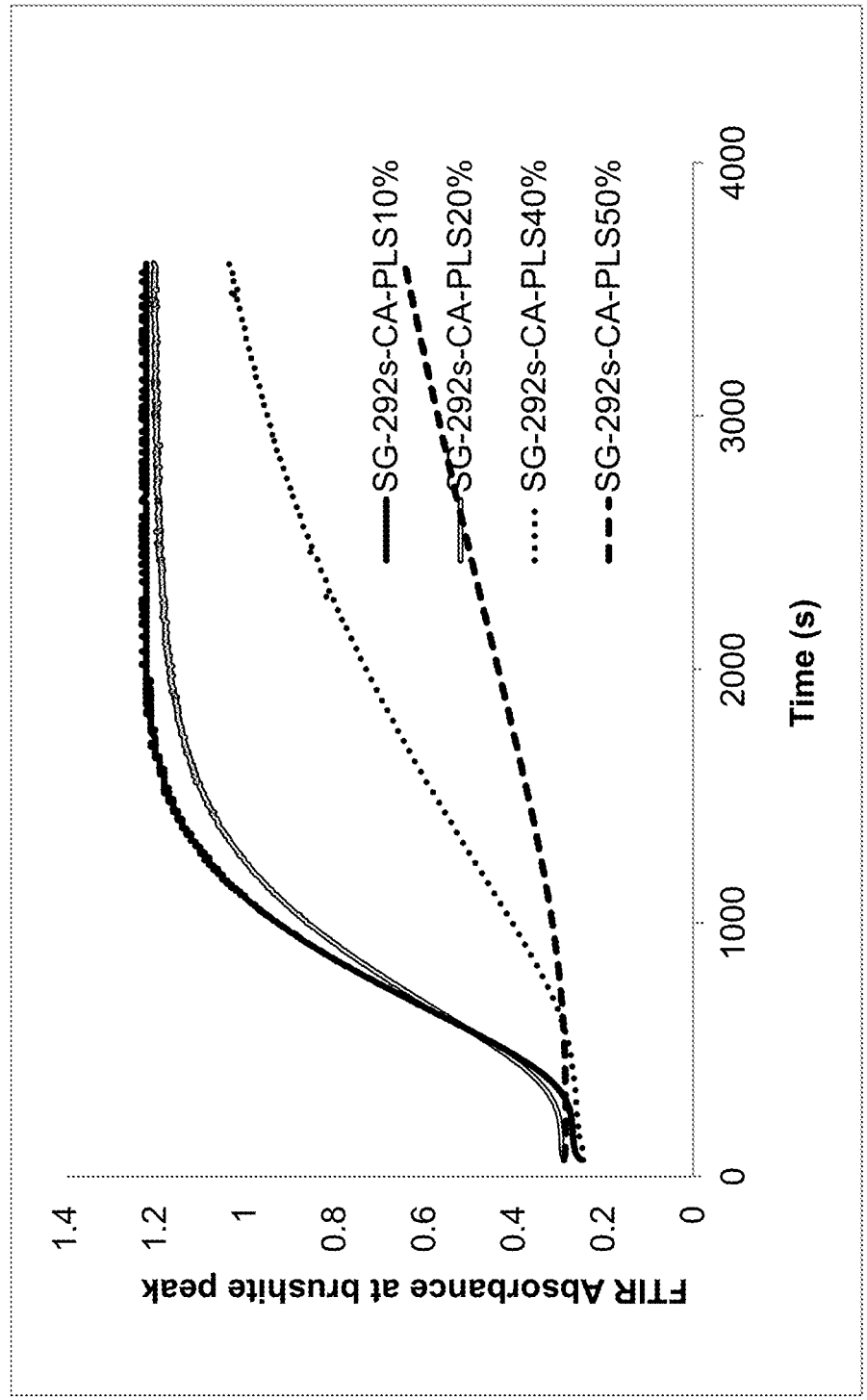
FIG. 17: FTIR absorbance versus time of set for brushite cements with 10, 20, 40 or 50 wt % PLS added into the aqueous phase showing time of brushite formation.

To prepare aqueous brushite cements, equimolar MCPM and TCP were combined with 800 mM aqueous citric acid at a powder to liquid ratio of 4:1 g/g. Mechanical studies showed that very high levels of PLS (up to 50 wt %) could be dissolved in this aqueous solution without significantly affecting the strength or modulus of the brushite cement after 24 hours in water (FIG. 16). These levels of antibacterial are very much higher than would generally be considered could be added to such cements. With high PLS the brushite cements were more cohesive. Furthermore they set more slowly suggesting that the citric acid setting retardant may be removed thereby potentially improving cell compatibility (FIG. 17).

Example 11

Composite Material for Tooth Restoration

These composites consist of blue light activated, cross-linking, methacrylate monomers with silica particles. In the invention, lower viscosity, larger, less irritant and more flexible and adhesion promoting monomers are employed with less toxic polymerisation initiators than in current commercial formulations. These should simplify bonding and reduce toxicity, shrinkage, bond damage and brittle fracture. Additionally, part of the filler phase is replaced by

TABLE 6

Composite bone cements: Methacrylates (PPG, UDMA and HEMA), powder and fiber contents are given as weight percentages of total monomer, composite or powder respectively. Results shown: conversion, $t_{0.5}$ and shrinkage. Errors are 95% confidence intervals. For Shrinkage, $t_{0.5}$ and Conversion n = 4.

|  | PPGDMA (wt. % of monomer) | UDMA | HEMA | Glass Powder (SciPharm) (wt. % of composite) | Glass fiber (wt % of powder) | Conversion (%) |  | $t_{0.5}$ (s) |  | Shrinkage (%) |  |
|---|---|---|---|---|---|---|---|---|---|---|---|
| PFC1 | 23 | 70 | 7 | 60 | 1 | 69 | ±3 | 114 | ±15 | 4.8 | ±0.2 |
| PFC2 |  |  |  |  | 25 | 71 | ±1 | 98 | ±4 | 4.9 | ±0.1 |
| PFC3 |  |  |  | 80 | 1 | 70 | ±1 | 214 | ±44 | 3.0 | ±0.0 |
| PFC4 |  |  |  |  | 25 | 73 | ±1 | 233 | ±15 | 3.2 | ±0.1 |
| PFC9 | 46.5 | 46.5 |  | 75 | 5 | 82 | ±4 | 163 | ±5 | 4.0 | ±0.2 |
| PFC5 | 70 | 23 |  | 60 | 1 | 96 | ±3 | 284 | ±12 | 5.9 | ±0.1 |
| PFC8 |  |  |  |  | 25 | 97 | ±5 | 240 | ±15 | 6.0 | ±0.3 |
| PFC7 |  |  |  | 80 | 1 | 95 | ±4 | 401 | ±79 | 3.7 | ±0.2 |
| PFC8 |  |  |  |  | 25 | 92 | ±4 | 337 | ±17 | 3.6 | ±0.1 |
|  |  | Cortoss |  |  |  | 64 | ±1 | 231 | ±12 | 3.7 | ±0.1 |
|  |  | Simplex P |  |  |  | 76 | ±1 | 406 | ±28 | 6.2 | ±0.1 |

The effect of raising glass fibre content on strength, modulus and toughness was measured. Raising Fibre content had no effect on strength or modulus but did substantially increase strain at break (FIG. 14).

Figure 15:
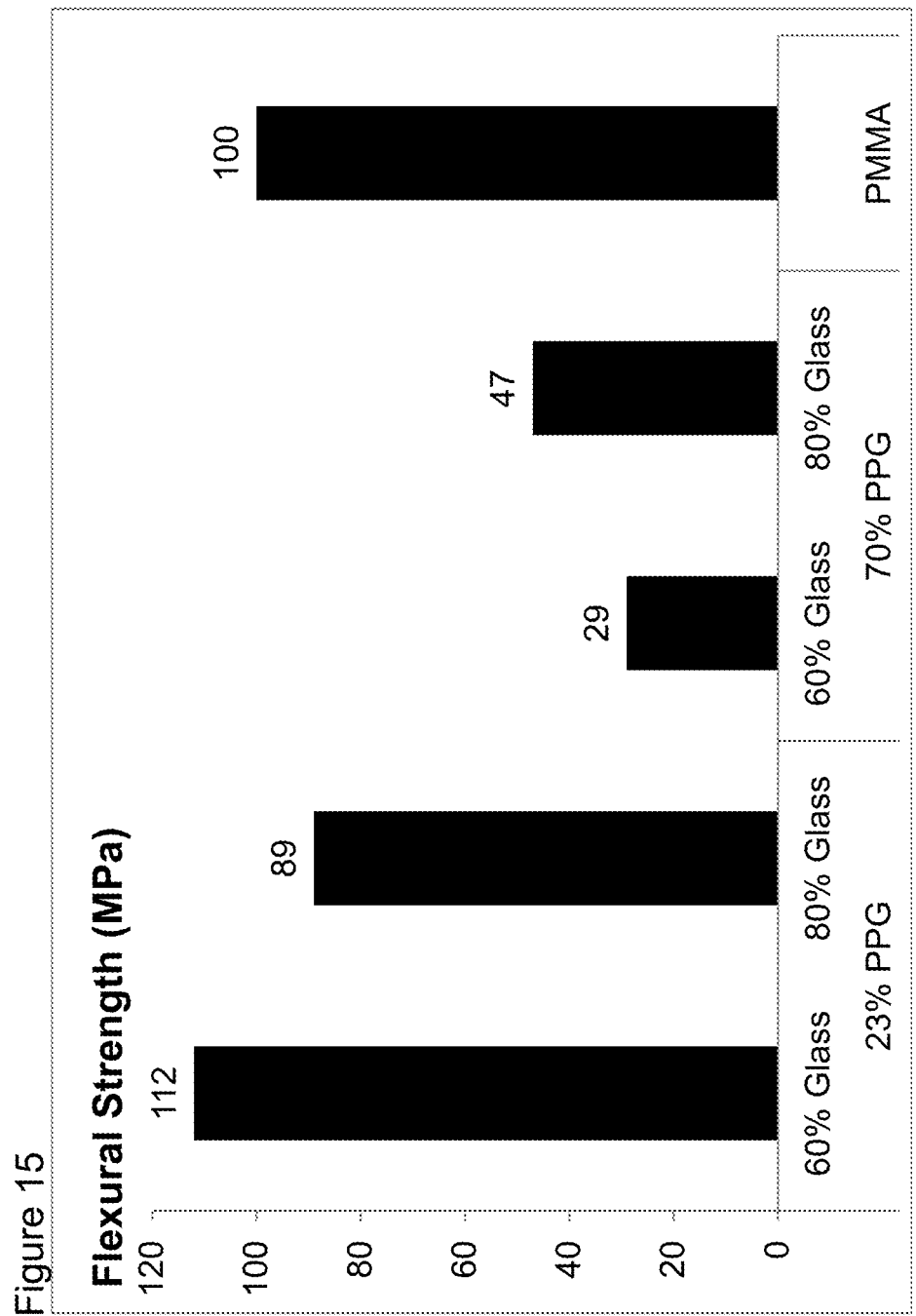
FIG. 15: Flexural strength and modulus of chemical cured composites produced using varying levels of PPGDMA with UDMA and varying levels of glass filler

The effect of PPG level on flexural strength and modulus was also determined. Increasing PPG level reduced strength but could also substantially reduce the modulus providing a tough instead of brittle material (FIG. 15). Stronger materials would be required for high load bearing bone repair applications. For vertebroplasty and screw augmentation, however, the lower modulus materials would be more suitable. These can be combined with gentamicin, PLS and re-mineralising reactive calcium phosphates to promote natural tooth repair. Moreover, antibacterial/enzyme inhibiting chlorhexidine (CHX) and less toxic polymeric antimicrobial (PAM) reduce tooth excavation need/recurrent caries. Furthermore, silica fibres can be included for toughening.

The above changes could reduce the need for use of the dental drill and anaesthetic and allow the dentist to perform more minimally invasive restoration. The dentist would then remove only the top surface infected dentine. They would leave the underlying affected (demineralised) dentine. The calcium phosphate precipitation would enable more natural repair of the affected dentine once all the bacteria have been sealed in/killed by the antibacterial agent release. The accumulation of antibacterial agent at the tooth restoration interface in combination with filling of any gaps at this interface with precipitating calcium phosphate would prevent longer term bacterial microlakage. Greater material flexibility and toughness would reduce strain on the bond. This should enhance restoration longevity which is a significant problem with current dental composites.

For children, higher levels of antibacterial, remineralising and plasticising components might be required as their teeth contain more dentine and less enamel. The reduced need for tooth excavation would be particularly advantageous. For adult tooth restoration stronger materials with lower active components might be required for restoration of teeth subjected to higher occlusal load.

Lower viscosity antibacterial and drug releasing adhesives could be obtained by complete removal of the silica and calcium phosphate particles from the above composites. This would be beneficial for applications where tissue remineralisation is not required or less of an issue. It would provide more flexible materials which should improve adhesion. In this case, some of the methacrylate monomer could be replaced by prepolymerised polymer beads as in PMMA cements to reduce polymerisation shrinkage and heat generation upon in vivo placement.

Increasing the active components further and removing the silica particles from the above invention would provide materials that are more suited for bonding of for example orthodontic brackets and crowns. With the orthodontic adhesive, the antibacterial and remineralising agents would help overcome difficulties arising with poorer teeth cleaning. The antibacterial and remineralising agents under the crowns could help remineralise the tissue that may have been demineralised using acid to provide a rougher surface for improved bonding. Lower glass content formulations could also be used as fissure sealants to prevent caries ever forming.

Replacement of the light cure initiators in the above dental restoration materials with chemical cure initiators provides materials to replace PMMA in vertebroplasty, hip and knee replacement surgeries and screw augmentation procedures. Additionally, use of more flexible monomers (eg replacement of TEGDMA by PPGDMA and BISGMA by UDMA) could provide more suitable materials than current bone composites for vertebroplasty. This could reduce the current problem of fracture of adjacent vertebra after vertebroplasty. Furthermore, greater remineralising potential and addition of strontium could help to reduce this problem and improve bone/material interlocking. The flexible monomers can also increase the level of filler that can be added. This reduces shrinkage and heat generation during cure which could reduce necrosis. Swelling of the material by water sorption promoted by reactive filler and cationic polymer addition could additionally help to reduce vertebral collapse.

Calcium phosphate cements of the current invention with polylysine could also be particularly beneficial for vertebroplasty, fixation of other low load bearing bones and drug delivery. The improved cohesive nature of the cement with polylsyine addition could help prevent leakage of the cement from the site of application. This is a particular hazard in vertebroplasty. Furthermore the combination of calcium phosphate with polylysine provides two mechanisms to enhance transfection if the device is used for Gene delivery. The new formulations could additionally provide better controlled release of small drugs (eg chlorhexidine and antibiotics) which are currently released too fast from conventional brushite cements.

Some of the advantages of the addition of polylysine in brushite cements arise due to the polymer replacing much of the aqueous phase whilst still maintaining initial fluidity. This reduces the porosity of the set cement which is known to enhance mechanical properties and slow release of drugs. Addition of polyacrylic acid can have a similar effect. We anticipate, however, that through combined use of polyacrylic acid and polylysine interactions between these two polymers would provide greater enhancement of mechanical properties. In particular the flexural strength should be raised but flexibility/modulus reduced.

Through the full replacement of water by a degradable methacrylate (eg PPGnLAmDMA) in the brushite cement a flexible rather than brittle formulation is achieved. These modifications make the materials more suitable as a bone glue. The addition of polylysine to such glues would impart antibacterial properties and encourage dynamic interaction with the surrounding healing bone. In addition, it could increase the rate of bone repair through encouraging hydroxyapatite precipitation and through interactions with polyacrylic acid groups formed upon degradation of the PPGnLAmDMA provide new mechanisms for "self repair" of the material.

Removal of the calcium phosphate from the above PPGn-LAmDMA with polylysine could provide degradable antibacterial adhesive materials more suited for repair of less or non mineralised tissues such as cartilage, skin, muscles, arteries and veins and organs such as liver, kidney, heart and lungs.

Example 12

Biaxial Flexural Strength and Apatite Formation on PLS and Reactive Calcium/Strontium Phosphate-Containing Dental Composites FIGS. 18-21 demonstrate the biaxial flexural strength (BFS), water sorption and apatite precipitation promoting ability of an optimised dental composite (F1) containing reactive calcium and strontium phosphates (CaSrP) in addition to polylysine (PLS). The formulation F1, consisted of a dental monomer phase UDMA/TEGDMA 3/1 with 5% 4META and light activated polymerisation initiators. This liquid was combined with 80 wt % powder. The powder consisted of a silanated barium alumino silicate dental glass, polylysine (PLS, 2.5%), tristrontium phosphate (15%) and monocalcium phosphate monohydrate (10%).

For control formulations F2, F3 and F4 the PLS, CaSrP or both were removed respectively.

Figure 18:
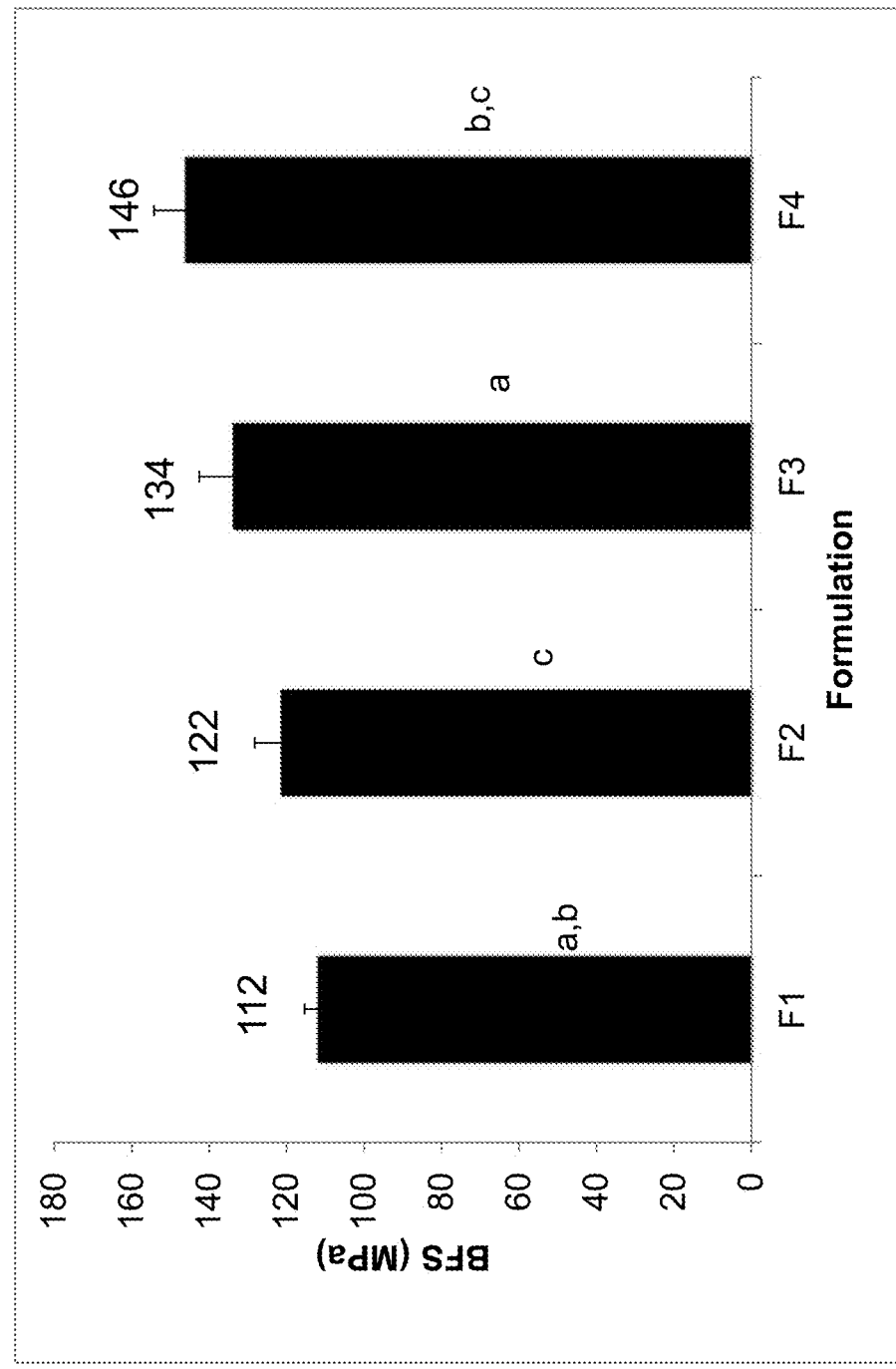
FIG. 18: Mean biaxial flexural strength (MPa) of the experimental dental composite, F1 containing both PLS and reactive Ca/Sr phosphates in comparison with control samples with either PLS (F2), phosphates (F3) or both (F4) removed. Samples were in water for 24 hours prior to testing. Same letters indicate statistically significant differences ($P<0.05$).
Figure 19:
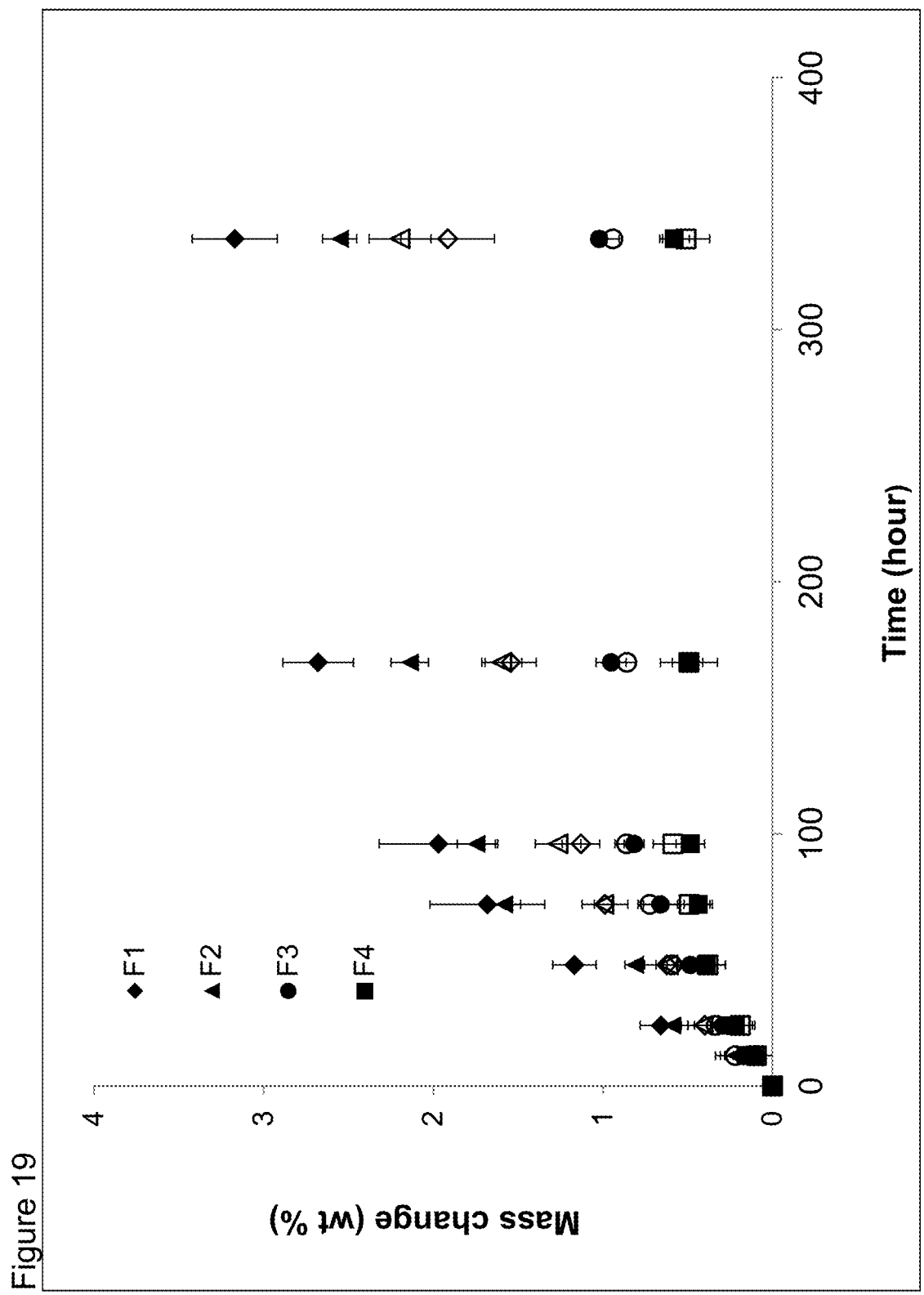
FIG. 19: Mass changes in simulated body fluid (SBF) or distilled water as a function of time of the experimental dental composite, F1 containing both PLS and reactive Ca/Sr phosphates in comparison with control samples with either PLS (F2), phosphates (F3) or both (F4) removed. Filled and unfilled symbols indicate a storage solution of SBF and distilled water respectively. Note the enhanced mass increase for F1 in SBF due to hydroxyapatite precipitation.
Figure 20B:
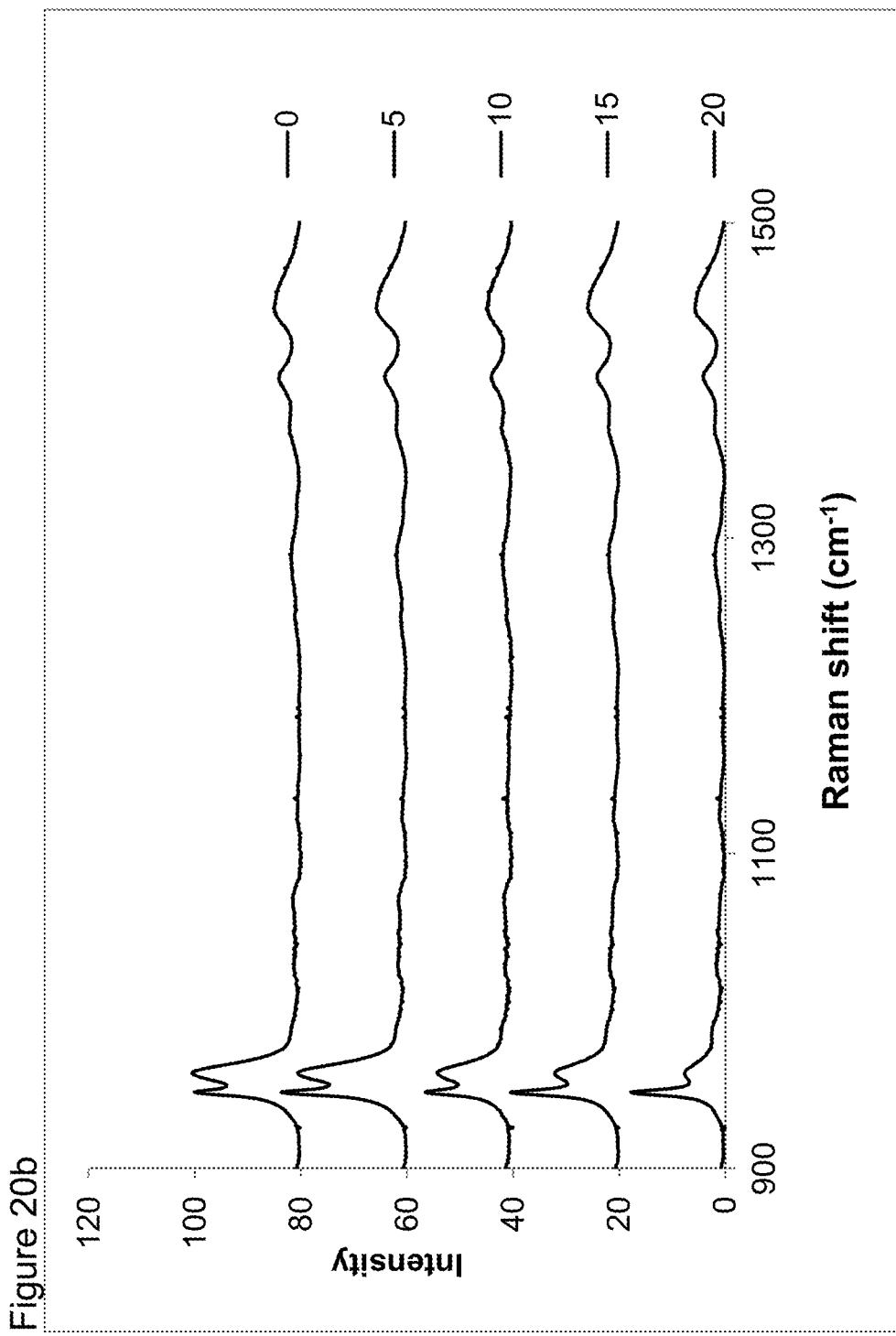
FIG. 20: Average surface Raman spectra obtained from a) the F1 and control specimens after submersion in SBF for 2 weeks b) F1 generated from the top (0 μm) deep into apatite layer for 20 μm. HA (960 cm-1), TSrP (948 cm-1), and glass (1400 cm-1) peaks are observed. At all levels the peak of glass can be seen whereas the peak attributed to HA declines with depth.
Figure 21:
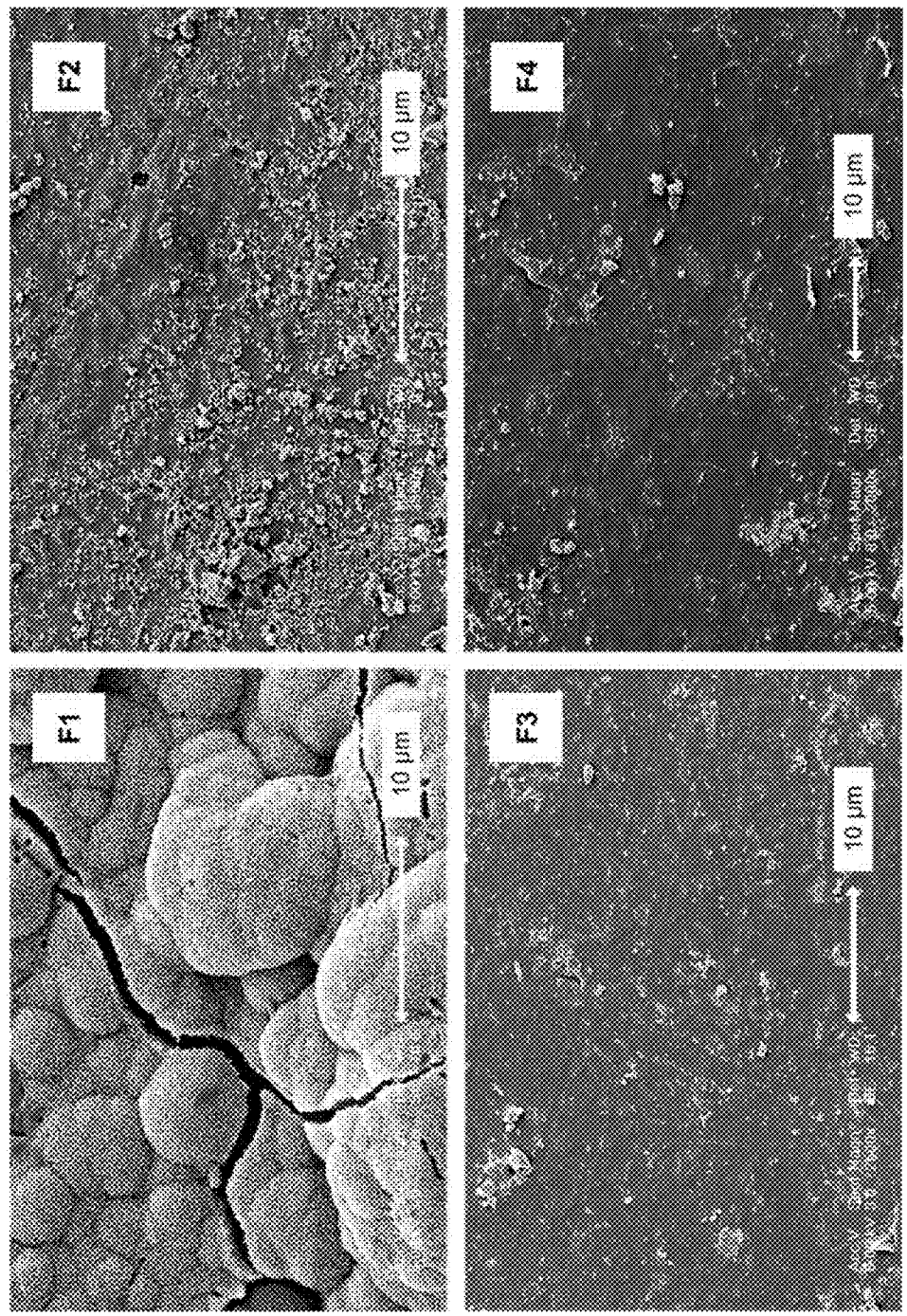
FIG. 21: SEM images of composite surface after submersion in SBF for 2 weeks. Only F1 showed clear apatite formation.

Together CaSrP and PLS addition only slightly decreased composite strength after 24 hours in water (FIG. 18). Strength decline is as a result of increasing water sorption. This water sorption can be seen as an increase in mass change with time in water (FIG. 19). Water sorption is beneficial as it expands the dental composite to compensate polymerisation shrinkage. The level observed in F1 is optimised to give sufficient expansion to just compensate polymerisation shrinkage without excessive strength reduction.

FIG. 19 additionally shows mass change in simulated body fluid (SBF) with F1 was significantly higher than in water. Raman mapping (FIG. 20) and SEM (FIG. 21) confirmed this was due to precipitation of a 10 µm thick hydroxyapatite (HA) layer. This is expected to enable the materials to stabilise demineralised dentine. In combination with expansion to compensate polymerisation shrinkage this helps prevent bacterial microleakage beneath a tooth restoration.

Example 13

ISO Testing of Remineralising Benefit of Formulations with Reactive Fillers and Polylysine a) Aim:

To investigate mechanical and physical properties of 2 re-mineralising dental composites (A & C) using ISO methods.

b) Methods:

BS EN ISO 4049:2009 Dentistry: Polymer-based restorative materials.

ISO 29022:2013 Dentistry—Adhesion—Notched-edge shear bond strength test with few modifications due to use of ivory dentine instead of human dentine.

ISO 23317: 2007 Implants for surgery—In vitro evaluation for apatite-forming ability of implant materials Draft BS EN ISO 17304 Dentistry—Polymerisation shrinkage: Method for determination of polymerisation shrinkage of polymer-based restorative materials In-house push-out test Push out force for restorations in 3 mm diameter holes drilled through 5 mm deep ivory blocks c) Materials:

| Chemicals | Supplier |
|---|---|
| UDMA, 0.7 and 7 μm glass | DMG |
| PPGDMA and 4 META | Polyscience |
| nano glass | Evonik Industries |
| MCPM | HIMED |
| TCP | Plasma Biotal Ltd |
| Polylysine | Handary |
| CQ | Sigma Aldrich |

Monomer (liquid) phase: UDMA: 72 wt. %; PGDMA: 24 wt. %; 4 META: 3 wt. %; CQ: 1 wt. %

Powder phase:

Formula A: Glass:89 wt. % (1:3:6 nano:0.7:7); CaP: 10 wt. % (1:1 MCPM:TCP); Polylysine: 1 wt. %

Formula C: Glass:78 wt. % (1:3:6 nano:0.7:7 μm); CaP: 20 wt. % (1:1 MCPM:TCP);

Polylysine: 2 wt. %

Powder to liquid ratio PLR was 4 unless otherwise stated.

The paste was mixed using a Speedmixer (Model: DAC 150.1 FVZ, Manufacturer: Hauschild Engineering, Distributor: Synergy Devices Ltd.) at 3500 rpm for 45 s.

All test specimens (discs or rods) were cured as required by ISO methods using a light cure gun (Kerr LED Demi-Plus).

Commercial products Z250 and Gradia (direct P-A2) were used for comparison.

d) Results:

i) Depth of cure (ISO 4049 standard >1.5 mm)

The height of the cylinder of cured material was measured in mm. All specimens were cured for 20 seconds.

| | Formula A | | Formula C | | Z250 | | Gradia | |
|---|---|---|---|---|---|---|---|---|
| Measurements | 4.23 | 4.06 | 4.08 | 3.92 | 5.54 | 5.51 | 5.26 | 5.34 |
| | 4.22 | 4.02 | 4.08 | 3.96 | 5.55 | 5.54 | 5.25 | 5.33 |
| | 4.18 | 4.07 | 4.09 | 3.93 | 5.57 | 5.56 | 5.24 | 5.38 |
| | 4.2 | 4.04 | 4.09 | 3.87 | 5.56 | 5.51 | 5.29 | 5.31 |
| | 4.21 | 4.02 | | | 5.6 | 5.51 | 5.2 | 5.33 |
| | 4.23 | 4.05 | | | | | 5.18 | 5.34 |
| Average (mm) | 4.21 | 4.04 | 4.08 | 3.92 | 5.56 | 5.53 | 5.24 | 5.34 |
| Depth of cure (mm)* | 2.1 | 2.02 | 2.04 | 1.96 | 2.78 | 2.76 | 2.62 | 2.67 |

*Note:
Depth of cure (mm) = 0.5 × average measurement of the specimens

Therefore, both formulations passed the depth of curing test.

ii) 3-Point Bending Flexural Strength (ISO 4049 Standard >80 MPa)

If 4 out of 5 specimens have greater strength than 80 MPa, the formulation passes the test. Formulae C and A had 5 and 6 specimens greater than 80 MPa, respectively. Therefore, both formulations passed the test. Z250 also passed, but Gradia has to be repeated.

| | 1 | 2 | 3 | 4 | 5 | 6 |
|---|---|---|---|---|---|---|
| Formula C | | | | | | |
| Strength (MPa) | 69.0 | 83.5 | 83.3 | 80.9 | 82.2 | 106 |
| Modulus (GPa) | 6.87 | 7.69 | 7.84 | 9.02 | 6.58 | 8.79 |
| Formula A | | | | | | |
| Strength (MPa) | 125.3 | 88.1 | 105.1 | 123.5 | 109.7 | 101 |
| Modulus (GPa) | 10.1 | 9.7 | 10.1 | 12.1 | 10.2 | 11.4 |
| Gradia | | | | | | |
| Strength (MPa) | 50.3 | 86.9 | 75.6 | 89.2 | 92.3 | |
| Modulus (GPa) | 6.8 | 6.1 | 5.7 | 6.2 | 6.9 | |
| Z250 | | | | | | |
| Strength (MPa) | 149.4 | 182.9 | 181.4 | 136.6 | 138.7 | |
| Modulus (GPa) | 12.0 | 13.4 | 11.5 | 10.2 | 11.5 | | iii) Water Sorption (ISO 4049 Standard <40 mq/cm3 at 7 Days in $H_2O$)

Figure 22:
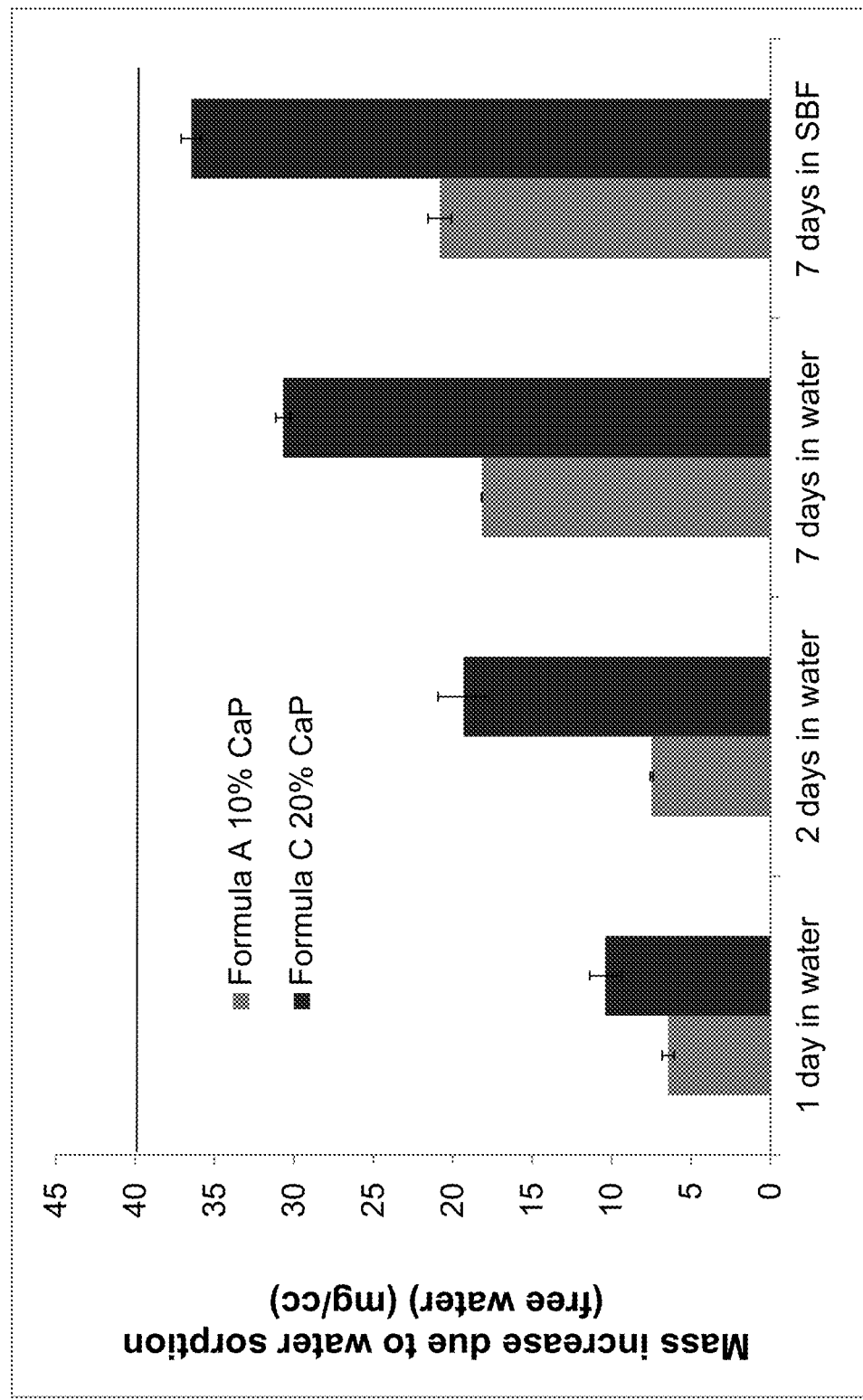
FIG. 22: Water sorption of dental composites of Example 13

In addition to the standard test using distilled H2O, water sorption was also assessed in simulated body fluid (SBF). Both formulations appeared to absorb more water in SBF than in H2O. This could be due to additional water in the hydroxyapatite (HA) precipitation layer formed on the surface of specimens soaked in SBF (see below). The total absorbed water largely depends on the amount of CaP within the materials. Formula C absorbs almost double the amount of water of formula A (FIG. 22). Yet, in all cases, calculated water content is beneath the ISO maximum. It should be noted, however, that the ISO test is unable to assess water levels that may be bound in new crystal structures formed within the new materials.

iv) Solubility (ISO 4049 Standard <7.5 mq/cm3 in $H_2O$ for 7 Days)

When specimens are soaked in water or SBF, components such as CaP or unreacted monomers/catalysts, may dissolve. Wth the remineralising composites, however, it is also possible for water to be tightly bound and not removed by the ISO method of dehydration. Additionally, in SBF hydroxyapatite can precipitate. The net value of solubility measured by the ISO test therefore reflects multiple processes rather than simply solubility as occurs with standard composites.

The solubility of formula A has negative values in both water (FIG. 23) and SBF. This indicates that the dissolved component mass was less than sample increase in mass due to water binding and hydroxyapatite precipitation. The difference in apparent solubility in SBF and in water should approximately equal the amount of HA precipitated. The value of 0.2 mg/cm3 can be calculated in the case of formula A.

For formula C, apparent solubility values were positive in both water (FIG. 23) and SBF but less in SBF due to HA precipitation. The difference was 2.3 mg/cm3 for formula C. This suggests that formula C encourages 10 times more HA formation on its surface than formula A. The reason could be due to higher CaP or polylysine content within the formulation.

In summary, both formulations passed this ISO test, though the systems are complex.

v) Remineralisation (ISO 23317)

Figure 24:
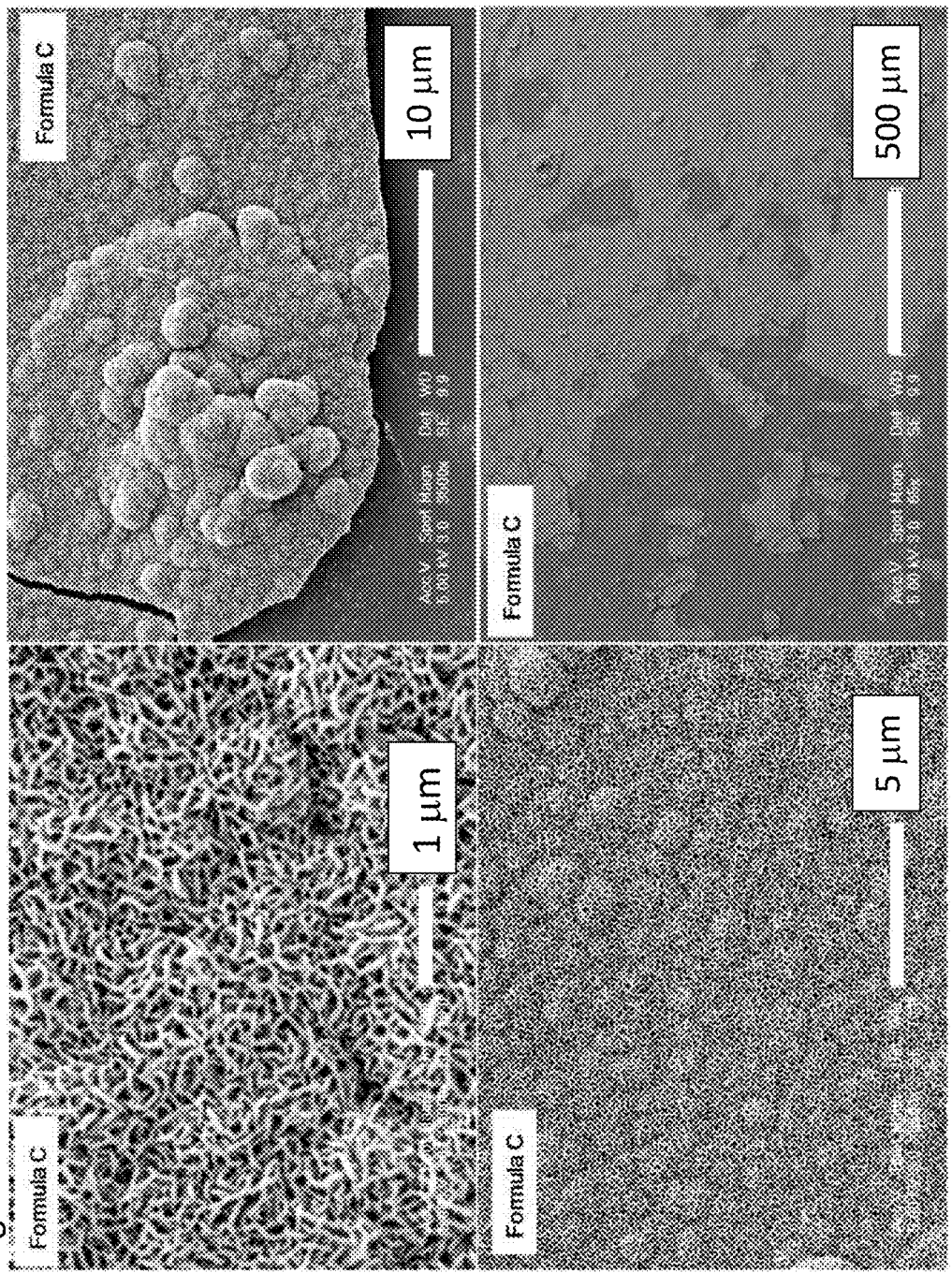
FIG. 24: SEM images of HA precipitation on the surface of Formula C specimens tested in Example 13 after 7-days soaking in SBF.
Figure 25:
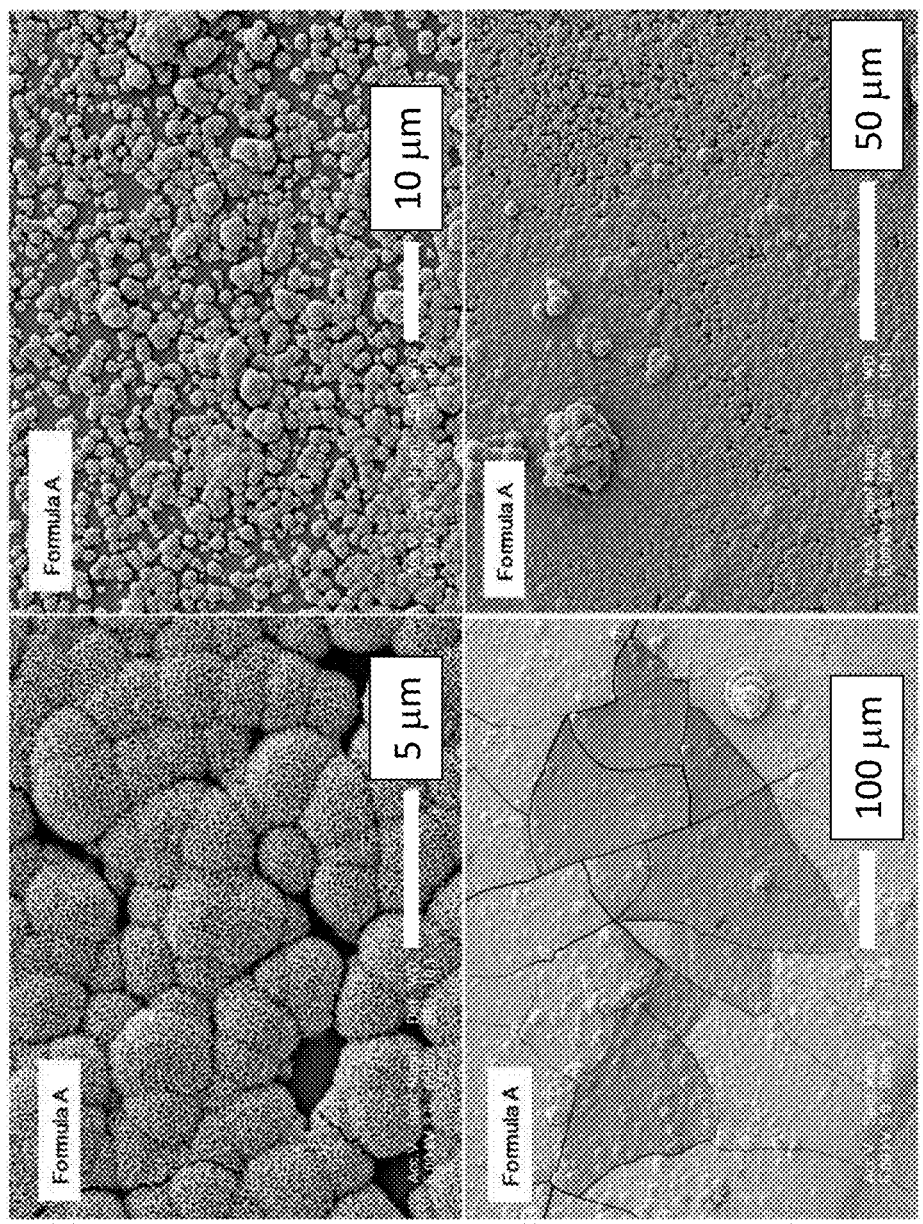
FIG. 25: Surface and fracture of Formula A tested in Example 13 after 7 day soaked in $H_2O$
Figure 26:
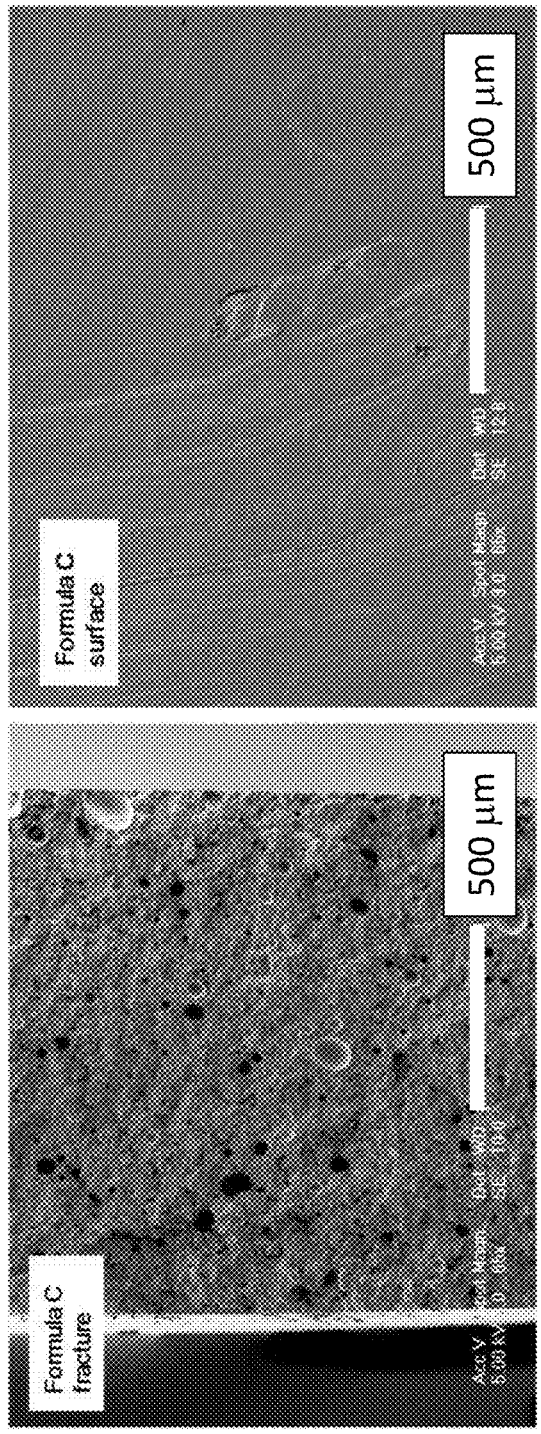
FIG. 26: Surface and fracture of Formula C tested in Example 13 after 7 day soaked in $H_2O$

The following remineralisation investigation is a test generally used to assess bone bonding potential rather than a test for standard composites which do not possess remineralising capability. Given the similarity in tooth and bone structure, however, this test will additionally provide an indication of the relative ability of materials to promote remineralisation of dentine. The test involves assessment by Scanning electron microscopy (SEM) as to whether hydroxyapatite (HA) precipitates on the surfaces of materials after immersion in simulated body fluid (SBF), SEM (FIGS. 24-26) suggests HA precipitated on formula C is much denser/thicker than that on formula A. This is in agreement with the amount of HA estimated using the ISO water sorption/solubility test in water versus SBF.

SEM of surfaces soaked in water confirms that HA precipitation is only observed in SBF and not pure water.

vi) Deboning Test from Ivory (Class 1 Model)

Ivory was used as a model to test adhesion of the new formulations to dentine, (formula C (FC4, and FC4.9 with PLR at 4 and 4.9, respectively), and formula A (FA4)). 4 types of ivory pre-treatment for each formulation were tested to assess effects of varying ivory composition and surface roughness. The commercial product Z250 was also tested for comparison. 3 repetitions were tested under each condition.

Figure 27:
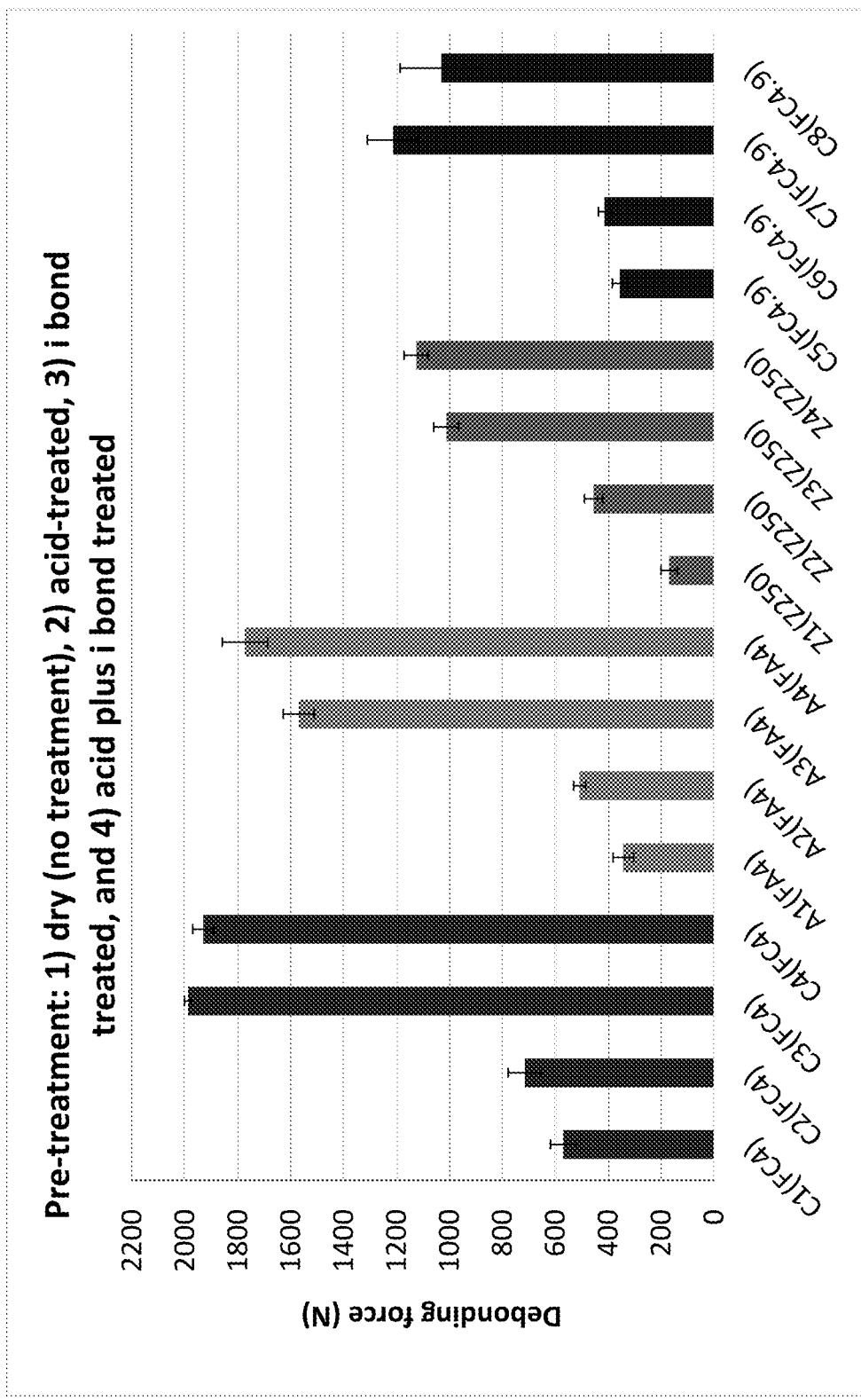
FIG. 27: Deboning test from ivory (class 1 model) using dental composites of Example 13

Referring to FIG. 27, and comparing C1, C2, C3, C4 (FC4) with A1, A2, A3, A4 (FA4), it can be seen that formula C (FC4) has better adhesion than formula A (FA4) irrespective of pre-treatment method. FC4 and FA4 both bonded better than Z250 (Z1, Z2, Z3 and Z4). If the powder to liquid ratio of FC4 was increased from 4 to 4.9, however, (C5, C6, C7 and C8) adhesion deteriorated to values comparable with Z250.

vii) Shear Bonding Test (ISO 29022:2013)

Figure 28:
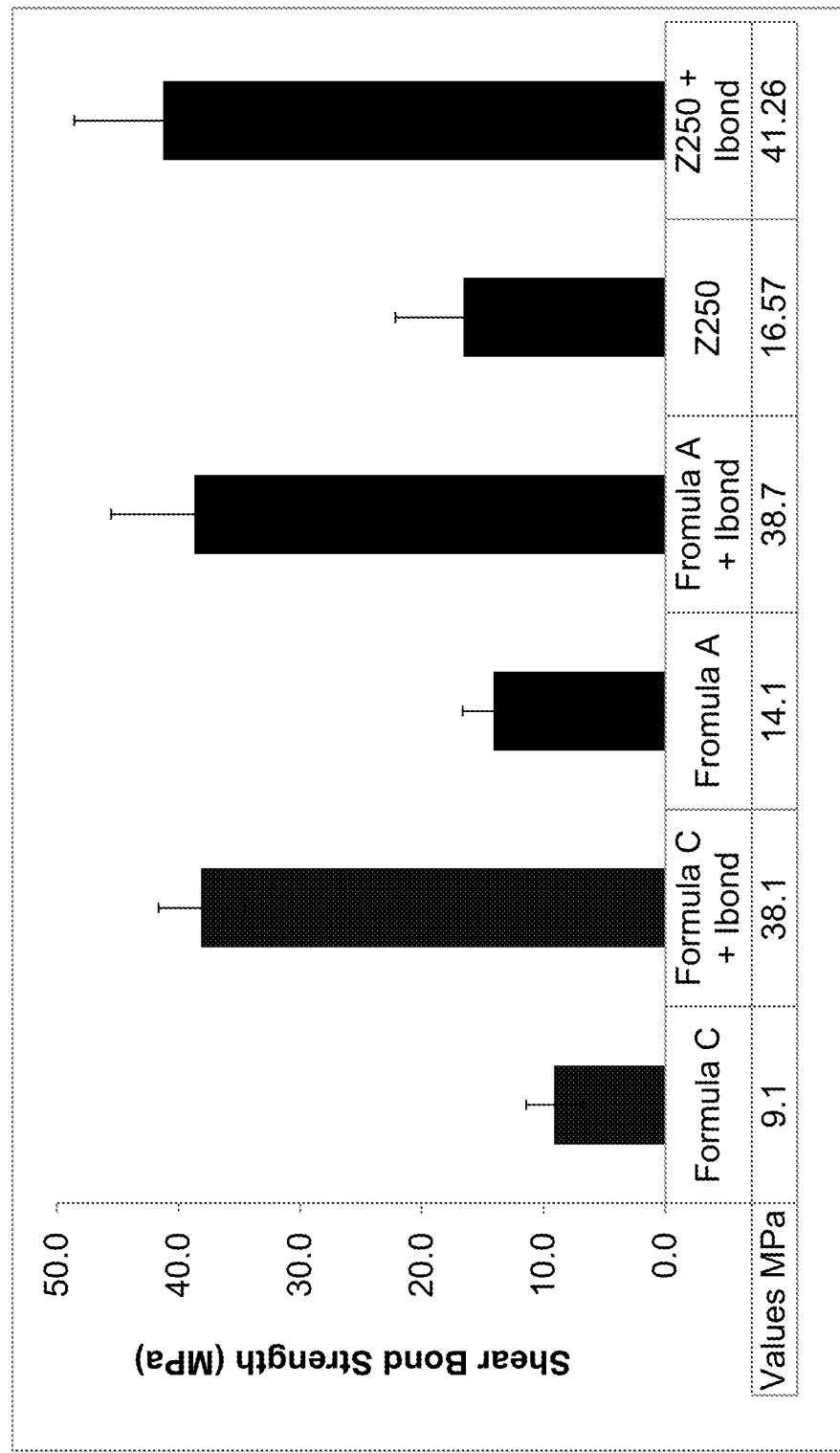
FIG. 28: Shear bonding test (ISO 29022:2013) using dental composites of Example 13

Shear test is a method used to determine the adhesive bond strength between direct dental restorative materials and tooth structure, e.g. dentine and enamel. The bond strength measured represents the force per unit area required to break a bonded assembly with failure occurring in or near the adhesive-substrate interface. ISO 29022:2013 was followed with a few modifications due to use of ivory dentine instead of human dentine. Controlled hydration of ivory was achieved by storing the ivory dentine in water for 24 h then leaving to dry in a humid environment (incubator) for 24 h. The ivory was subsequently treated with 35% phosphoric acid for 5 minutes to expose dentinal tubules (longer than human dentine due to higher mineral content). 10 samples were tested for each formulation. SD values are provided as error bars. The results are shown in FIG. 28.

viii) Polymerisation Shrinkage (ISO 17304)

Volume change (vol. %) before & after curing due to polymerisation was assessed through measuring changes in density. Monomer conversion (MC) was additionally measured through FTIR.

|  | Formula C | Formula A | Z250 | Gradia |
|---|---|---|---|---|
| Polymerisation shrinkage (vol. %) | 1.9 | 2.1 | 2.0 | 1.9 |
| MC (%) | 84 | 90 | 50 | 50 |

The polymerisation shrinkage of around 2 vol. % is close to the estimated maximum volume expansion due to water sorption in both experimental formulations (data not shown). New formulations have similar shrinkage to Z250 and Gradia despite much higher monomer conversions.

Summary Table

| | Flexural strength (MPa) | Depth of curing (mm) | Water sorption (μg/mm³) | Solubility (μg/mm³) | Polymerisation shrinkage (vol. %) | Volume expansion (%) | MC (%) |
|---|---|---|---|---|---|---|---|
| Formula A 10 wt. % CaP | 88.1 105.1 109.7 123.5 125.3 | 2.06 | 18.2 (H₂O) 20.8 (SBF) | −1.3 (H₂O) −1.5 (SBF) | 2.1 | <1.8% | 90 |
| Formula C 20 wt. % CaP | 80.9 82.2 83.3 83.3 106.0 | 2.00 | 30.6 (H₂O) 36.5 (SBF) | 4.2 (H₂O) 1.9 (SBF) | 1.9 | <2.6% | 84 |

REFERENCES

1. Stanczyk M. Study on modelling of PMMA bone cement polymerisation. Journal of Biomechanics 2005; 38(7): 1397-1403;
2. Stanczyk M, van Rietbergen B. Thermal analysis of bone cement polymerisation at the cement-bone interface. Journal of Biomechanics 2004; 37(12):1803-1810
3. Lohmann C H, Dean D D, Koster G, Casasola D, Buchhorn G H, Fink U et al. Ceramic and PMMA particles differentially affect osteoblast phenotype. Biomaterials 2002; 23(8):1855-1863
4. Schmitz J P, Hollinger J O, Milam S B. Reconstruction of bone using calcium phosphate bone cements: A critical review. Journal of Oral and Maxillofacial Surgery 1999; 57(9):1122-1126
5. Wolff K D, Swaid S, Nolte D, Bockmann R A, Holzle F, Muller-Mai C. Degradable injectable bone cement in maxillofacial surgery: indications and clinical experience in 27 patients. Journal of Cranio-Maxillofacial Surgery 2004; 32(2):71-79
6. Oh K S, Choi H W, Kim S R. Temperature rise and setting of beta-TCP-MCPM bone cement containing dense beta-TCP granules. Current Applied Physics 2005; 5:489-92;
7. Hofmann M P, Gbureck U, Grover L M, Barralet J E. Stearate salts as brushite bone cement setting retardants. Key Engineering Materials, 2005:19-22
8. Wang T, Feng Z. Dynamic mechanical properties of cortical bone: The effect of mineral content. Materials Letters 2005; 59:2277-80
9. Temenoff J S, Mikos A G. Injectable biodegradable materials for orthopedic tissue engineering. Biomaterials 2000; 21:2405-12
10. Kim B S, Hrkach J S, Langer R. Biodegradable photo-crosslinked poly(ether-ester) networks for lubricious coatings. Biomaterials 2000; 21(3):259-265;
11. Kumar N, Langer R S, Domb A J. Polyanhydrides: an overview. Advanced Drug Delivery Reviews 2002; 54(7): 889-910;
12. Timmer M D, Ambrose C G, Mikos A G. In vitro degradation of polymeric networks of poly(propylene fumarate) and the crosslinking macromer poly(propylene fumarate)-diacrylate. Biomaterials 2003; 24(4):571-577.
13. P V Hatton Glass-ionomer cements as drug-device combination products; Drug-device combination products: Delivery technologies and applications Edited by A Lewis, Biocompatibles U K Ltd, U K Woodhead Publishing Series in Biomaterials No. 22 Dec. 2009.
14. A M Young Antibacterial releasing dental restorative materials; Drug-device combination products: Delivery technologies and applications Edited by A Lewis, Biocompatibles U K Ltd, U K Woodhead Publishing Series in Biomaterials No. 22 Dec. 2009.
15. Mitsuo Niinomi (2011). Low Modulus Titanium Alloys for Inhibiting Bone Atrophy, Biomaterials Science and Engineering, Prof. Rosario Pignatello (Ed.),
16. R Benson and R Milner, Antibiotic-loaded bone cements. D Farrar, in Drug-device combination products: Delivery technologies and applications Edited by A Lewis, Biocompatibles U K Ltd, U K Woodhead Publishing Series in Biomaterials No. 22 Dec. 2009
17. Jean Palussie're et al., Eur Spine J (2005) 14: 982-991 Clinical results of an open prospective study of a bis-GMA composite in percutaneous vertebral augmentation.
18. Sideridou, Achilias, and Karava, Reactivity of Benzoyl Peroxide/Amine System as an Initiator for the Free Radical Polymerization of Dental and Orthopaedic Dimethacrylate Monomers: Effect of the Amine and Monomer; Chemical Structure Macromolecules 2006, 39, 2072-2080.
19. Gheduzzi et al.: Mechanical characterisation of three percutaneous vertebroplasty biomaterials; Mater Med (2006) 17: 421-426.
20. Galli et al. (2011), In vitro osteoblastic differentiation of human mesenchymal stem cells and human dental pulp stem cells on poly-L-lysine-treated titanium-6-aluminium-4-vanadium. J. Biomed. Mater. Res., 97A: 118-126.
21. Ciucurel and Sefton (2011): A Poloxamine-Polylysine Acrylate Scaffold for Modular Tissue Engineering, Journal of Biomaterials Science, Polymer Edition, 22:18, 2515-2528
22. Kar et al., Langmuir. 2010 Apr. 20; 26(8):5772-81.
23. Korzhikov et al. (2012), Polymers in orthopedic surgery and tissue engineering: From engineering materials to smart biofunctionalization of a surface. Polymer Science Series A, 54, pp 585-601.
24. van Landuyt et al. (2007), Systematic review of the chemical composition of contemporary dental adhesives, Biomaterials 28, 3757-3785
25. Abou Neel, E. A., Salih, V., Revell, P. A., & Young, A. M. (2012). Viscoelastic and biological performance of low-modulus, reactive calcium phosphate-filled, degradable, polymeric bone adhesives. *Acta Biomater,* 8 (1), 313-320.
26. Gellynck, K., Neel, E. A., Li, H., Mardas, N., Donos, N., Buxton, P., & Young, A. M. (2011). Cell attachment and response to photocured, degradable bone adhesives containing tricalcium phosphate and purmorphamine. *Acta Biomater,* 7 (6), 2672-2677.
27. Zhao, X., Olsen, I., Pratten, J., Knowles, J. C., & Young, A. M. (2011). Reactive calcium-phosphate-containing poly(ester-co-ether) methacrylate bone adhesives: Setting, degradation and drug release considerations. *Journal of Materials Science: Materials in Medicine,* 22 (9), 1993-2004.
28. Abou Neel, E. A., Palmer, G., Knowles, J. C., Salih, V., & Young, A. M. (2010). Chemical, modulus and cell attachment studies of reactive calcium phosphate filler-containing fast photo-curing, surface-degrading, polymeric bone adhesives. *Acta Biomater,* 6 (7), 2695-2703.
29. Young, A. M., Ho, S. M., Abou Neel, E. A., Ahmed, I., Barralet, J. E., Knowles, J. C., & Nazhat, S. N. (2009). Chemical characterization of a degradable polymeric bone adhesive containing hydrolysable fillers and interpretation of anomalous mechanical properties. *Acta Biomaterialia,* 5 (6), 2072-2083.
30. Mehdawi, I. M., Pratten, J., Spratt, D. A., Knowles, J. C., & Young, A. M. (2013). High strength re-mineralizing, antibacterial dental composites with reactive calcium phosphates. Dental Materials, 29 (4), 473-484.
31. Mehdawi, I., Abou Neel, E. A., Valappil, S. P., Palmer, G., Salih, V., Pratten, J., . . . Young, A. M. (2009). Development of remineralizing, antibacterial dental materials. Acta Biomaterialia, 5 (7), 2525-2539.
32. Shi, Lei, Lei Shi, Ling Wang, Yonghong Duan, Wei Lei, Zhen Wang, Jing Li, et al. 2013. "The Improved Biological Performance of a Novel Low Elastic Modulus Implant." PLoS ONE 8 (2) (February 21).
33. Ing-Lung Shih*, Ming-Haw Shen, Yi-Tsong Van, Bioresource Technology 97 (2006) 1148-1159
34. Kadlecova et al, J Control Release. 2013 Aug. 10; 169(3):276-88.
35. Samal et al. Chem. Soc. Rev., 2012,41, 7147-7194

The invention claimed is:

1. A process for production of a material which is a composite or a compomer, the process comprising the steps of:
   i) providing a fluid formulation comprising:
      (1) a fluid phase containing no water comprising at least one base monomeric or oligomeric hydrophobic compound capable of polymerisation and optionally cross-linking, which comprises a polymerisable methacrylate moiety,
      (2) a filler which comprises:
         (a) a reactive component comprising at least one calcium-containing compound, and
         (b) a glass powder or silane-treated glass powder, and
         (c) a cationic polymer, which is polylysine, present in the filler as solid particles; and
   ii) covalently polymerising and optionally cross-linking said base monomeric or oligomeric compound via the methacrylate moiety, thereby forming a solid polymer matrix comprising the particles of cationic polymer.

2. The process of claim 1, wherein the at least one base monomeric or oligomeric compound capable of polymerization is selected from urethane dimethacrylate (UDMA) and bisphenol A glycidyl methacrylate (BISGMA).

3. The process of claim 1, wherein the formulation further comprises one or more of the following additives: a polymerisation initiator and/or hydroxyquinone.

4. The process of claim 1, wherein the filler comprises an active agent selected from one or more of an antibacterial agent, chlorhexidine, cetyl pyridinium chloride, thymol, an antibiotic, gentamicin, tetracycline, oxycycline or minocycline.

5. The process of claim 4, wherein the filler comprises between about 2 and 10 wt % chlorhexidine.

6. The process of claim 1, wherein the method further comprises causing or allowing the calcium-containing compound in said filler to react with water absorbed into the polymer matrix to produce a solid filler material comprising the cationic polymer which is dispersed throughout the material.

7. The process of claim 1 wherein the calcium-containing compound is selected from the group consisting of: α tricalcium phosphate (TCP), β tricalcium phosphate (TCP), di calcium phosphate, dicalcium phosphate dihydrate (brushite), calcium dihydrogen phosphate, monocalcium phosphate monohydrate (MCPM), tetracalcium phosphate, α calcium pyrophosphate, β calcium pyrophosphate and γ calcium pyrophosphate.

8. The process of claim 1, wherein the reactive component is a mixture of β-TCP and MCPM, optionally in a 1:1 molar ratio, or a mixture of tristrontium phosphate and MCPM, optionally in a 1:1 molar ratio.

9. The process of claim 1, wherein the filler is present and comprises about 5 to 25 wt % glass fibres.

10. The process of claim 1, wherein the formulation comprises a polymerisation activator selected from N-tolylglycine glycidyl methacrylate (NTGGMA) or dimethyl paratoluidine (DMPT).

11. The process of claim 1, wherein the filler comprises about 0.1-20 wt % polylysine and about 0-10 wt % chlorhexidine.

12. The process of claim 1, wherein the fluid phase comprises a diluent monomer.

13. The process of claim 12, wherein the diluent monomer is selected from: polypropylene glycol dimethacrylate (PPGDMA), and triethylene glycol dimethacrylate (TEGDMA).

14. The process of claim 1, wherein the fluid phase comprises an adhesive monomer selected from the list consisting of: 4-methacryloxyethyl trimellitic anhydride (4-META); Pyromellitic Dimethacrylate (PMDM) and Methylmethacrylate, hydroxyethylmethacrylate (HEMA), present at 2-10 wt %.

15. The process of claim 14, wherein the fluid phase comprises 4-methacryloxyethyl trimellitic anhydride (4-META).

16. The process of claim 13, wherein fluid phase comprises Urethane Dimethacrylate (UDMA) and Polypropylene Glycol Dimethacrylate (PPGDMA).

17. The process of claim 7, wherein the calcium-containing compound is Monocalcium Phosphate Monohydrate (MCPM).

18. The process of claim 1, wherein the filler comprises about 0.5-10 wt % polylysine.

19. A method of tooth or bone repair, or of fixation of a dental or surgical implant into a cavity or location, which method comprises performing the process of claim 1, wherein:
   (i) the fluid formulation is introduced into the site of the tooth or bone damage or the cavity or location;
   (ii) polymerising and/or cross-linking said base monomeric or oligomeric compound is performed by curing said formulation to form a material which is adhered to the damaged tooth or bone or the cavity or location.

20. The method according to claim 19, wherein:
   (i) the cationic polymer promotes water sorption of the material;
   (ii) the cationic polymer promotes formation of a bone or dentine-like layer on the material, and re-adsorbs on this layer;
   (iii) the material comprises an active agent and the cationic polymer promotes release of the active agent;
   (iv) the cationic polymer enhances conversion of the polymerising and/or cross-linking compound to a polymer matrix; or
   (v) any combination thereof.

* * * * *

UNITED STATES PATENT AND TRADEMARK OFFICE
CERTIFICATE OF CORRECTION

PATENT NO. : 10,500,139 B2
APPLICATION NO. : 14/908911
DATED : December 10, 2019
INVENTOR(S) : Anne Margaret Young It is certified that error appears in the above-identified patent and that said Letters Patent is hereby corrected as shown below:

In the Claims

At Column 51, Claim 7, Line 45, "di calcium" should be replaced with -- dicalcium --.

Signed and Sealed this
Twenty-eighth Day of January, 2020

Andrei Iancu
*Director of the United States Patent and Trademark Office*